US007531553B2

(12) United States Patent
Di Pietro et al.

(10) Patent No.: US 7,531,553 B2
(45) Date of Patent: May 12, 2009

(54) HETEROCYCLIC COMPOUNDS AND METHODS OF USE

(75) Inventors: Lucian V. Di Pietro, Gloucester, MA (US); Jean-Christophe Harmange, Andover, MA (US); Benny C. Askew, Jr., Newbury Park, CA (US); Daniel Elbaum, Newton, MA (US); Julie Germain, Medford, MA (US); Gregory J. Habgood, Merrimac, MA (US); Joseph L. Kim, Wayland, MA (US); Vinod F. Patel, Acton, MA (US); Michele Potashman, Cambridge, MA (US); Simon van der Plas, Medford, MA (US)

(73) Assignee: Amgen Inc., Thousand Oaks, CA (US)

( * ) Notice: Subject to any disclaimer, the term of this patent is extended or adjusted under 35 U.S.C. 154(b) by 773 days.

(21) Appl. No.: 10/804,915

(22) Filed: Mar. 19, 2004

(65) Prior Publication Data

US 2004/0209892 A1    Oct. 21, 2004

Related U.S. Application Data

(60) Provisional application No. 60/456,691, filed on Mar. 21, 2003.

(51) Int. Cl.
*A61K 31/47* (2006.01)
*C07D 215/00* (2006.01)

(52) U.S. Cl. ...................................... 514/312; 546/153
(58) Field of Classification Search ................ 546/153; 514/312
See application file for complete search history.

(56) References Cited

U.S. PATENT DOCUMENTS 2,710,295 A    6/1955 Isler et al.

7,307,089 B2*  12/2007 Harris et al. ................. 514/312
7,326,788 B2*   2/2008 Wall et al. .................... 546/157
2005/0245547 A1* 11/2005 Kim et al. ................. 514/264.1

FOREIGN PATENT DOCUMENTS

| EP | 0 419 210 A1 | 3/1991 |
| JP | 57149341 A2 | 9/1982 |
| WO | WO 96/35681 | 11/1996 |
| WO | WO 02/44156 A2 | 6/2002 |
| WO | WO 03/074515 A1 | 9/2003 |
| WO | WO 03/082272 A1 | 9/2003 |

OTHER PUBLICATIONS

Database Beilstein: XP002289773, Phosphorus, Sulfur Silicon Relat. Elem., 48(1-4):149-155 (1990).
Database Beilstein: XP002289774, Bull. Pol. Acad. Sci. Chem., 50(3):309-322 (2002).
Database Beilstein: XP0022889775, Chem. Zvesti, 33:542 (1979).
Database Beilstein: XP0022889776, Diss. Pharm., 13:127-130 (1961).
Database Beilstein: XP0022889777, SK 278 131 B6, Feb. 7, 1996, p. 3, Example 7.
Breier et al., "The role of vascular endothelial growth factor in blood vessel formation", Trends in Cell Biology, 6:454-456 (1996).
Connell et al., "Patent focus on cancer chemotherapeutics. II Angiogenesis agents: Apr. 2000-Sep. 2000", Expert Opinion on Therapeutic Patents, 1:77-114 (2001).
Chemical Abstracts 98:90489, English abstract for patent B1 referenced above.

* cited by examiner

*Primary Examiner*—Kamal A Saeed
(74) *Attorney, Agent, or Firm*—Joseph W. Bulock; Ronald S. Hermenau

(57) ABSTRACT

Selected compounds are effective for prophylaxis and treatment of diseases, such as angiogenesis mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

15 Claims, No Drawings

HETEROCYCLIC COMPOUNDS AND METHODS OF USE

This application claims the benefit of U.S. Provisional Application No. 60/456,691 filed Mar. 21, 2003, which is hereby incorporated by reference.

FIELD OF THE INVENTION

This invention is in the field of pharmaceutical agents and specifically relates to compounds, compositions, uses and methods for treating cancer and angiogenesis-related disorders.

BACKGROUND OF THE INVENTION

Protein kinases represent a large family of proteins which play a central role in the regulation of a wide variety of cellular processes, maintaining control over cellular function. A partial list of such kinases includes ab1, Akt, bcr-ab1, Blk, Brk, Btk, c-kit, c-met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed 'Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

Compounds of the current invention have not been described as inhibitors of angiogenesis such as for the treatment of cancer.

DESCRIPTION OF THE INVENTION

A class of compounds useful in treating cancer and angiogenesis is defined by Formula I

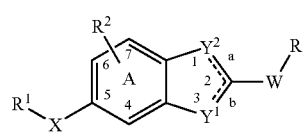

wherein W and X are independently selected from O, S(O)$_n$ and NR$^4$;

wherein Y$^1$ and Y$^2$ are independently selected from O, S(O)$_n$, N and NR$^4$;

wherein ring A optionally contains a nitrogen atom independently at position 4, 6 or 7;
wherein n is 0, 1 or 2;
wherein R is selected from
  a) substituted or unsubstituted 6-10 membered aryl,
  b) substituted or unsubstituted 5-6 membered heterocyclyl,
  c) substituted or unsubstituted 9-14 membered fused heterocyclyl,
  d) substituted or unsubstituted cycloalkyl, and
  e) substituted or unsubstituted cycloalkenyl,
    wherein substituted R is substituted with one or more substituents independently selected from halo, —$OR^3$, —$SR^3$, —$CO_2R$, —$C(O)NR^3R^3$, —$C(O)R^3$, —$NR^3$, oxo, —$OC(O)R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, alkylaminoalkoxyalkoxy, nitro, and lower alkyl substituted with $R^5$;
wherein $R^1$ is selected from
  a) substituted or unsubstituted 6-10 membered aryl,
  b) substituted or unsubstituted 4-6 membered heterocyclyl,
  c) substituted or unsubstituted 9-14 membered fused heterocyclyl,
  d) substituted or unsubstituted arylalkyl, and
  e) substituted or unsubstituted heterocyclylalkyl,
    where substituted $R^1$ is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —$SO_2NR^3R^3$—$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with $R^5$;
wherein $R^2$ is one or more substituents independently selected from H, halo, —$OR^3$, —$SR^3$—$CO_2R^3$, —$C(O)NR^3R^3$, —$C(O)R^3$, —$NR^3R^3$, —$SO_2R^3$, —$SO_2NR^3R^3$—$NR^3C(O)OR^3$, —$NR^3C(O)R^3$—$NR^3C(O)NR^3R^3$ optionally substituted cycloalkyl, optionally substituted 4-6 membered heterocyclyl, optionally substituted phenyl, cyano, alkylaminoalkoxy, alkylaminoalkoxyalkoxy, nitro, lower alkyl substituted with $R^5$, lower alkenyl substituted with $R^5$, and lower alkynyl substituted with $R^5$;
wherein $R^3$ is independently selected from H, lower alkyl, lower aminoalkyl, lower alkylaminoalkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl, and lower haloalkyl;
wherein $R^4$ is independently selected from H, and lower alkyl; and
wherein $R^5$ is one or more substituents independently selected from H, halo, —$OR^3$, —$SR^3$—$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, alkylaminoalkoxyalkoxy, nitro, lower alkyl, lower alkenyl and lower alkynyl;

and pharmaceutically acceptable derivatives thereof;
provided one of $Y^1$ and $Y^2$ is N or NH; further provided only one of dashed lines a and b indicates a double bond; further provided either X or W is not $S(O)_n$ when $Y^2$ is S and $Y^1$ is N; further provided $R^1$ is not 2-$HO_2C$-phenyl, 1H-pyrrole-2,5-dione or benzothiazole when $Y^2$ is S and $Y^1$ is N; further provided either R or $R^1$ is not substituted isoindolone when $Y^2$ is S and $Y^1$ is N; further provided $R^1$ is not benzyl when X is O, W is NH, $Y^2$ is O, $Y^1$ is N and R is 4-(diethylaminoethoxy)phenyl; further provided $R^1$ is not benzyl when $Y^2$ is NH, $Y^1$ is N and R is 5-(2-chloro-6-methylphenyl)-NHC(=O)-thiazol-2-yl or benzyl; further provided X and W are not both $S(O)_n$ when $Y^2$ is NH and $Y^1$ is N; further provided $R^2$ is not piperidinyl when X and W are NH, $Y^2$ is NH, $Y^1$ is N, R and $R^1$ are optionally substituted phenyl and ring A has nitrogens at positions 4 and 6; and further provided R, $R^1$ and $R^2$ are not all pyridyl or all triazolyl when $Y^2$ is NH, $Y^1$ is N and ring A has nitrogens at positions 4 and 6.

The invention also relates to compounds of Formula I wherein W and X are independently selected from O and $NR^4$; in conjunction with any of the above or below embodiments.

The invention also relates to compounds of Formula I wherein W is O or NH; in conjunction with any of the above or below embodiments. The invention also relates to compounds of Formula I wherein X is O or NH; in conjunction with any of the above or below embodiments. The invention also relates to compounds of Formula I wherein W is NH; in conjunction with any of the above or below embodiments.

The invention also relates to compounds of Formula I wherein $Y^1$ and $Y^2$ are independently selected from O, S, N, and $NR^4$; in conjunction with any of the above or below embodiments. The invention also relates to compounds of Formula I wherein $Y^2$ is selected from O, S, and NH; wherein $Y^1$ is N; and wherein dashed line b indicates a double bond; in conjunction with any of the above or below embodiments.

The invention also relates to compounds of Formula I wherein R is selected from substituted or unsubstituted aryl selected from phenyl, naphthyl, indanyl, indenyl and tetrahydronaphthyl, substituted or unsubstituted 5-6 membered heteroaryl, $C_{3-6}$-cycloalkyl, and substituted or unsubstituted 9-14 membered bicyclic or tricyclic heterocyclyl; wherein substituted R is substituted with one or more substituents independently selected from halo, —$OR^3$, oxo, —$SR^3$, —$SO_2R^3$, —$CO_2R^3$, —$C(O)NR^3R^3$, —$C(O)R^3$, —$NR^3R^3$—$NH(C_1$-$C_4$ alkylenyl$R^3$), —($C_1$-$C_4$ alkylenyl)$NR^3R^3$, —$SO_2NR^3R^3$, $NR^3C(O)OR^3$, —$NR^3C(O)R^3$, amino-$C_1$-$C_6$-alkyl, $C_1$-$C_6$-alkylamino-$C_1$-$C_6$-alkyl, $C_1$-$C_6$-alkylamino-$C_1$-$C_6$-alkoxy, $C_1$-$C_6$-alkylamino-$C_1$-$C_6$-alkoxy-$C_1$-$C_6$-alkoxy, optionally substituted 5-6 membered heterocyclylcarbonylalkyl, $C_{1-4}$-alkoxycarbonylamino-$C_{1-6}$alkyl,

optionally substituted $C_{4-6}$-cycloalkyl, optionally substituted 5-6 membered heterocyclyl, optionally substituted phenyl, optionally substituted phenyl-$C_{1-6}$-alkylenyl, optionally substituted 5-6 membered heterocyclyl-$C_1$-$C_6$-alkylenyl, 5-6 membered heterocyclyl-$C_2$-$C_6$-alkenylenyl, $C_{1-4}$-alkyl, cyano, $C_{1-4}$-hydroxyalkyl, nitro and $C_{1-4}$-haloalkyl; wherein $R^e$ and $R^f$ are independently selected from H and $C_{1-2}$-haloalkyl; wherein $R^7$ is selected from H, $C_{1-3}$-alkyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl; in conjunction with any of the above or below embodiments.

The invention also relates to compounds of Formula I wherein R is a substituted or unsubstituted ring selected from phenyl, indanyl, tetrahydronaphthyl, naphthyl, cyclohexyl, indazolyl, indolyl, 2,1,3-benzothiadiazolyl, isoxazolyl, pyrazolyl, thiazolyl, thiadiazolyl, thienyl, pyridyl, pyrimidinyl, pyridazinyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, isoindolyl, 2,3-dihydro-1H-indolyl, naphthyridinyl, benzothienyl, benzofuryl, 2,3-dihydro-benzofuryl, benzodioxolyl, benzimidazolyl, benzoxazolyl, benzthiazolyl, isoquinolyl, quinolyl, 1,2,3,4-tetrahydro-isoquinolyl, tetrahydroquinolyl, 2,3,4,4a,9,9a-hexahydro-1H-3-aza-fluorenyl, 5,6,7-trihydro-1,2,4-triazolo[3,4-a]isoquinolyl, benzodioxanyl and quinazolinyl; wherein substituted R is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholinylmethyl, methylpiperazinylmethyl, isopropyl-piperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, 4-chlorophenoxy, phenyloxy, piperdin-4-yloxy, 1-methylpiperdin-4-yloxy, piperidinylethoxy, morpholinylethyloxy, 4-methylpiperazinylethoxy, 4-isopropylpiperazinylethoxy, piperdin-4-methoxy, 4-methylpiperdin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; in conjunction with any of the above or below embodiments.

The invention also relates to compounds of Formula I wherein R is

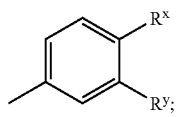

wherein $R^x$ is selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and wherein $R^y$ is selected from 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin-1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperdin-4-methoxy, 4-methylpiperdin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino)acetylamino and 2-(N,N-dimethylamino)ethylamino; in conjunction with any of the above or below embodiments.

The invention also relates to compounds of Formula I wherein $R^1$ is selected from
 substituted or unsubstituted 5-6 membered heteroaryl comprising one or more nitrogen atoms,
 substituted phenyl, and
 substituted or unsubstituted 9-10 membered bicyclic or 13-14 membered tricyclic heterocyclyl;

wherein substituted $R^1$ is substituted with one or more substituents independently selected from halo, $-OR^3$, $-SR^3$, $-SO_2R^3$, $-CO_2R^3$, $-C(O)NR^3R^3$, $-C(O)R^3$, $-NR^3R^3$, $-SO_2NR^3R^3$ $-NR^3C(O)OR^3$, $-NR^3C(O)R^3$, optionally substituted 5-6 membered heterocyclyl, optionally substituted phenyl, nitro, cyano, $C_{1-4}$-alkylamino-$C_{1-4}$-alkoxy, and $C_{1-4}$-alkyl substituted with $R^5$; in conjunction with any of the above or below embodiments.

The invention also relates to compounds of Formula I wherein $R^1$ is a substituted or unsubstituted ring selected from pyrazolyl, triazolyl, pyridyl, pyrimidinyl, triazinyl, pyridazinyl, substituted phenyl, indazolyl, indolyl, isoindolyl, quinolinyl, isoquinolinyl, benzotriazolyl, benzo[1,3]dioxolyl, pyrrolo[2,3-d]pyrimidin-4-yl, 2-oxo-1,3-dihydro-pyrrolo[2,3-d]pyridin-4-yl, pyrazolo[2,3-b]pyridin-4-yl, imidazo[4,5-b]pyridin-4-yl, 2,3-dihydrobenzofuryl, 2-oxo-1,2-dihydroquinolyl, naphthyridinyl and quinazolinyl; wherein substituted $R^1$ is substituted with one or more substituents independently selected from halo, hydroxy, $C_{1-3}$-alkyl, $C_{1-2}$-alkoxy, $C_{1-2}$-alkoxy-$C_{1-2}$-alkoxy, optionally substituted 5-6 membered heterocyclyl-$C_{1-2}$-alkoxy, amino, $C_{1-2}$-alkylamino, aminosulfonyl, $-NR^3C(O)OR^3$, $-NR^3C(O)R^3$, optionally substituted 5-6 membered heterocyclyl, optionally substituted phenyl, nitro, cyano, $C_{1-2}$-alkylamino-$C_{1-2}$-alkoxy, $C_{1-2}$-alkylamino-$C_{1-2}$-alkyl, $C_{1-2}$-alkylamino-$C_{2-3}$-alkylamino, $C_{1-2}$-hydroxyalkyl, $C_{1-2}$-aminoalkyl, and $C_{1-2}$-haloalkyl; in conjunction with any of the above or below embodiments.

The invention also relates to compounds of Formula I wherein $R^1$ is a substituted or unsubstituted ring selected from 4-pyridyl, triazolyl, 4-pyrimidinyl, 4-pyridazinyl, phenyl, 5-indazolyl, 4-quinolyl, indolyl, isoindolyl, benzotriazolyl, benzo[1,3]dioxolyl, pyrrolo[2,3-d]pyrimidin-4-yl, 2-oxo-1,3-dihydro-pyrrolo[2,3-d]pyridin-4-yl, pyrazolo[2,3-b]pyridin-4-yl, imidazo[4,5-b]pyridin-4-yl, pyrrolo[2,3-b]pyridin-4-yl, 2,3-dihydrobenzofuryl, 2-oxo-1,2-dihydroquinol-7-yl, and 4-quinozalinyl; wherein substituted $R^1$ is substituted with one or more substituents independently selected from chloro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholino-ethoxy, pyrrolidin-1-ylethoxy, 4-methylpiperazin-1-ylethoxy, dimethylaminoethylamino, dimethylaminopropylamino, methyl, ethyl, propyl, cyano, hydroxymethyl, aminomethyl, aminocarbonyl, nitro, trifluoromethyl, optionally substituted piperidinyl, morpholinyl, optionally substituted piperazinyl, and optionally substituted phenyl; in conjunction with any of the above or below embodiments.

The invention also relates to compounds of Formula I wherein $R^2$ is one or more substituents independently selected from H, halo, hydroxy, $C_{1-2}$-alkoxy, $C_{1-2}$-haloalkoxy, amino, $C_{1-2}$-alkylamino, optionally substituted 5-6 membered heterocyclyl-$C_{1-2}$-alkylamino, aminosulfonyl, $C_{3-6}$-cycloalkyl, optionally substituted 5-6 membered heterocyclyl, optionally substituted phenyl, $C_{1-4}$-alkyl, cyano, $C_{1-2}$-hydroxyalkyl, $C_{1-3}$-carboxyalkyl, nitro, $C_{2-3}$-alkenyl, $C_{2-3}$-alkynyl and $C_{1-2}$-haloalkyl; in conjunction with any of the above or below embodiments.

The invention also relates to compounds of Formula I wherein $R^2$ is one or more substituents independently selected from H, chloro, fluoro, bromo, hydroxy, methoxy, ethoxy, trifluoromethoxy, amino, dimethylamino, aminosulfonyl, carboxymethyl, cyclopropyl, optionally substituted phenyl, methyl, ethyl, propyl, cyano, hydroxymethyl, nitro, propenyl, propynyl, trifluoromethyl and unsubstituted or substituted heteroaryl selected from thienyl, furanyl, pyridyl, imidazolyl, and pyrazolyl; in conjunction with any of the above or below embodiments.

The invention also relates to compounds of Formula I wherein $R^2$ is H; wherein $R^3$ is selected from H, $C_{1-4}$-alkyl, phenyl, phenyl-$C_{1-4}$-alkyl, 4-6 membered heterocyclyl, 4-6 membered heterocyclyl-$C_{1-3}$-alkyl, $C_3$-$C_6$ cycloalkyl and $C_{1-2}$-haloalkyl; in conjunction with any of the above or below embodiments.

The invention also relates to compounds of Formula I wherein $R^4$ is independently selected from H, $C_{1-3}$-alkyl, phenyl, 5-6 membered heterocyclyl, $C_5$-$C_6$ cycloalkyl, and $C_{1-3}$-haloalkyl; in conjunction with any of the above or below embodiments.

The invention also relates to compounds of Formula I
where substituted $R^1$ is substituted with one or more substituents selected from halo, —$OR^3$, —$SR^3$, —$SO_2R^3$— $CO_2R^3$, —$C(O)NR^3$, $R^3$, —$C(O)R^3$, —$NR^3R^3$, —$SO_2NR^3R^3$, —$NR^3C(O)R^3$, —$NR^3C(O)R^3$, optionally substituted 3-6 membered heterocyclyl, optionally substituted phenyl, nitro, cyano, oxo, and lower alkyl substituted with $R^6$;
wherein $R^2$ is one or more substituents independently selected from H, halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, nitro, and lower alkyl substituted with $R^6$;
wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl, lower aminoalkyl, lower alkylaminoalkyl and lower haloalkyl;
wherein $R^4$ is independently selected from H, and $C_{1-2}$ alkyl; and
wherein $R^6$ is one or more substituents independently selected from H, halo, —$OR^3$, —$SR^3$, —$CO_2R^3$, —$CONR^3R^3$, —$COR^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy and nitro;

and pharmaceutically acceptable derivatives thereof;
provided $R^1$ is not 5-((2-chloro-6-methylphenyl)-aminocarbonyl)thiazol-2-yl when $Y^2$ is NH, W is NH and X is NH; further provided $R^1$ is not 2-(substituted aminocarbonyl) pyrid-4-yl when $Y^2$ is NH; further provided $R^1$ is not 2-(substituted aminocarbonyl)pyrid-4-yl when $Y^2$ is O and when R is phenyl or substituted phenyl.

The invention also relates to compounds of Formula I wherein R is a substituted or unsubstituted ring selected from phenyl, indanyl, tetrahydronaphthyl, naphthyl, cyclohexyl, indazolyl, indolyl, 2,1,3-benzothiadiazolyl, isoxazolyl, pyrazolyl, thiazolyl, thiadiazolyl, thienyl, pyridyl, pyrimidinyl, pyridazinyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, isoindolyl, 2,3-dihydro-1H-indolyl, naphthyridinyl, benzothienyl, benzofuryl, 2,3-dihydro-benzofuryl, benzodioxolyl, benzimidazolyl, benzoxazolyl, benzthiazolyl, isoquinolyl, quinolyl, 1,2,3,4-tetrahydro-isoquinolyl, tetrahydroquinolyl, 2,3,4,4a,9,9a-hexahydro-1H-3-aza-fluorenyl, 5,6,7-trihydro-1,2,4-triazolo[3,4-a]isoquinolyl, benzodioxanyl and quinazolinyl; wherein substituted R is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholin-4-ylmethyl, 4-methylpiperazin-1-ylmethyl, 4-isopropyl-piperazin-1-ylmethyl, 4-methylpiperazin-1-ylpropyl, morpholin-4-ylpropyl, methylpiperidinylmethyl, morpholin-4-ylethyl, 1-(4-morpholinyl)-2,2-dimethylpropyl, piperidinylethyl, piperidinylmethyl, piperidinylpropyl, 4-(dimethylaminoethyl)piperazin-1-ylmethyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, diethylaminoethoxy, 4-chlorophenoxy, phenyloxy, 1-methylpiperdin-4-yloxy, piperdin-4-yloxy, piperidinylethoxy, morpholin-4-ylethyloxy, 4-methylpiperazin-1-ylethoxy, 4-isopropylpiperazinylethoxy, piperdin-4-ylmethoxy, 4-methylpiperdin-1-ylmethoxy, 1-methylpiperdin-4-ylmethoxy, 1-isopropylpiperdin-4-ylmethoxy, 1-methylpyrrolidin-2-ylmethoxy, 1-isopropylpyrrolidin-2-ylmethoxy, 1-isopropylpyrrolidin-3-ylmethoxy, 1-pyrrolidinylmethoxy, 1-pyrrolidinylethoxy, 1-methylpyrrolidin-3-ylmethoxy, 3-(dimethylamino)pyrrolidin-1-ylethoxy, 2-tetrahydrofurylmethoxy, isopropoxy, methoxy and ethoxy; in conjunction with any of the above or below embodiments.

The invention also relates to compounds of Formula I wherein R is

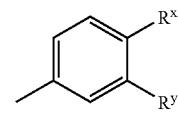

wherein $R^x$ is selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and wherein $R^y$ is selected from H, 4-methylpiperazinylsulfonyl, trifluoromethyl, morpholinylmethyl, 4-methylpiperazinylmethyl, 3-dimethylaminopyrrolidin-1-ylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 1-methylpyrrolidin-2-ylmethyl, dimethylaminoethyl, dimethylaminoethoxy, piperidinylethoxy, morpholinylethyloxy, 4-methylpiperazin-1-ylethoxy, 4-(dimethylaminoethyl)piperazin-1-ylmethyl, 4-isopropylpiperazinylmethoxy, piperdin-4-ylmethoxy, 4-methylpiperdin-1-ylmethoxy, 1-methylpiperdin-4-ylmethoxy, 1-isopropylpiperdin-4-ylmethoxy, 1-pyrrolidinylmethoxy, 1-pyrrolidinylethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-tetrahydrofurylmethoxy, diethylaminoethoxy, 2-(N,N-dimethylamino)acetylamino and 2-(N,N-dimethylamino) ethylamino; in conjunction with any of the above or below embodiments.

The invention also relates to compounds of Formula I wherein $R^1$ is a substituted or unsubstituted ring selected from 4-pyridyl, triazolyl, 4-pyrimidinyl, 4-pyridazinyl, phenyl, 6-indazolyl, 4-quinolyl, indolyl, isoindolyl, benzotriazolyl, benzo[1,3]dioxolyl, pyrrolo[2,3-d]pyrimidin-4-yl, 2-oxo-1,3-dihydro-pyrrolo[2,3-d]pyridin-4-yl, pyrazolo[2,3,b]pyridin-4-yl, imidazo[4,5-b]pyridin-4-yl, pyrrolo[2,3-b]pyridin-4-yl, 2,3-dihydrobenzofuryl, 2-oxo-1,2-dihydroquinol-7-yl, and 4-quinazolinyl; wherein substituted $R^1$ is substituted with one or more substituents independently selected from chloro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholinoethoxy, pyrrolidin-1-ylethoxy, 4-methylpiperazin-1-ylethoxy, methylaminocarbonyl, 1-pyrrolidinylbutylaminocarbonyl, dimethylaminoethylamino, dimethylaminopropylamino, methyl, ethyl, propyl, cyano, hydroxymethyl, aminomethyl, aminocarbonyl, nitro, trifluoromethyl, optionally substituted piperidinyl, morpholinyl, optionally substituted piperazinyl, and optionally substituted phenyl; in conjunction with any of the above or below embodiments.

The invention also relates to compounds of Formula I wherein $R^2$ is H or Cl; in conjunction with any of the above or below embodiments.

The invention also relates to compounds of Formula II

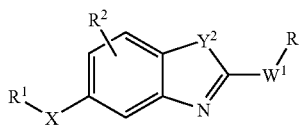

II wherein $W^1$ and X are independently O or NH;
wherein $Y^2$ is O or $NR^4$;
wherein n is 0, 1 or 2;
wherein R is selected from
a) substituted or unsubstituted 6-10 membered aryl,
b) substituted or unsubstituted 5-6 membered heterocyclyl,
c) substituted or unsubstituted 9-13 membered fused heterocyclyl, and
d) substituted or unsubstituted cycloalkyl,
wherein substituted R is substituted with one or more substituents independently selected from halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, oxo, —$OC(O)R^3$, optionally substituted cycloalkyl, optionally substituted 4-6 membered heterocyclyl, optionally substituted phenyl, cyano, alkylaminoalkoxy, alkylaminoalkoxyalkoxy, nitro and lower alkyl substituted with $R^6$;
wherein $R^1$ is selected from
a) unsubstituted or substituted 5- or 6-membered nitrogen-containing heteroaryl,
b) unsubstituted or substituted 9- or 10-membered fused nitrogen-containing heteroaryl, and
c) phenyl,
where substituted $R^1$ is substituted with one or more substituents selected from halo, —$OR^3$, —$SR^3$, —$SO_2R^3$, —$CO_2R^3$—$C(O)NR^3R^3$, —$C(O)R^3$, —$NR^3R^3$, —$SO_2NR^3R^3$—$NR^3C(O)OR^3$, —$NR^3C(O)R^3$, optionally substituted 3-6 membered heterocyclyl, optionally substituted phenyl, nitro, cyano, oxo, and lower alkyl substituted with $R^6$;
wherein $R^2$ is one or more substituents independently selected from H, halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, nitro, and lower alkyl substituted with $R^6$;
wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl, lower aminoalkyl, lower alkylaminoalkyl and lower haloalkyl;
wherein $R^4$ is independently selected from H, and $C_{1-2}$ alkyl; and
wherein $R^6$ is one or more substituents independently selected from H, halo, —$OR^3$—$SR^3$, —$CO_2R^3$, —$CONR^3R^3$, —$COR^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy and nitro;

and pharmaceutically acceptable derivatives thereof.

The invention also relates to compounds of Formula II wherein $W^1$ is NH; in conjunction with any of the above or below embodiments. The invention also relates to compounds of Formula II wherein X is O; in conjunction with any of the above or below embodiments. The invention also relates to compounds of Formula II wherein X is NH; in conjunction with any of the above or below embodiments. The invention also relates to compounds of Formula II wherein $Y^2$ is NH or $NCH_3$; in conjunction with any of the above or below embodiments. The invention also relates to compounds of Formula II wherein $Y^2$ is O; in conjunction with any of the above or below embodiments.

The invention also relates to compounds of Formula II wherein R is a substituted or unsubstituted ring selected from phenyl, indanyl, tetrahydronaphthyl, naphthyl, cyclohexyl, indazolyl, indolyl, 2,1,3-benzothiadiazolyl, isoxazolyl, pyrazolyl, thiazolyl, thiadiazolyl, thienyl, pyridyl, pyrimidinyl, pyridazinyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, isoindolyl, 2,3-dihydro-1H-indolyl, naphthyridinyl, benzothienyl, benzofuryl, 2,3-dihydro-benzofuryl, benzodioxolyl, benzimidazolyl, benzoxazolyl, benzthiazolyl, isoquinolyl, quinolyl, 1,2,3,4-tetrahydro-isoquinolyl, tetrahydroquinolyl, 2,3,4,4a,9,9a-hexahydro-1H-3-aza-fluorenyl, 5,6,7-trihydro-1,2,4-triazolo[3,4-a]isoquinolyl, benzodioxanyl and quinazolinyl; wherein substituted R is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholinylmethyl, methylpiperazinylmethyl, isopropyl-piperazinylmethyl, methylpiperazinylpropyl, morpholinylpropyl, methylpiperidinylmethyl, morpholinylethyl, 1-(4-morpholinyl)-2,2-dimethylpropyl, piperidinylethyl, piperidinylmethyl, piperidinylpropyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, 4-chlorophenoxy, phenyloxy, 1-methylpiperdin-4-yloxy, piperdin-4-yloxy, piperidinylethoxy, morpholinylethyloxy, 4-methylpiperazinylethoxy, 4-isopropylpiperazinylethoxy, piperdin-4-methoxy, 4-methylpiperdin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylamino)pyrrolidin-1-ylethoxy, isopropoxy, methoxy and ethoxy; in conjunction with any of the above or below embodiments.

The invention also relates to compounds of Formula II wherein R is

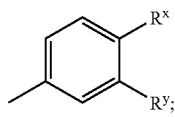

wherein $R^x$ is selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and wherein $R^y$ is selected from 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin-1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperdin-4-methoxy, 4-methylpiperdin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino)acetylamino and 2-(N,N-dimethylamino)ethylamino; in conjunction with any of the above or below embodiments.

The invention also relates to compounds of Formula II wherein R is substituted or unsubstituted 5-6 membered heterocyclyl; in conjunction with any of the above or below embodiments.

The invention also relates to compounds of Formula II wherein R is substituted or unsubstituted 9-11 membered fused heterocyclyl; in conjunction with any of the above or below embodiments.

The invention also relates to compounds of Formula II wherein $R^1$ is selected from unsubstituted or substituted 5- or 6-membered nitrogen-containing heteroaryl; in conjunction with any of the above or below embodiments.

The invention also relates to compounds of Formula II wherein $R^1$ is selected from unsubstituted or substituted phenyl; in conjunction with any of the above or below embodiments.

The invention also relates to compounds of Formula II wherein $R^1$ is selected from unsubstituted or substituted 9- or 10-membered nitrogen-containing partially saturated heterocyclyl and unsubstituted or substituted 9- or 10-membered nitrogen-containing heteroaryl; in conjunction with any of the above or below embodiments.

The invention also relates to compounds of Formula II wherein $R^1$ is a substituted or unsubstituted ring selected from 4-pyridyl, triazolyl, 4-pyrimidinyl, 4-pyridazinyl, phenyl, 5-indazolyl, 4-quinolyl, indolyl, isoindolyl, benzotriazolyl, benzo[1,3]dioxolyl, pyrrolo[2,3-d]pyrimidin-4-yl, 2-oxo-1,3-dihydro-pyrrolo[2,3-d]pyridin-4-yl, pyrazolo[2,3,b]pyridin-4-yl, imidazo[4,5-b]pyridin-4-yl, pyrrolo[2,3-b]pyridin-4-yl, 2,3-dihydrobenzofuryl, 2-oxo-1,2-dihydroquinol-7-yl, and 4-quinozalinyl; wherein substituted $R^1$ is substituted with one or more substituents independently selected from chloro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholinoethoxy, pyrrolidin-1-ylethoxy, 4-methylpiperazin-1-ylethoxy, dimethylaminoethylamino, dimethylaminopropylamino, methyl, ethyl, propyl, cyano, hydroxymethyl, aminomethyl, aminocarbonyl, nitro, trifluoromethyl, optionally substituted piperidinyl, morpholinyl, optionally substituted piperazinyl, and optionally substituted phenyl; in conjunction with any of the above or below embodiments.

The invention also relates to compounds of Formula II wherein $W^1$ and X are independently O or NH;
wherein $Y^2$ is O or NH;
wherein R is selected from
a) substituted or unsubstituted 6-10 membered aryl,
b) substituted or unsubstituted 5-6 membered heterocyclyl,
c) substituted or unsubstituted 9-13 membered fused heterocyclyl, and
d) substituted or unsubstituted cycloalkyl,
wherein substituted R is substituted with one or more substituents independently selected from halo, —$OR^3$, —$SR^3$, —$CO_2R^3$—$C(O)NR^3R^3$, —$C(O)R^3$—$NR^3R^3$, —$SO_2R^3$, —$SO_2NR^3R^3$, —$NR^3C(O)OR^3$, —$NR^3C(O)R^3$, —$NR^3C(O)NR^3R^3$, oxo, —$OC(O)R^3$, optionally substituted cycloalkyl, optionally substituted 4-6 membered heterocyclyl, optionally substituted phenyl, cyano, alkylaminoalkoxy, alkylaminoalkoxyalkoxy, nitro and lower alkyl substituted with $R^6$;
wherein $R^1$ is selected from
a) unsubstituted or substituted 5- or 6-membered nitrogen-containing heteroaryl,
b) unsubstituted or substituted 9- or 10-membered fused nitrogen-containing heteroaryl, and
c) phenyl,
where substituted $R^1$ is substituted with one or more substituents selected from halo, —$OR^3$, —$SR^3$, —$SO_2R^3$, —$CO_2R^3$, —$C(O)NR^3R^3$, —$C(O)R^3$, —$NR^3R^3$, —SO₂NR³R³, —NR³C(O)OR³, —NR³C(O)R³, optionally substituted 3-6 membered heterocyclyl, optionally substituted phenyl, nitro, cyano, oxo, and lower alkyl substituted with R⁶;

wherein R² is one or more substituents independently selected from H, halo, —OR³, —SR³, —CO₂R³, —C(O)NR³R³, —C(O)R³, —NR³R³, —SO₂R³, —SO₂NR³R³, —NR³C(O)OR³, —NR³C(O)R³, —NR³C(O)NR³R³, optionally substituted cycloalkyl, optionally substituted 4-6 membered heterocyclyl, optionally substituted phenyl, cyano, alkylaminoalkoxy, nitro, and lower alkyl substituted with R⁶;

wherein R³ is independently selected from H, lower alkyl, optionally substituted phenyl, optionally substituted 3-6 membered heterocyclyl, optionally substituted C₃-C₆-cycloalkyl, optionally substituted phenylalkyl, optionally substituted 3-6 membered heterocyclylalkyl, optionally substituted C₃-C₆ cycloalkylalkyl, lower aminoalkyl, lower alkylaminoalkyl and lower haloalkyl;

wherein R⁴ is independently selected from H, and C₁₋₂ alkyl; and wherein R⁶ is one or more substituents independently selected from H, halo, —OR³, —SR³, —CO₂R³, —CONR³R³, —COR³, —NR³R³, —SO₂R³, —SO₂NR³R³, —NR³C(O)OR³, —NR³C(O)R³, —NR³C(O)NR³R³, optionally substituted cycloalkyl, optionally substituted 4-6 membered heterocyclyl, optionally substituted phenyl, cyano, alkylaminoalkoxy and nitro;

and pharmaceutically acceptable derivatives thereof;

provided R¹ is not 5-((2-chloro-6-methylphenyl)-aminocarbonyl)thiazol-2-yl when Y² is NH, W is NH and X is NH; further provided R¹ is not 2-(substituted aminocarbonyl)pyrid-4-yl when Y² is NH; further provided R¹ is not 2-(substituted aminocarbonyl)pyrid-4-yl when Y² is O and when R is phenyl or substituted phenyl.

The invention also relates to compounds of Formula II wherein R is a substituted or unsubstituted ring selected from phenyl, indanyl, tetrahydronaphthyl, naphthyl, cyclohexyl, indazolyl, indolyl, 2,1,3-benzothiadiazolyl, isoxazolyl, pyrazolyl, thiazolyl, thiadiazolyl, thienyl, pyridyl, pyrimidinyl, pyridazinyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, isoindolyl, 2,3-dihydro-1H-indolyl, naphthyridinyl, benzothienyl, benzofuryl, 2,3-dihydro-benzofuryl, benzodioxolyl, benzimidazolyl, benzoxazolyl, benzthiazolyl, isoquinolyl, quinolyl, 1,2,3,4-tetrahydro-isoquinolyl, tetrahydroquinolyl, 2,3,4,4a,9,9a-hexahydro-1H-3-aza-fluorenyl, 5,6,7-trihydro-1,2,4-triazolo[3,4-a]isoquinolyl, benzodioxanyl and quinazolinyl; wherein substituted R is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholin-4-ylmethyl, 4-methylpiperazin-1-ylmethyl, 4-isopropyl-piperazin-1-ylmethyl, 4-methylpiperazin-1-ylpropyl, morpholin-4-ylpropyl, methylpiperidinylmethyl, morpholin-4-ylethyl, 1-(4-morpholinyl)-2,2-dimethylpropyl, piperidinylethyl, piperidinylmethyl, piperidinylpropyl, 4-(dimethylaminoethyl)piperazin-1-ylmethyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, diethylaminoethoxy, 4-chlorophenoxy, phenyloxy, 1-methylpiperdin-4-yloxy, piperdin-4-yloxy, piperidinylethoxy, morpholin-4-ylethyloxy, 4-methylpiperazin-1-ylethoxy, 4-isopropylpiperazinylethoxy, piperdin-4-ylmethoxy, 4-methylpiperdin-1-ylmethoxy, 1-methylpiperdin-4-ylmethoxy, 1-isopropylpiperdin-4-ylmethoxy, 1-methylpyrrolidin-2-ylmethoxy, 1-isopropylpyrrolidin-2-ylmethoxy, 1-isopropylpyrrolidin-3-ylmethoxy, 1-pyrrolidinylmethoxy, 1-pyrrolidinylethoxy, 1-methylpyrrolidin-3-ylmethoxy, 3-(dimethylamino)pyrrolidin-1-ylethoxy, 2-tetrahydrofurylmethoxy, isopropoxy, methoxy and ethoxy; in conjunction with any of the above or below embodiments.

The invention also relates to compounds of Formula II wherein R is

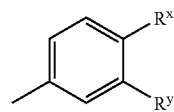

wherein R$^x$ is selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and wherein R$^y$ is selected from H, 4-methylpiperazinylsulfonyl, trifluoromethyl, morpholinylmethyl, 4-methylpiperazinylmethyl, 3-dimethylaminopyrrolidin-1-ylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 1-methylpyrrolidin-2-ylmethyl, dimethylaminoethyl, dimethylaminoethoxy, piperidinylethoxy, morpholinylethyloxy, 4-methylpiperazin-1-ylethoxy, 4-(dimethylaminoethyl)piperazin-1-ylmethyl, 4-isopropylpiperazinylmethoxy, piperdin-4-ylmethoxy, 4-methylpiperdin-1-ylmethoxy, 1-methylpiperdin-4-ylmethoxy, 1-isopropylpiperdin-4-ylmethoxy, 1-pyrrolidinylmethoxy, 1-pyrrolidinylethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-tetrahydrofurylmethoxy, diethylaminoethoxy, 2-(N,N-dimethylamino)acetylamino and 2-(N,N-dimethylamino)ethylamino; in conjunction with any of the above or below embodiments.

The invention also relates to compounds of Formula II wherein R¹ is a substituted or unsubstituted ring selected from 4-pyridyl, triazolyl, 4-pyrimidinyl, 4-pyridazinyl, phenyl, 6-indazolyl, 4-quinolyl, indolyl, isoindolyl, benzotriazolyl, benzo[1,3]dioxolyl, pyrrolo[2,3-d]pyrimidin-4-yl, 2-oxo-1,3-dihydro-pyrrolo[2,3-d]pyridin-4-yl, pyrazolo[2,3-b]pyridin-4-yl, imidazo[4,5-b]pyridin-4-yl, pyrrolo[2,3-b]pyridin-4-yl, 2,3-dihydrobenzofuryl, 2-oxo-1,2-dihydroquinol-7-yl, and 4-quinazolinyl; wherein substituted R¹ is substituted with one or more substituents independently selected from chloro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholinoethoxy, pyrrolidin-1-ylethoxy, 4-methylpiperazin-1-ylethoxy, methylaminocarbonyl, 1-pyrrolidinylbutylaminocarbonyl, dimethylaminoethylamino, dimethylaminopropylamino, methyl, ethyl, propyl, cyano, hydroxymethyl, aminomethyl, aminocarbonyl, nitro, trifluoromethyl, optionally substituted piperidinyl, morpholinyl, optionally substituted piperazinyl, and optionally substituted phenyl; in conjunction with any of the above or below embodiments.

The invention also relates to compounds of Formula II wherein $R^1$ is selected from unsubstituted or substituted 9- or 10-membered fused nitrogen-containing heteroaryl; in conjunction with any of the above or below embodiments.

The invention also relates to compounds of Formula II wherein $R^1$ is a substituted or unsubstituted ring selected from 6-indazolyl, 4-quinolyl, pyrrolo[2,3-d]pyrimidin-4-yl, 2-oxo-1,3-dihydro-pyrrolo[2,3-d]pyridin-4-yl, pyrazolo[2,3,b]pyridin-4-yl, imidazo[4,5-b]pyridin-4-yl, pyrrolo[2,3-b]pyridin-4-yl, 2-oxo-1,2-dihydroquinol-7-yl, and 4-quinazolinyl; in conjunction with any of the above or below embodiments.

The invention also relates to compounds of Formula II wherein $R^1$ is a substituted or unsubstituted pyrrolo[2,3-b]pyridin-4-yl; in conjunction with any of the above or below embodiments.

The invention also relates to compounds of Formula II wherein $R^1$ is a substituted or unsubstituted 4-quinolyl; in conjunction with any of the above or below embodiments.

The invention also relates to compounds of Formula II wherein $R^1$ is a substituted or unsubstituted 4-quinazolinyl; in conjunction with any of the above or below embodiments.

The invention also relates to compounds of Formula II wherein $R^1$ is a substituted or unsubstituted pyrrolo[2,3-d]pyrimidin-4-yl; in conjunction with any of the above or below embodiments.

The invention also relates to compounds of Formula II wherein $R^2$ is H or Cl; in conjunction with any of the above or below embodiments.

The invention also relates to compounds of Formula III

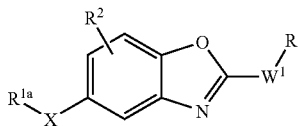

III wherein $W^1$ and X are independently O or NH;
wherein R is selected from
  a) substituted or unsubstituted 6-10 membered aryl,
  b) substituted or unsubstituted 5-6 membered heterocyclyl,
  c) substituted or unsubstituted 9-13 membered fused heterocyclyl, and
  d) substituted or unsubstituted cycloalkyl,
    wherein substituted R is substituted with one or more substituents independently selected from halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, oxo, —$OC(O)R^3$, optionally substituted cycloalkyl, optionally substituted 4-6 membered heterocyclyl, optionally substituted phenyl, cyano, alkylaminoalkoxy, alkylaminoalkoxyalkoxy, nitro and lower alkyl substituted with $R^6$;
wherein $R^{1a}$ is selected from unsubstituted or substituted 9- or 10-membered fused nitrogen-containing heteroaryl, and where substituted $R^1$ is substituted with one or more substituents selected from halo, —$OR^3$, —$SR^3$, —$SO_2R^3$, —$CO_2R^3$, —$C(O)R^3$, —$NR^3R^3$, —$SO_2NR^3R^3$, —$NR^3C(O)OR^3$, —$NR^3C(O)R^3$, optionally substituted 3-6 membered heterocyclyl, optionally substituted phenyl, nitro, cyano, oxo, and lower alkyl substituted with $R^6$;

wherein $R^2$ is one or more substituents independently selected from H, halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, nitro, and lower alkyl substituted with $R^6$;

wherein $R^3$ is independently selected from H, lower alkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl, lower aminoalkyl, lower alkylaminoalkyl and lower haloalkyl;

wherein $R^4$ is independently selected from H, and $C_{1-2}$ alkyl; and wherein $R^6$ is one or more substituents independently selected from H, halo, —$OR^3$, —$SR^3$, —$CO_2R^3$, —$CONR^3R^3$, —$COR^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy and nitro;

and pharmaceutically acceptable derivatives thereof.

The invention also relates to compounds of Formula III wherein R is a substituted or unsubstituted ring selected from phenyl, indanyl, tetrahydronaphthyl, naphthyl, cyclohexyl, indazolyl, indolyl, 2,1,3-benzothiadiazolyl, isoxazolyl, pyrazolyl, thiazolyl, thiadiazolyl, thienyl, pyridyl, pyrimidinyl, pyridazinyl, 2-oxo-1,2-dihydroquinol-7-yl, 1-oxo-1,2,3,4-tetrahydro-isoquinolyl, 2,3-dihydro-1,1-dioxo-benzo[d]isothiazolyl, isoindolyl, 2,3-dihydro-1H-indolyl, naphthyridinyl, benzothienyl, benzofuryl, 2,3-dihydro-benzofuryl, benzodioxolyl, benzimidazolyl, benzoxazolyl, benzthiazolyl, isoquinolyl, quinolyl, 1,2,3,4-tetrahydro-isoquinolyl, tetrahydroquinolyl, 2,3,4,4a,9,9a-hexahydro-1H-3-aza-fluorenyl, 5,6,7-trihydro-1,2,4-triazolo[3,4-a]isoquinolyl, benzodioxanyl and quinazolinyl; wherein substituted R is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholin-4-ylmethyl, 4-methylpiperazin-1-ylmethyl, 4-isopropyl-piperazin-1-ylmethyl, 4-methylpiperazin-1-ylpropyl, morpholin-4-ylpropyl, methylpiperidinylmethyl, morpholin-4-ylethyl, 1-(4-morpholinyl)-2,2-dimethylpropyl, piperidinylethyl, piperidinylmethyl, piperidinylpropyl, 4-(dimethylaminoethyl)piperazin-1-ylmethyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-aminoethyl, 1-(N-isopropylamino)ethyl, 2-(N-isopropylamino)ethyl, dimethylaminopropyl, dimethylaminoethoxy, diethylaminoethoxy, 4-chlorophenoxy, phenyloxy, 1-methylpiperdin-4-yloxy, piperdin-4-yloxy, piperidinylethoxy, morpholin-4-ylethyloxy, 4-methylpiperazin-1-ylethoxy, 4-isopropylpiperazinylethoxy, piperdin-4-ylmethoxy, 4-methylpiperdin-1-ylmethoxy, 1-methylpiperdin-4-ylmethoxy, 1-isopropylpiperdin-4-ylmethoxy, 1-methylpyrrolidin-2-ylmethoxy, 1-isopropylpyrrolidin-2-ylmethoxy, 1-isopropylpyrrolidin-3-ylmethoxy, 1-pyrrolidinylmethoxy, 1-pyrrolidinylethoxy, 1-methylpyrrolidin-3-ylmethoxy, 3-(dimethylamino)pyrrolidin-1-ylethoxy, 2-tetrahydrofurylmethoxy, isopropoxy, methoxy and ethoxy; in conjunction with any of the above or below embodiments.

The invention also relates to compounds of Formula III wherein R is

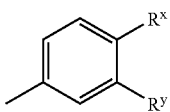

wherein $R^x$ is selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and wherein $R^y$ is selected from H, 4-methylpiperazinylsulfonyl, trifluoromethyl, morpholinylmethyl, 4-methylpiperazinylmethyl, 3-dimethylaminopyrrolidin-1-ylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 1-methylpyrrolidin-2-ylmethyl, dimethylaminoethyl, dimethylaminoethoxy, piperidinylethoxy, morpholinylethyloxy, 4-methylpiperazin-1-ylethoxy, 4-(dimethylaminoethyl)piperazin-1-ylmethyl, 4-isopropylpiperazinylmethoxy, piperdin-4-ylmethoxy, 4-methylpiperdin-1-ylmethoxy, 1-methylpiperdin-4-ylmethoxy, 1-isopropylpiperdin-4-ylmethoxy, 1-pyrrolidinylmethoxy, 1-pyrrolidinylethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-tetrahydrofurylmethoxy, diethylaminoethoxy, 2-(N,N-dimethylamino)acetylamino and 2-(N,N-dimethylamino)ethylamino; in conjunction with any of the above or below embodiments.

The invention also relates to compounds of Formula III wherein $R^{1a}$ is a substituted or unsubstituted ring selected from 6-indazolyl, 4-quinolyl, indolyl, isoindolyl, benzotriazolyl, benzo[1,3]dioxolyl, pyrrolo[2,3-d]pyrimidin-4-yl, 2-oxo-1,3-dihydro-pyrrolo[2,3-d]pyridin-4-yl, pyrazolo[2,3,b]pyridin-4-yl, imidazo[4,5-b]pyridin-4-yl, pyrrolo[2,3-b]pyridin-4-yl, 2,3-dihydrobenzofuryl, 2-oxo-1,2-dihydroquinol-7-yl, and 4-quinazolinyl; wherein substituted $R^1$ is substituted with one or more substituents independently selected from chloro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholinoethoxy, pyrrolidin-1-ylethoxy, 4-methylpiperazin-1-ylethoxy, methylaminocarbonyl, 1-pyrrolidinylbutylaminocarbonyl, dimethylaminoethylamino, dimethylaminopropylamino, methyl, ethyl, propyl, cyano, hydroxymethyl, aminomethyl, aminocarbonyl, nitro, trifluoromethyl, optionally substituted piperidinyl, morpholinyl, optionally substituted piperazinyl, and optionally substituted phenyl; in conjunction with any of the above or below embodiments.

The invention also relates to compounds of Formula III wherein $R^{1a}$ is a substituted or unsubstituted ring selected from 6-indazolyl, 4-quinolyl, pyrrolo[2,3-d]pyrimidin-4-yl, 2-oxo-1,3-dihydro-pyrrolo[2,3-d]pyridin-4-yl, pyrazolo[2,3,b]pyridin-4-yl, imidazo[4,5-b]pyridin-4-yl, pyrrolo[2,3-b]pyridin-4-yl, 2-oxo-1,2-dihydroquinol-7-yl, and 4-quinazolinyl; in conjunction with any of the above or below embodiments.

The invention also relates to compounds of Formula III wherein $R^{1a}$ is a substituted or unsubstituted pyrrolo[2,3-b]pyridin-4-yl; in conjunction with any of the above or below embodiments.

The invention also relates to compounds of Formula III wherein $R^{1a}$ is a substituted or unsubstituted 4-quinolyl; in conjunction with any of the above or below embodiments.

The invention also relates to compounds of Formula III wherein $R^{1a}$ is a substituted or unsubstituted 4-quinazolinyl; in conjunction with any of the above or below embodiments.

The invention also relates to compounds of Formula III wherein $R^{1a}$ is a substituted or unsubstituted pyrrolo[2,3-d]pyrimidin-4-yl; in conjunction with any of the above or below embodiments.

The invention also relates to compounds of Formula III wherein $R^2$ is H or Cl; in conjunction with any of the above or below embodiments.

A family of specific compounds of particular interest within Formula I consists of compounds and pharmaceutically-acceptable derivatives thereof as follows:

(4-Chloro-3-trifluoromethyl-phenyl)-[5-(pyridin-4-yloxy)-1H-benzimidazol-2-yl]-amine;

N-(4-(1,1-Dimethylethyl)-phenyl)-5-(4-pyridinyloxy)-1H-benzimidazol-2-amine;

N-(2-Chloro-4-(1,1-dimethylethyl)phenyl)-5-(4-pyridinyloxy)-1H-benzimidazol-2-amine;

N-(3-Chlorophenyl)-5-(4-pyridinyloxy)-1H-benzimidazol-2-amine;

N-(3-(Methoxy)phenyl)-5-(4-pyridinyloxy)-1H-benzimidazol-2-amine;

N-Phenyl-5-(4-pyridinyloxy)-1H-benzimidazol-2-amine;

5-(4-Pyridinyloxy)-N-(3-(trifluoromethyl)phenyl)-1H-benzimidazol-2-amine;

(4-Fluoro-phenyl)-[5-(pyridin-4-yloxy)-1H-benzimidazol-2-yl]-amine;

(3-Fluoro-phenyl)-[5-(pyridin-4-yloxy)-1H-benzimidazol-2-yl]-amine;

(3,4-Difluoro-phenyl)-[5-(pyridin-4-yloxy)-1H-benzimidazol-2-yl]-amine;

(3-Trifluoromethyl-phenyl)-[5-(pyridin-4-yloxy)-1H-benzimidazol-2-yl]-amine;

N-(3-Chloro-4-fluorophenyl)-5-(4-pyridinyloxy)-1H-benzimidazol-2-amine;

4-[2-(4-Chloro-3-trifluoromethylphenylamino)-1H-benzimidazol-5-yloxy]-pyridine-2-carboxylic acid methylamide;

4-{2-[4-Pentafluoroethyl-3-(2-pyrrolidin-1-yl-ethoxy)-phenylamino]-1H-benzimidazol-5-yloxy}-pyridine-2-carboxylic acid methylamide;

4-{2-[3-(2-Pyrrolidin-1-yl-ethoxy)-5-trifluoromethyl-phenylamino]-1H-benzimidazol-5-yloxy}-pyridine-2-carboxylic acid methylamide;

4-{2-[4-Pentafluoro-3-(pyrrolidin-2-ylmethoxy)-phenylamino]-1H-benzimidazol-5-yloxy}-pyridine-2-carboxylic acid methylamide.

4-{2-[3-(1-Methyl-pyrrolidin-2-ylmethoxy)-4-pentafluoroethyl-phenylamino]-1H-benzimidazol-5-yloxy}-pyridine-2-carboxylic acid methylamide;

4-{2-[3-(2-Dimethylamino-ethyl)-4-methoxy-phenylamino]-1H-benzimidazol-5-yloxy}-pyridine-2-carboxylic acid methylamide;
4-{2-[3-Difluoromethoxy-4-(4-isopropyl-piperazin-1-yl)-phenylamino]-1H-benzimidazol-5-yloxy}-pyridine-2-carboxylic acid methylamide;
4-{2-[4-tert-Butyl-3-(2-dimethylamino-acetylamino)-phenylamino]-1H-benzimidazol-5-yloxy}-pyridine-2-carboxylic acid methylamide;
4-(2-{4-[1-Methyl-1-(1-methyl-piperidin-4-yl)-ethyl]-phenylamino}-1H-benzimidazol-5-yloxy)-pyridine-2-carboxylic acid methylamide;
2-tert-Butoxycarbonly-4,4-dimethyl-7-[5-(2-methylcarbamoyl-pyridin-4-yloxy)-1H-benzimidazol-2-ylamino]-3,4-dihydro-1H-isoquinoline;
4-[2-(4,4-Dimethyl-1,2,3,4-tetrahydro-isoquinolin-7-ylamino)-1H-benzimidazol-5-yloxy]-pyridine-2-carboxylic acid methylamide;
4-[2-(4-Chloro-3-piperazin-1-ylmethyl-phenylamino)-1H-benzimidazol-5-yloxy]-pyridine-2-carboxylic acid methylamide;
4-{2-[3-(2-Dimethylamino-ethoxy)-4-trifluoromethyl-phenylamino]-1H-benzimidazol-5-yloxy}-pyridine-2-carboxylic acid methylamide;
4-{2-[4-Chloro-3-(4-methyl-piperazin-1-ylmethyl)-phenylamino]-1H-benzimidazol-5-yloxy}-pyridine-2-carboxylic acid methylamide;
4-{2-[4-Chloro-3-(4-isopropyl-piperazin-1-ylmethyl)-phenylamino]-1H-benzimidazol-5-yloxy}-pyridine-2-carboxylic acid methylamide;
4-{2-[4-Chloro-3-(4-methanesulfonyl-piperazin-1-ylmethyl)-phenylamino]-1H-benzimidazol-5-yloxy}-pyridine-2-carboxylic acid methylamide;
4-{2-[3-(1-Methyl-pyrrolidin-2-ylmethoxy)-4-trifluoromethyl-phenylamino]-1H-benzimidazol-5-yloxy}-pyridine-2-carboxylic acid methylamide;
3-{2-[4-Chloro-3-(4-methyl-piperazin-1-ylmethyl)-phenylamino]-1H-benzimidazol-5-yloxy}-N-methyl-benzamide;
N-(3-{2-[4-Chloro-3-(4-methyl-piperazin-1-ylmethyl)-phenylamino]-1H-benzimidazol-5-yloxy}-phenyl)-acetamide;
4-[2-(4-Chloro-3-trifluoromethyl-phenylamino)-6-methyl-1H-benzimidazol-5-yloxy]-pyridine-2-carboxylic acid methylamide;
4-{2-[4-Chloro-3-(4-methyl-piperazin-1-ylmethyl)-phenylamino]-1-methyl-1H-benzimidazol-5-yloxy}-pyridine-2-carboxylic acid methylamide;
[4-Chloro-3-(4-methyl-piperazin-1-ylmethyl)-phenyl]-[5-(2-methylsulfanyl-pyrimidin-4-yloxy)-1H-benzimidazol-2-yl]-amine;
(4-Chloro-3-trifluoromethyl-phenyl)-[5-(2-methylamino-pyrimidin-4-yloxy)-1H-benzimidazol-2-yl]-amine;
[4-chloro-3-(4-methylpiperazin-1-ylmethyl)-phenyl]-[5-(2-methylamino-pyrimidin-4-yloxy)-1H-benzimidazol-2-yl]-amine;
(4-Chloro-3-trifluoromethylphenyl)-[5-(2-(2-N,N-dimethylaminoethylamin)pyrimidin-4-yloxy)-1H-benzimidazol-2-yl]-amine;
(4-Chloro-3-trifluoromethylphenyl)-{6-[2-(3-pyrrolidin-1-yl-propylamino)pyrimidin-4-yloxy]-1H-benzimidazol-2-yl}-amine;
(4-Chloro-3-trifluoromethylphenyl)-[6-(1H-pyrrolo[2,3-b]pyridin-4-yloxy)-1H-benzimidazol-2-yl]-amine;
[4-Chloro-3-(4-methyl-piperazin-1-ylmethyl)-phenyl]-[6-(1H-pyrrolo[2,3-b]pyridin-4-yloxy)-1H-benzimidazol-2-yl]-amine;
(4-tert-Butyl-phenyl)-[5-(quinolin-4-yloxy)-1H-benzimidazol-2-yl]-amine;
[5-(Quinolin-4-yloxy)-1H-benzimidazol-2-yl]-(4-trifluoromethyl-phenyl)-amine;
[4-Chloro-3-(4-methyl-piperazin-1-ylmethyl)-phenyl]-[6-(7H-pyrrolo[2,3-d]pyrimidin-4-yloxy)-1H-benzimidazol-2-yl]-amine;
[3-(1-Methyl-pyrrolidin-2-ylmethoxy)-4-trifluoromethyl-phenyl]-[5-(quinolin-4-yloxy)-1H-benzimidazol-2-yl]-amine;
[4-Chloro-3-(4-methyl-piperazin-1-ylmethyl)-phenyl]-[5-(quinolin-4-yloxy)-1H-benzimidazol-2-yl]-amine;
[4-Chloro-3-(4-methyl-piperazin-1-ylmethyl)-phenyl]-[5-(2-methylamino-pyridin-4-yloxy)-benzoxazol-2-yl]-amine;
[4-Chloro-3-(4-methyl-piperazin-1-ylmethyl)-phenyl]-[5-(6-methylamino-pyrimidin-4-yloxy)-benzoxazol-2-yl]-amine;
4-{2-[4-Chloro-3-(4-methyl-piperazin-1-ylmethyl)-phenylamino]-benzoxazol-5-yloxy}-pyridine-2-carboxylic acid methylamide;
4-[2-(4-Chloro-3-pyrrolidin-1-ylmethyl-phenylamino)-benzoxazol-5-yloxy]-pyridine-2-carboxylic acid methylamide;
4-[2-(4-Chloro-3-morpholin-4-ylmethyl-phenylamino)-benzoxazol-5-yloxy]-pyridine-2-carboxylic acid methylamide;
4-{2-[4-Chloro-3-(1-methyl-pyrrolidin-2-ylmethoxy)-phenylamino]-benzoxazol-5-yloxy}-pyridine-2-carboxylic acid methylamide;
4-[2-(Isoquinolin-3-ylamino)-benzoxazol-5-yloxy]-pyridine-2-carboxylic acid methylamide;
([4-Chloro-3-(4-methyl-piperazin-1-ylmethyl)-phenyl]-[5-(quinolin-4-yloxy)-benzoxazol-2-yl]-amine);
[3-(1-Methyl-pyrrolidin-2-ylmethoxy)-4-trifluoromethyl-phenyl]-[5-(quinolin-4-yloxy)-benzoxazol-2-yl]-amine;
[4-Chloro-3-(1-methyl-pyrrolidin-2-ylmethoxy)-phenyl]-[5-(quinolin-4-yloxy)-benzoxazol-2-yl]-amine;
4-((2-((4-Chlorophenyl)amino)-1,3-benzoxazol-5-yl)oxy)-N-methyl-2-pyridinecarboxamide;
4-((2-((4-Bromophenyl)amino)-1,3-benzoxazol-5-yl)oxy)-N-methyl-2-pyridinecarboxamide;
N-Methyl-4-((2-((4-(1-methylethyl)phenyl)amino)-1,3-benzoxazol-5-yl)oxy)-2-pyridinecarboxamide;
$N^5$-(4-Quinolinyl)-$N^2$-(4-(trifluoromethyl)phenyl)-1,3-benzoxazole-2,5-diamine;
$N^2$-(4-Chloro-3-((((2S)-1-methyl-2-pyrrolidinyl)methyl)oxy)phenyl)-$N^5$-(4-quinolinyl)-1,3-benzoxazole-2,5-diamine;
5-((6,7-bis(Methoxy)-4-quinolinyl)oxy)-N-(4-chloro-3-((4-methyl-1-piperazinyl)methyl)phenyl)-1,3-benzoxazol-2-amine;
N-(4-Chloro-3-((4-methyl-1-piperazinyl)methyl)phenyl)-5-(1H-pyrrolo[2,3-b]pyridin-4-yloxy)-1,3-benzoxazol-2-amine;
N-(4-Chloro-3-((((2S)-1-methyl-2-pyrrolidinyl)methyl)oxy)phenyl)-5-(1H-pyrrolo[2,3-b]pyridin-4-yloxy)-1,3-benzoxazol-2-amine;
N-Butyl-5-(4-quinolinyloxy)-1,3-benzoxazol-2-amine;
4-((2-((4-Chloro-3-((((2S)-1-methyl-2-pyrrolidinyl)methyl)oxy)phenyl)amino)-7-fluoro-1,3-benzoxazol-5-yl)oxy)-N-methyl-2-pyridinecarboxamide; and
N-(4-Chloro-3-((2-(methoxy)ethyl)oxy)phenyl)-5-(4-quinolinyloxy)-1,3-benzoxazol-2-amine.

Another family of specific compounds of particular interest within Formula I consists of compounds and pharmaceutically-acceptable derivatives thereof as follows:

[4-Chloro-3-(4-methyl-piperazin-1-ylmethyl)-phenyl]-[5-(6,7-dimethoxy-quinolin-4-yloxy)-1H-benzoimidazol-2-yl]-amine;

[4-Chloro-3-(1-methyl-piperidin-4-ylmethoxy)-phenyl]-[5-(6,7-dimethoxy-quinazolin-4-yloxy)-1H-benzoimidazol-2-yl]-amine;

[4-Chloro-3-((2S)-1-methyl-pyrrolidin-2-ylmethoxy)-phenyl]-[5-(2-methyl-amino-pyridin-4-yloxy)-benzooxazol-2-yl]-amine;

4-{2-[4-Chloro-3-((2S)-1-methyl-pyrrolidin-2-ylmethoxy)-phenylamino]-benzooxazol-5-yloxy}-pyridine-2-carboxylic acid amide;

4-{2-[4-Chloro-3-(2-pyrrolidin-1-yl-ethoxy)-phenylamino]-benzooxazol-5-yloxy}-pyridine-2-carboxylic acid amide;

4-{2-[4-Chloro-3-(1-methyl-piperidin-4-ylmethoxy)-phenylamino]-benzooxazol-5-yloxy}-pyridine-2-carboxylic acid methylamide;

4-{2-[4-Chloro-3-(piperidin-4-ylmethoxy)-phenylamino]-benzooxazol-5-yloxy}-pyridine-2-carboxylic acid methylamide;

4-{2-[4-Chloro-3-(1-isopropyl-piperidin-4-ylmethoxy)-phenylamino]-benzooxazol-5-yloxy}-pyridine-2-carboxylic acid methylamide;

4-{7-Chloro-2-[4-chloro-3-(4-methyl-piperazin-1-ylmethyl)-phenylamino]-benzooxazol-5-yloxy}-pyridine-2-carboxylic acid methylamide;

4-[2-{4-Chloro-3-[4-(2-dimethylamino-ethyl)-piperazin-1-ylmethyl]-phenylamino}-benzooxazol-5-yloxy)-pyridine-2-carboxylic acid methylamide;

4-{2-[4-Chloro-3-(2-diethylamino-ethoxy)-phenylamino]-benzooxazol-5-yloxy}-pyridine-2-carboxylic acid methylamine;

4-{2-[4-Chloro-3-(2-dimethylamino-ethoxy)-phenylamino]-benzooxazol-5-yloxy}-pyridine-2-carboxylic acid methylamide;

4-(2-{4-Chloro-3-[2-(3-dimethylamino-pyrrolidin-1-yl)-ethoxy]-phenylamino}-benzooxazol-5-yloxy)-pyridine-2-carboxylic acid methylamide;

4-(2-{4-Chloro-3-[2-(4-methyl-piperazin-1-yl)-ethoxy]-phenylamino]-benzooxazol-5-yloxy)-pyridine-2-carboxylic acid methylamide;

4-{2-[4-Chloro-3-(tetrahydro-furan-2-ylmethoxy)-phenylamino]-benzooxazol-5-yloxy}-pyridine-2-carboxylic acid (4-pyrrolidin-1-yl-butyl)-amide;

4-[2-(4-Chloro-phenylamino)-benzooxazol-5-yloxy]-pyridine-2-carboxylic acid (4-pyrrolidin-1-yl-butyl)-amide;

4-[2-(4-Chloro-3-trifluoromethyl-phenylamino)-benzooxazol-5-yloxy]-pyridine-2-carboxylic acid (4-pyrrolidin-1-yl-butyl)-amide;

[5-(quinolin-4-yloxy)-benzooxazol-2-yl]-(4-trifluoromethoxy-phenyl)-amine;

[4-Chloro-3-(4-methyl-piperazin-1-ylmethyl)-phenyl]-[7-chloro-5-(quinolin-4-yloxy)-benzooxazol-2-yl]-amine;

(4-Chloro-phenyl)-[5-(6,7-dimethoxy-quinolin-4-yloxy)-benzooxazol-2-yl]-amine;

[4-Chloro-3-(1-methyl-pyrrolidin-2-ylmethoxy)-phenyl]-[5-(6,7-dimethoxy-quinolin-4-yloxy)-benzooxazol-2-yl]-amine;

Cyclohexyl-[5-(6,7-dimethoxy-quinolin-4-yloxy)-benzooxazol-2-yl]-amine;

[5-(6,7-Dimethoxy-quinazolin-4-yloxy)-benzooxazol-2-yl]-[3-(1-methyl-pyrrolidin-2-ylmethoxy)-5-trifluoromethyl-phenyl]-amine;

[4-Chloro-3-(4-methyl-piperazin-1-ylmethyl)-phenyl]-[5-(6,7-dimethoxy-quinazolin-4-yloxy)-benzooxazol-2-yl]-amine;

[4-Chloro-3-(1-methyl-pyrrolidin-2-ylmethoxy)-phenyl]-[5-(6,7-dimethoxy-quinazolin-4-yloxy)-benzooxazol-2-yl]-amine;

[4-Chloro-3-(3-dimethylamino-pyrrolidin-1-ylmethyl)-phenyl]-[5-(1H-pyrrolo[2,3-b]pyridin-4-yloxy)-benzooxazol-2-yl]-amine;

[4-chloro-3-(1-isopropyl-pyrrolidin-2-ylmethoxy)-phenyl]-[5-(1H-pyrrolo[2,3-b]pyridin-4-yloxy)-benzooxazol-2-yl]-amine;

[4-Chloro-3-(1-methyl-piperidin-4-ylmethoxy)-phenyl]-[5-(1H-pyrrolo[2,3-b]pyridin-4-yloxy)-benzooxazol-2-yl]-amine;

[5-(1H-Pyrrolo[2,3-b]pyridin-4-yloxy)-benzooxazol-2-yl]-(5-trifluoromethyl-pyridin-2-yl)-amine; and (4-Chloro-phenyl)-[5-(6,7-dimethoxy-quinazolin-4-yloxy)-1H-benzoimidazol-2-yl]-amine.

Indications

Compounds of the present invention would be useful for, but not limited to, the prevention or treatment of angiogenesis related diseases. The compounds of the invention have kinase inhibitory activity, such as VEGFR/KDR inhibitory activity. The compounds of the invention are useful in therapy as antineoplasia agents or to minimize deleterious effects of VEGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, be consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of this invention may also act as inhibitors of other protein kinases, e.g. tie-2, lck, src, fgf, cmet, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Definitions

The term "treatment" includes therapeutic treatment as well as prophylactic treatment (either preventing the onset of disorders altogether or delaying the onset of a preclinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$)

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "heterocyclylalkylenyl" embraces heterocyclic-substituted alkyl radicals. More preferred heterocyclylalkylenyl radicals are "5- or 6-membered heteroarylalkylenyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—)

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The arylamino radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-C$_1$-C$_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethylaminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open-ended, including the indicated component but not excluding other elements.

The term "Formulas I-III" includes any sub formulas.

The compounds of the invention are endowed with kinase inhibitory activity, such as KDR inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of KDR.

The present invention comprises a pharmaceutical composition comprising a therapeutically-effective amount of a compound of Formulas I-III in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula I'

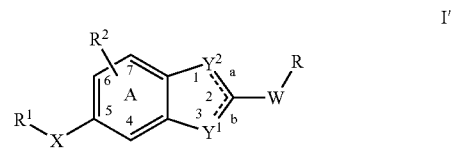

I' wherein W and X are independently selected from O, $S(O)_n$ and wherein Y and Y are independently selected from O, $S(O)_n$, N and $NR^4$;

wherein ring A optionally contains a nitrogen atom independently at position 4, 6 or 7;

wherein n is 0, 1 or 2;

wherein R is selected from
 a) substituted or unsubstituted 6-10 membered aryl,
 b) substituted or unsubstituted 5-6 membered heterocyclyl,
 c) substituted or unsubstituted 9-14 membered fused heterocyclyl,
 d) substituted or unsubstituted cycloalkyl,
 e) substituted or unsubstituted cycloalkenyl, and
 f) alkyl;
  wherein substituted R is substituted with one or more substituents independently selected from halo, —$OR^3$, —SR, —$CO_2R^3$, —$C(O)NR^3R^3$, —$C(O)R^3$, —$NR^3R^3$, oxo, —$OC(O)R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, alkylaminoalkoxyalkoxy, nitro, and lower alkyl substituted with $R^5$;

wherein $R^1$ is selected from
 a) substituted or unsubstituted 6-10 membered aryl,
 b) substituted or unsubstituted 4-6 membered heterocyclyl,
 c) substituted or unsubstituted 9-14 membered fused heterocyclyl,
 d) substituted or unsubstituted arylalkyl, and
 e) substituted or unsubstituted heterocyclylalkyl,
  where substituted $R^1$ is substituted with one or more substituents selected from halo, —$OR^3$, —$SR^3$, —$SO_2R^3$, —$CO_2R^3$, —$C(O)NR^3R^3$, —$C(O)R^3$—$NR^3R^3$, —$SO_2NR^3R^3$, —$NR^3C(O)OR^3$, —$NR^3C(O)R^3$, optionally substituted 3-6 membered heterocyclyl, optionally substituted phenyl, alkylaminoalkoxyalkoxy, nitro, cyano, oxo, lower alkyl substituted with $R^5$;

wherein $R^2$ is one or more substituents independently selected from H, halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —NR³C(O)OR³, —NR³C(O)R³, —NR³C(O)NR³R³, optionally substituted cycloalkyl, optionally substituted 4-6 membered heterocyclyl, optionally substituted phenyl, cyano, alkylaminoalkoxy, alkylaminoalkoxyalkoxy, nitro, lower alkyl substituted with R⁵, lower alkenyl substituted with R⁵, and lower alkynyl substituted with R⁵;

wherein R³ is independently selected from H, lower alkyl, lower aminoalkyl, lower alkylaminoalkyl, optionally substituted phenyl, optionally substituted 3-6 membered heterocyclyl, optionally substituted C₃-C₆-cycloalkyl, optionally substituted phenylalkyl, optionally substituted 3-6 membered heterocyclylalkyl, optionally substituted C₃-C₆ cycloalkylalkyl, and lower haloalkyl;

wherein R⁴ is independently selected from H, and lower alkyl; and wherein R⁵ is one or more substituents independently selected from H, halo, —OR³, —SR³, —CO₂R³, —C(O)NR³R³, —C(O)R³, —NR³R³, —SO₂R³, —SO₂NR³R³, —NR³C(O)OR³, —NR³C(O)R³, —NR³C(O)NR³R³, optionally substituted cycloalkyl, optionally substituted 4-6 membered heterocyclyl, optionally substituted phenyl, cyano, alkylaminoalkoxy, alkylaminoalkoxyalkoxy, nitro, lower alkyl, lower alkenyl and lower alkynyl;

and pharmaceutically acceptable derivatives thereof; provided one of Y¹ and Y² is N or NH; and further provided only one of dashed lines a and b indicates a double bond.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011; Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)₂, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The present invention comprises processes for the preparation of a compound of Formula I-III. Also included in the family of compounds of Formula I-III are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-III may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, nicotinic, 2-hydroxy-ethanesulfonic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-III include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases. Preferred salts include hydrochloride, phosphate and edisylate.

Additional examples of such salts can be found in Berge et al., J. Pharm. Sci., 66:1 (1977).

General Synthetic Procedures

The compounds of the invention can be synthesized according to the following procedures of Schemes 1-10 wherein the substituents are as defined for Formulas I-III, above, except where further noted.

The following abbreviations are used:

| | |
|---|---|
| AcOH, HOAc | acetic acid |
| $(CH_3)_2C=O$ | acetone |
| Atm. | atmosphere |
| $CH_3CN$ | acetonitrile |
| ATP | adenosine triphosphate |
| $NH_4Cl$ | ammonium chloride |
| $NH_4OH$ | ammonium hydroxide |
| BINAP | 2,2'-bis(diphenylphosphino)-1,1'binaphthyl |
| $BH_3$ | borane |
| BSA | bovine serum albumin |
| DDQ | 2,3-dichloro-5,6-dicyano-1,4-benzoquinone |
| $CH_2Cl_2$ | dichloromethane |
| DEA | diethylamine |
| DIEA | diisopropylethylamine |
| DIAD | diisopropyl azodicarboxylate |
| EDC | 1-(3-dimethylaminopropyl)-3-ethylcarbodiimide hydrochloride |
| DMF | dimethylformamide |
| DMSO | dimethyl sulfoxide |
| DPPA | diphenylphosporyl azide |
| DMAP | dimethylaminopyridine |
| DEAD | diethylazidocarboxylate |
| DTT | dithiothreitol |
| EtOH | ethanol |
| EtOAc | ethyl acetate |
| $Et_2O$ | ethyl ether |
| $FeSO_4$ | ferric sulfate |
| g | gram |
| h | hour |
| HBr | hydrobromic acid |
| HCl | hydrochloric acid |
| $H_2$ | hydrogen |
| HOBt | hydroxybenzotriazole |
| Fe | iron |

| | |
|---|---|
| IPA, iPrOH | isopropanol |
| L | liter |
| LAH | lithium aluminum hydride |
| LDA | lithium diisopropylamide |
| LiOH | lithium hydroxide |
| m-CPBA | m-chloroperbenzoic acid |
| $MgSO_4$ | magnesium sulfate |
| $MnCl_2$ | manganese chloride |
| MeOH | methanol |
| MeI | methyl iodide |
| $CH_3NH_2$ | methylamine |
| $HNO_3$ | nitric acid |
| mg | milligram |
| mL | milliliter |
| min | minutes |
| $N_2$ | nitrogen |
| Pd/C | palladium on carbon |
| $Pd(OAc)_2$ | palladium acetate |
| $Pd(PPh_3)_4$ | palladium tetrakis triphenylphosphine |
| $Pd_2(dba)_3$ | tris(dibenzylideneacetone)di-palladium |
| $POCl_3$ | phosphoryl chloride |
| $PCl_5$ | phosphorous pentachloride |
| $P_2O_5$ | phosphorous pentoxide |
| PSI | pounds per square inch |
| Pt/C | platinum on carbon |
| $K_2CO_3$ | potassium carbonate |
| $KNO_3$ | potassium nitrate |
| KOt-Bu | potassium t-butoxide |
| RT | Room temperature |
| $SiO_2$ | silica |
| NaOAc | sodium acetate |
| $NaHCO_3$ | sodium bicarbonate |
| $NaBH_4$ | sodium borohydride |
| $Na_2CO_3$ | sodium carbonate |
| NaCl | sodium chloride |
| NaCN | sodium cyanide |
| $NaCNBH_3$ | sodium cyanoborohydride |
| NaH | sodium hydride |
| NaOH | sodium hydroxide |
| NaOMe | sodium methoxide |
| $Na_2SO_4$ | sodium sulfate |
| $Na_2S_2O_3$ | sodium thiosulphate |
| NaOt-Bu | sodium t-butoxide |
| $NaNO_3$ | sodium nitrate |
| $NaHB(OAc)_3$ | sodium triacetoxyborohydride |
| $Na(AcO)_3BH$ | sodium triacetoxyborohydride |
| $H_2SO_4$ | sulfuric acid |
| $Bu_4NBr$ | tetrabutyl ammonium bromide |
| $Bu_4NI$ | tetrabutyl ammonium iodide |
| t-BuOH | tert-butyl alcohol |
| t-BuOMe, MTBE | tert-butylmethylether |
| Boc | tert-butyloxycarbonyl |
| THF | tetrahydrofuran |
| $SOCl_2$ | thionyl chloride |
| $SnCl_2$ | tin(II)chloride |
| TEA, $Et_3N$ | triethylamine |
| TFA | trifluoroacetic acid |
| $PPh_3$ | triphenylphosphine |
| $H_2O$ | water |

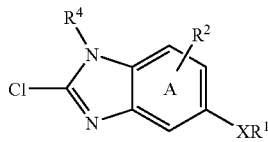

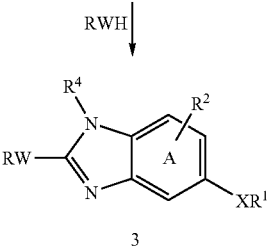

Substituted benzimidazoles can be prepared by the process outlined in Scheme 1. An benzimidazol-2-one can be prepared by the method described in J. Het., 2561 (1999) from the diamine 1. Treatment with $POCl_3$ provides the 2-chloro compound 2, which can be substituted with a variety of compounds to form the benzimidazoles 3 of the present invention.

Scheme 2

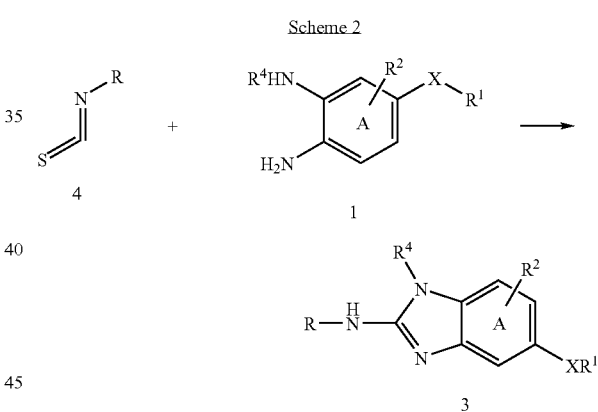

Alternatively, substituted benzimidazoles 3 (where W is NH) can be prepared by the process outlined in Scheme 2. Diamine 1 is reacted with a substituted isothiocyanate 4, in an appropriate solvent such as $CH_3CN$, at a temperature of about RT. Addition of an amine coupling reagent, such as EDC, at a temperature above about 50° C., and preferably at about 80° C., forms the benzimidazoles 3.

Scheme 1

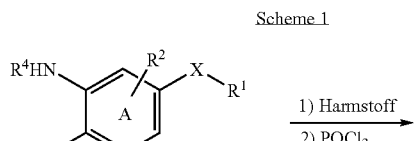

Scheme 3

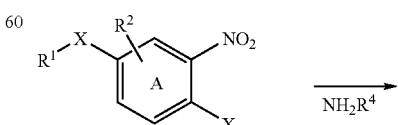

-continued

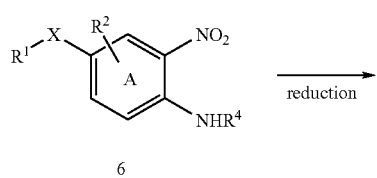

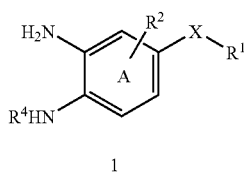

Substituted amines can be prepared by the process outlined in Scheme 3. Substituted amines 6 can be prepared similar to that described in WO 03/006438. Reduction of the nitro substituted compound 6, such as with Pd/C and hydrogen, in the presence of an alcohol, such as EtOH, at a temperature about RT, provides the diamine 1.

Scheme 4

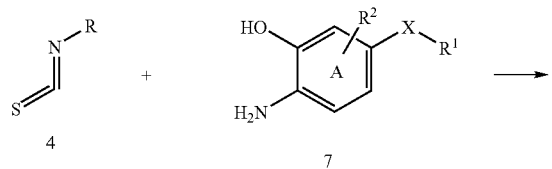

-continued

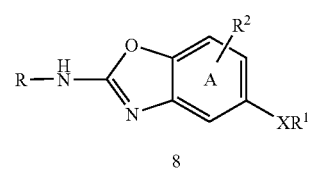

Substituted benzoxazoles can be prepared by the process outlined in Scheme 4. 1-Amino-2-hydroxy aromatic compounds 7 are reacted with a substituted isothiocyanate 4, in an appropriate solvent such as $CH_3CN$, at a temperature of about RT. Addition of an amine coupling reagent, such as EDC, at a temperature above about 50° C., and preferably at about 80° C., forms the benzoxazoles 8.

Scheme 5

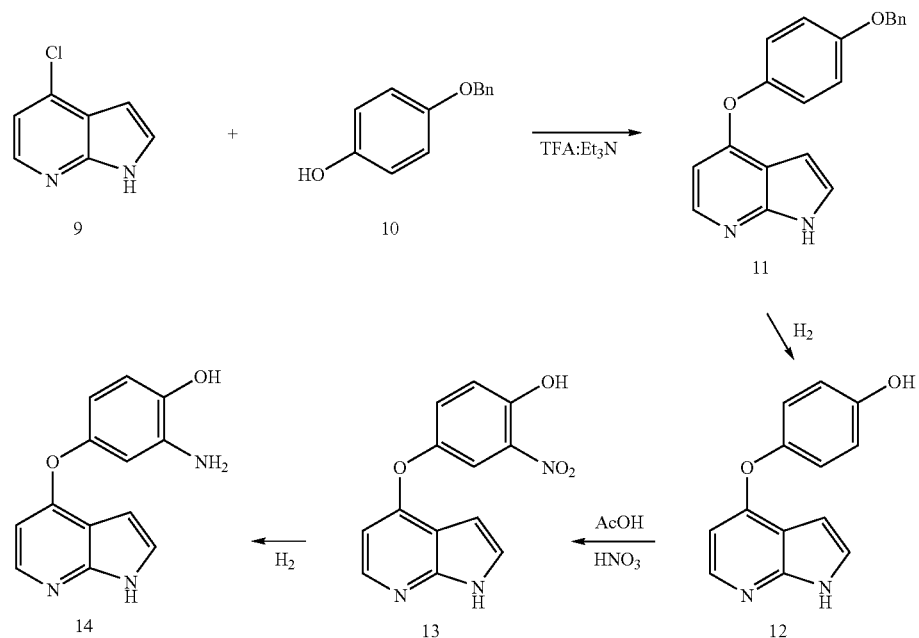

Azaindole phenol ethers can be prepared by the process outlined in Scheme 5. Halo substituted azaindoles 9 can be coupled with phenols and the like 10, such as in the presence of TFA:Et₃N, at a temperature above about 50° C., preferably above about 100° C., and more preferably at about 150° C., to form the protected ether 11. Removal of any protecting groups, such as by hydrogenation in the presence of a catalyst, such as Pd/C, and nitration, such as with $HNO_3$ in the presence of AcOH, provides the nitrophenols 13. Reduction of the nitro substituted compound 13, such as with hydrogenation in the presence of a catalyst, such as Pd/C, provides the amino substituted azaindole phenol ethers 14.

Scheme 6

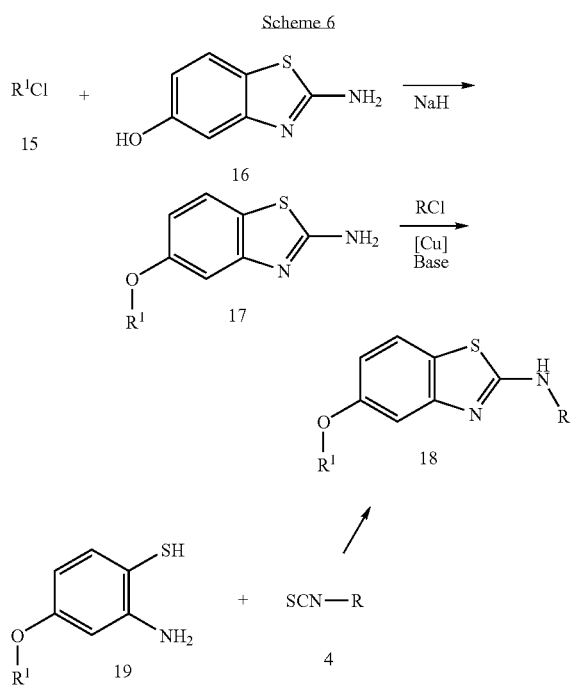

Substituted benzothiazoles can be prepared by the process outlined in Scheme 6. 2-Amino-5-hydroxy benzothiazoles 16 are reacted with a halo compound 15 to form the 2-aminobenzothiazole ether 17. Further substitution such as with substituted halides yields the disubstituted benzothiazole 18. Alternatively, substituted isothiocyanate 4 are reacted with 1-amino-2-thio compounds 19 in an appropriate solvent such as CH$_3$CN, at a temperature of about RT. Addition of an amine coupling reagent, such as EDC, at a temperature above about 50° C., and preferably at about 80° C., forms the benzothiazoles 18.

Scheme 7

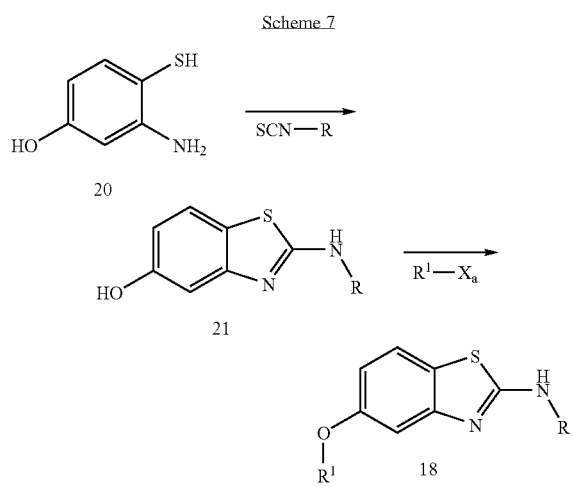

Alternatively substituted benzothiazoles can be prepared by the process outlined in Scheme 7. Substituted isothiocyanate are reacted with 1-amino-2-thio compounds 20 in an appropriate solvent such as CH$_3$CN, at a temperature of about RT. Addition of an amine coupling reagent, such as EDC, at a temperature above about 50° C., and preferably at about 80° C., forms the benzothiazoles 21. The 5-hydroxy benzothiazole 21 is reacted with a halo compound to form the 2-aminobenzothiazole ether 18.

Scheme 8

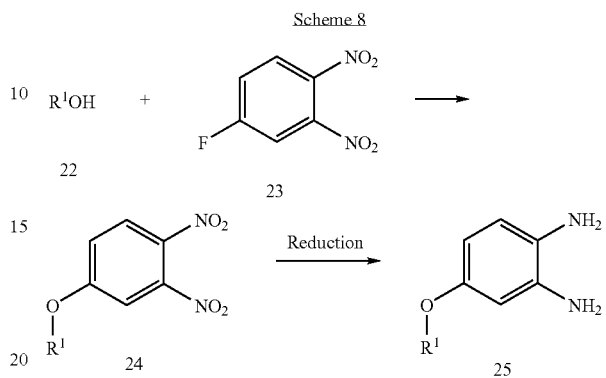

3,4-Diaminophenyl ethers 25 are prepared by the method described in Scheme 8. 3,4-Dinitrophenyl ethers 24 are formed by coupling alcohols 22 with 1-fluoro-3,4-dinitrobenzenes 23, in an appropriate solvent such as anhydrous DMF, and in the presence of base, such as K$_2$CO$_3$, and at a temperature above about 50° C., preferably above about 100° C., more preferably at about 120° C. Reduction of the nitro substituted compound 24, such as with hydrogenation in the presence of an alcohol, such as MeOH, in the presence of a catalyst, such as Pd/C, provides the diamine 25. Reduction by Zn, in the presence of acid, such as HOAc also produces the di-amine. Alternatively, alcohol 22 can be coupled with 4-chloro-2-nitroanilines to form the nitroaniline ethers, which can be reacted as described above to form the 3,4-diaminophenyl ethers 25.

Scheme 9

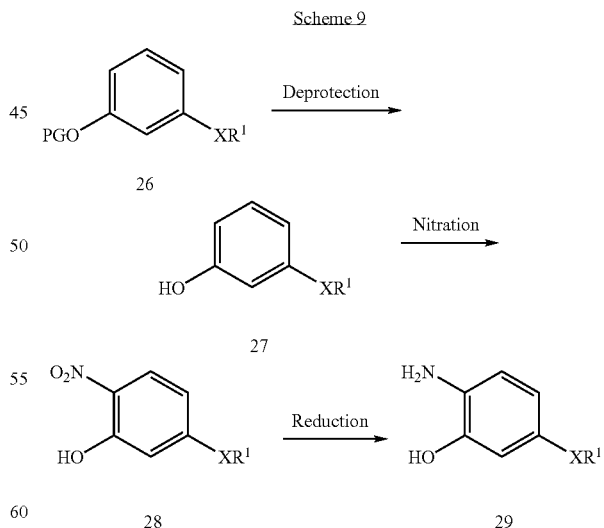

2-Hydroxyanilines 29 are prepared by the method described in Scheme 9. Protected phenols 26 (were PG is a protecting group) are deprotected then nitrated to form the nitrophenols 28. The nitrophenols 28 are reduced to from the anilines 29.

Scheme 10

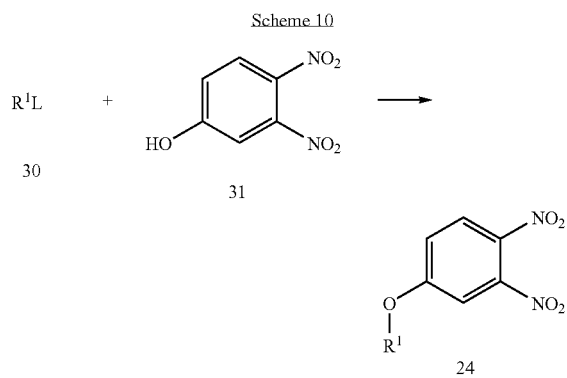

3,4-Dinitrophenyl ethers 24 are prepared by the method described in Scheme 10. 3,4-Dinitrophenyl ethers 24 are formed by coupling compounds 30 where L is a leaving group such as halo, preferably chloro, with 3,4-dinitrophenols 31, at a temperature above about 50° C., preferably above about 100° C., more preferably at about 150° C.

The starting compounds defined in Schemes 1-10 may also be present with functional groups in protected form if necessary and/or in the form of salts, provided a salt-forming group is present and the reaction in salt form is possible. If so desired, one compound of Formula I can be converted into another compound of Formula I or a N-oxide thereof; a compound of Formula I can be converted into a salt; a salt of a compound of Formula I can be converted into the free compound or another salt; and/or a mixture of isomeric compounds of Formula I can be separated into the individual isomers.

N-Oxides can be obtained in a known matter by reacting a compound of formula I with hydrogen peroxide, oxone, or a peracid, e.g. 3-chloroperoxy-benzoic acid, in an inert solvent, e.g. dichloromethane, or a mixture of water and an alcohol such as MeOH or EtOH, at a temperature between about −10-35° C., such as about 0° C.-RT.

If one or more other functional groups, for example carboxy, hydroxy, amino, or mercapto, are or need to be protected in a compound of Formula I or in the preparation of compounds of Formula I, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York (1973), in T. W. Greene, "Protective Groups in Organic Synthesis", Wiley, New York (1981), in "The Peptides", Volume 3 (editors: E. Gross and J. Meienhofer), Academic Press, London and New York (1981), in "Methoden der Organischen Chemie" (Methods of Organic Chemistry), Houben Weyl, 4$^{th}$ edition, Volume 15/1, Georg Thieme Verlag, Stuttgart (1974), in H.-D. Jakubke and H. Jescheit, "Aminosäuren, Peptide, Proteine" (Amino Acids, Peptides, Proteins), Verlag Chemie, Weinheim, Deerfield Beach, and Basel (1982), and in Jochen Lehmann, "Chemie der Kohlenhydrate: Monosaccharide und Derivate" (Chemistry of Carbohydrates: Monosaccharides and Derivatives), Georg Thieme Verlag, Stuttgart (1974).

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of Formula I with a salt-forming group may be prepared in a manner known per se. Acid addition salts of compounds of Formula I may thus be obtained by treatment with an acid or with a suitable anion exchange reagent. A salt with two acid molecules (for example a dihalogenide of a compound of Formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of Formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g., EtOAc, ethers, typically aliphatic ethers, e.g., Et$_2$O, or cyclic ethers, e.g., THF, liquid aromatic hydrocarbons, typically benzene or iPrOH toluene, alcohols, typically MeOH, EtOH or 1-propanol, nitriles, typically CH$_3$CN, halogenated hydrocarbons, typically CH$_2$Cl$_2$, acid amides, typically DMF, bases, typically heterocyclic nitrogen bases, e.g. pyridine, carboxylic acids, typically lower alkanecarboxylic acids, e.g., AcOH, carboxylic acid anhydrides, typically lower alkane acid anhydrides, e.g., acetic anhydride, cyclic, linear, or branched hydrocarbons, typically cyclohexane, hexane, or isopentane, or mixtures of these solvents, e.g., aqueous solutions, unless otherwise stated in the description of the process. Such solvent mixtures may also be used in processing, for example in chromatography.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

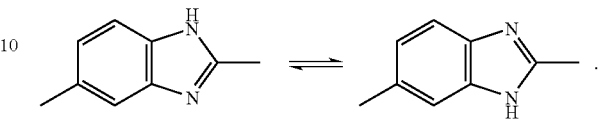

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ Ed. (2001); M. Bodanszky, A. Bodanszky: The Practice of Peptide Synthesis Springer-Verlag, Berlin Heidelberg (1984); J. Seyden-Penne: Reductions by the Alumino- and Borohydrides in Organic Synthesis, 2$^{nd}$ Ed., Wiley-VCH, (1997); and L. Paquette, editor, Encyclopedia of Reagents for Organic Synthesis, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formula I.

These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. Anhydrous solvents such as DMF, THF, $CH_2Cl_2$ and toluene were obtained from the Aldrich Chemical Company.

Analytical Methods:

Unless otherwise indicated all HPLC analyses were run on an HP-1000 or HP-1050 system with an HP Zorbax SB-$C_{18}$ (5µ) reverse phase column (4.6×150 mm) run at 30° C. with a flow rate of 1.00 mL/min. The mobile phase used solvent A ($H_2O$/0.1% TFA) and solvent B ($CH_3CN$/0.1% TFA) with a 20 min gradient from 10% to 90% $CH_3CN$. The gradient was followed by a 2 min return to 10% $CH_3CN$ and a 3 min flush. The peaks of interest eluted on the LC profiles at the times indicated.

LC-MS Methods:

Method A:
1. Samples were run on an HP-1100 system with an HP Zorbax SB-$C_8$ (5µ) reverse phase column (4.6×50 mm) run at 30° C. with a flow rate of 0.75 mL/min.
2. The mobile phase used solvent A ($H_2O$/0.1% AcOH) and solvent B ($CH_3CN$/0.1% AcOH) with a 10 min gradient from 10% to 90% $CH_3CN$. The gradient was followed by a 1 min return to 10% $CH_3CN$ and a 2 min flush.
3. The peaks of interest eluted on the LC profiles at the times indicated.

Method B:
1. Samples were run on an HP-1100 system with an HP Zorbax SB-$C_8$ (5µ) reverse phase column (4.6×50 mm) run at 30° C. with a flow rate of 1.5 mL/min.
2. The mobile phase used solvent A ($H_2O$/0.1% AcOH) and solvent B ($CH_3CN$/0.1% AcOH) with a 5 min gradient from 10% to 90% $CH_3CN$. The gradient was followed by a 0.5 min return to 10% $CH_3CN$ and a 1.5 min flush.

Preparative HPLC:

Where indicated compounds of interest were purified via preparative HPLC using a Gilson workstation with a 30×100 mm column at 30 mL/min. The mobile phase used solvent A ($H_2O$/0.1% TFA) and solvent B ($CH_3CN$/0.1% TFA) with a 15 min gradient from 5% to 100% $CH_3CN$. The gradient was followed by a 2 min return to 5% $CH_3CN$.

Proton NMR Spectra:

Unless otherwise indicated all $^1$H NMR spectra were run on an Varian series Mercury 300 or 400 MHz instrument.

Preparation I: 4-(3,4-Dinitrophenoxy)-pyridine.

4-Chloropyridine (3.20 g, 28.2 mmol) and 3,4-dinitrophenol (5.96 g, 32.4 mmol) were combined in an open round-bottom flask fitted with running water condenser. The reaction flask was heated to 145° C. After 45 min, 4N HCl/dioxane (2.1 mL) was added. The reaction was heated for an additional 25 min then cooled to RT. The mix was dissolved in EtOAc and 0.5 N HCl/water. The aqueous layer was basified with 6 N NaOH. A beige solid was isolated and identified as title compound.

Preparation II: 4-(3,4-Diamino-phenoxy)-pyridine.

4-(3,4-Dinitro-phenoxy)-pyridine (1.36 g, 5.21 mmol) was dissolved in 20 mL MeOH and 40 mL EtOAc. To the argon-degassed solution was added 10% by weight Pd/C (0.35 g). The reaction was vigorously stirred for 42 h at RT under 1 atm of $H_2$ gas. The reaction was filtered through a Celite® plug. The solvent was removed under reduced pressure to obtain the title compound.

Preparation III: 1-Chloro-4-isothiocyanato-2-trifluoromethyl-benzene.

To a 0° C. solution of 5-amino-2-chlorobenzotrifluoride (0.932 g, 4.76 mmol) in 30 mL $CH_2Cl_2$ was added 1,1'-thiocarbonyldiimidazole (0.976 g, 1.15 mmol). The reaction was warmed to RT and stirred for 45 min. The reaction was stirred for an additional 1 h, during which additional 1,1'-thiocarbonyldiimidazole (0.50 g and 0.20 g) was added at 30 min intervals. The reaction was concentrated down to a small volume and purified by short column silica gel chromatography using EtOAc:hexanes (15:75), to obtain the title compound.

Preparation of Isothiocyanates:

The following isothiocyanates were prepared from corresponding amines similarly to the procedure outlined for 1-chloro-4-isothiocyanate-2-trifluoromethylbenzene.

TABLE 1

| Structure | Mol. Formula | Mol. Weight | MS (MH$^+$) |
|---|---|---|---|
| 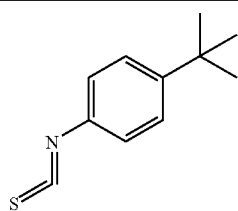<br>1-tert-Butyl-4-isothiocyanoto-benzene | $C_{11}H_{13}NS$ | 191.30 | n/a |

TABLE 1-continued

| Structure | Mol. Formula | Mol. Weight | MS (MH+) |
|---|---|---|---|
| 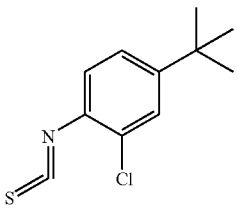<br>4-tert-Butyl-2-chloro-1-iso-thiocyanato-benzene | $C_{11}H_{12}ClNS$ | 225.74 | n/a |
| 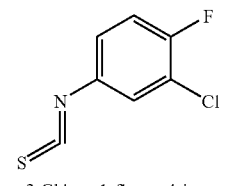<br>2-Chloro-1-fluoro-4-iso-thiocyanato-benzene | $C_7H_3ClFNS$ | 187.62 | n/a |
| 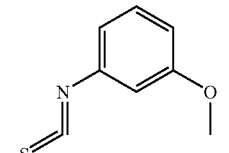<br>1-Isothiocyanato-3-methoxy-benzene | $C_8H_7NOS$ | 165.22 | n/a |
| 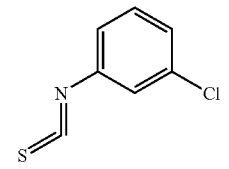<br>1-Chloro-3-isothiocyanato-benzene | $C_7H_4ClNS$ | 169.63 | n/a |
| 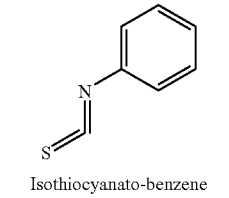<br>Isothiocyanato-benzene | $C_7H_5NS$ | 135.19 | n/a |
| 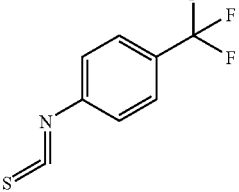<br>1-Isothiocyanato-4-tri-fluoromethyl-benzene | $C_8H_4F_3NS$ | 203.19 | n/a |

TABLE 1-continued

| Structure | Mol. Formula | Mol. Weight | MS (MH+) |
|---|---|---|---|
| [2-(5-Isothiocyanato-2-tri-fluoromethyl-phenoxy)-ethyl]-di-methyl-amine | $C_{12}H_{13}F_3N_2OS$ | 290.31 | n/a |
| 1-(2-Chloro-5-isothiocyanato-ben-zyl)-4-methyl-piperazine | $C_{13}H_{16}ClN_3S$ | 281.81 | 282.5 |
| 2-(5-Isothiocyanato-2-tri-fluoromethyl-phenoxymethyl)-1-meth-yl-pyrrolidine | $C_{14}H_{15}F_3N_2OS$ | 316.35 | 317.1 |
| 1-(2-Chloro-5-isothiocyanato-benzyl)-4-isopropyl-piperazine | $C_{15}H_{20}ClN_3S$ | 309.86 | n/a |
| 4-(2-Chloro-5-isothiocyanato-ben-zyl)-piperazine-1-carboxylic acid tert-butyl ester | $C_{17}H_{22}ClN_3O_2S$ | 367.90 | 368.1 |

TABLE 1-continued

| Structure | Mol. Formula | Mol. Weight | MS (MH+) |
|---|---|---|---|
| 1-(2-Chloro-5-isothiocyanato-benzyl)-4-methanesulfonyl-piperazine | $C_{13}H_{16}ClN_3O_2S_2$ | 345.87 | 346.0 |
| 4-(2-Chloro-5-isothiocyanato-benzyl)-morpholine | $C_{12}H_{13}ClN_2OS$ | 268.77 | 270.0 |
| 1-(2-Chloro-5-isothiocyanato-benzyl)-pyrrolidine | $C_{12}H_{13}ClN_2S$ | 252.77 | n/a |
| 3-Isothiocyanato-isoquinoline | $C_{10}H_6N_2S$ | 186.24 | 187.1 |
| 2-(2-Chloro-5-Isothiocyanato-phenoxymethyl)-1-methyl-pyrrolidine | $C_{13}H_{15}ClN_2OS$ | 282.79 | 283.1 |
| 1-Chloro-4-isothiocyanato-2-(2-methoxyethoxy)benzene | $C_{10}H_{10}ClNO_2S$ | 243.01 | |

TABLE 1-continued

| Structure | Mol. Formula | Mol. Weight | MS (MH+) |
|---|---|---|---|
| 2-(2-Chloro-5-isothiocyanato-phenoxy-methyl)-tetrahydrofuran | $C_{12}H_{12}ClNO_2S$ | 269.75 | |
| 1-[2-(2-Chloro-5-isothiocyanato-phenoxy)ethyl]pyrrolidine | $C_{13}H_{15}ClN_2OS$ | 282.79 | |
| (2S)-2-(2-Chloro-5-isothiocyanato-phenoxy-methyl)-1-isopropyl-pyrrolidine | $C_{15}H_{19}ClN_2OS$ | 310.85 | |
| 1-Chloro-2-(2-Chloro-ethoxy)-4-isothiocyanato-benzene | $C_9H_7Cl_2NOS$ | 248.12 | |

Preparation IV: 1-(2-Chloro-5-nitro-benzyl)-4-methyl-piperazine

To RT solution of 2-chloro-5-nitrobenzaldehyde (3.28 g, 17.7 mmol) and 1-methylpiperazine (1.77 g, 17.7 mmol) in 60 mL $CH_2Cl_2$ was added $NaBH(OAc)_3$ (5.24 g, 24.7 mmol). The reaction was stirred overnight at RT. About 150 mL of 2 N NaOH was added and the reaction was stirred for at least 10 min. The reaction was diluted with $CH_2Cl_2$ and additional 2N NaOH. The layers were separated, and the $CH_2Cl_2$ layer was washed twice with 2 N NaOH. The aqueous layers were back-extracted once with $CH_2Cl_2$. The combined $CH_2Cl_2$ layers were extracted twice with 2 N HCl (total 150 mL), which was then basified to pH>12 by treatment with solid NaOH. This latter aqueous layer was extracted twice with EtOAc. The EtOAc layers were washed once with a mix of brine and 2 N NaOH, combined, dried over $Na_2SO_4$, filtered, and concentrated in vacuo, to yield the title compound as an amber oil. MS(MH+)=NA; Calc'd 269.73 for $C_{12}H_{16}ClN_3O_2$.

The following intermediates were prepared similarly to the procedure outlined above for 1-2-chloro-5-nitrobenzyl-4-methylpiperazine.

TABLE 2

| Structure | Mol. Formula | Mol. Weight |
|---|---|---|
| 1-(2-Chloro-5-nitro-benzyl)-4-isopropyl-piperazine | $C_{14}H_{20}ClN_3O_2$ | 297.79 |
| 4-(2-Chloro-5-nitro-benzyl)-piperazine-1-carboxylic acid tert-butyl ester | $C_{16}H_{22}ClN_3O_4$ | 355.82 |
| 1-(2-Chloro-5-nitro-benzyl)-4-methanesulfonyl-piperazine | $C_{12}H_{16}ClN_3O_4S$ | 333.80 |
| 4-(2-Chloro-5-nitro-benzyl)-morpholine | $C_{11}H_{13}ClN_2O_3$ | 256.69 |
| 1-(2-Chloro-5-nitro-benzyl)-pyrrolidine | $C_{11}H_{13}ClN_2O_2$ | 240.69 |

Preparation V: 1-(2-Chloro-5-amino-benzyl)-4-methyl-piperazine.

To a solution of 1-(2-chloro-5-nitro-benzyl)-4-methyl-piperazine (1.04 g, 3.86 mmol) in 30 mL EtOH was added $SnCl_2$ (2.2 g, 11.6 mmol). The reaction was heated at 70° C. for 4.5 h. An additional amount of $SnCl_2$ (0.7 g, 3.7 mmol) was added, and the reaction was heated at 80° C. for 1 h. The reaction was quenched at RT with 1N aqueous $K_2CO_3$. The white slurry was filtered through a Celite® plug and concentrated to aqueous layer, then diluted with EtOAc and 1N NaOH. The layers were separated, and the organic layer was washed with a brine/1N NaOH mix. The aqueous layers were back-extracted once with EtOAc. The combined organic layers were dried over $Na_2SO_4$, filtered, and concentrated in vacuo, to yield the title compound as a light orange solid. MS (MH$^+$)=240.2; Calc'd 239.75 for $C_{12}H_{12}ClN_3$.

The following intermediates were prepared similarly to the procedure outlined above for 1-(2-chloro-5-aminobenzyl)-4-methylpiperazine.

TABLE 3

| Structure | Mol. Formula | Mol. Weight |
|---|---|---|
| 4-Chloro-3-(4-isopropyl-piperazin-1-ylmethyl)-phenylamine | $C_{14}H_{22}ClN_3$ | 267.80 |
| 4-(5-Amino-2-chloro-benzyl)-piperazine-1-carboxylic acid tert-butyl ester | $C_{16}H_{24}ClN_3O_2$ | 325.84 |
| 4-Chloro-3-(4-methanesulfonyl-piperazin-1-ylmethyl)-phenylamine | $C_{12}H_{18}ClN_3O_2S$ | 303.81 |
| 4-Chloro-3-morpholin-4-ylmethyl-phenylamine | $C_{11}H_{15}ClN_2O$ | 226.71 |
| 4-Chloro-3-pyrrolidin-1-ylmethyl-phenylamine | $C_{11}H_{15}ClN_2$ | 210.71 |

Preparation VI: 1-Boc-4-Methanesulfonyl-piperazine.

To a solution of piperazine-1-carboxylic acid tert-butyl ester (8.39 g, 45.0 mmol) and Et$_3$N (18.8 mL, 135 mmol) in 200 mL CH$_2$Cl$_2$, cooled to 0° C., was added methanesulfonylchloride (3.66 mL, 47.3 mmol). The reaction was warmed to RT and stirred overnight. The reaction was washed once with water, once with 0.2 N HCl, once with 2 N NaOH, and once with brine. The organic layer was dried over Na$_2$SO$_4$, filtered, and concentrated in vacuo to yield the title compound as a white solid. MS (MH$^+$)=NA; Calc'd 264.35 for C$_{10}$H$_{20}$N$_2$O$_4$S.

Preparation VII: 1-Methanesulfonyl-piperazine.

1-Boc-4-Methanesulfonyl-piperazine (10.4 g, 39.5 mmol) was dissolved in 50 mL CH$_2$Cl$_2$ and treated with 15 mL TFA. After stirring at RT for 18 h, the reaction was concentrated in vacuo, dissolved in 1 N HCl and extracted twice with CH$_2$Cl$_2$. The aqueous layer was basified to pH>12 with solid NaOH, then extracted twice with EtOAc. The EtOAc layer was washed with a mix of brine and 1N NaOH, dried over Na$_2$SO$_4$, filtered, and concentrated in vacuo, to yield the title compound as a clear liquid. MS (MH$^+$)=NA; Calc'd 164.23 for C$_5$H$_{12}$N$_2$O$_2$S.

Preparation VIII: 5-Nitro-2-trifluoromethylanisole.

Pyridine (140 mL) was cooled in a large sealable vessel to −40° C. Trifluoromethyl iodide was bubbled in for 20 min from a gas cylinder which had been kept in freezer overnight. 2-Iodo-5-nitroanisole (24.63 g, 88.2 mmol) and copper powder (67.25 g, 1.06 mmol) were added. The vessel was sealed and the reaction was stirred vigorously for 22 h at 140° C. The reaction was cooled to −50° C., and the vessel was carefully opened and poured onto ice and Et$_2$O. After washing with water and Et$_2$O, the reaction was warmed to RT. The layers were separated, the organic layer was washed 3× with 1 N HCl and then brine, dried over Na$_2$SO$_4$, filtered, and concentrated in vacuo. The crude was purified on a short silica gel column (4.5:1 hexanes:CH$_2$Cl$_2$) to provide the title compound.

Preparation IX: 5-Nitro-2-trifluoromethylphenol.

5-Nitro-2-trifluoromethylanisole (10.7 g, 48.5 mmol) and pyridine hydrochloride (44.9 g, 388 mmol) were combined in a round-bottom flask and heated at 210° C. for 2 h. The reaction was cooled to RT and dissolved into 6 N HCl and EtOAc. The layers were separated, and the organic layer was washed 4× with 2 N HCl and once with brine, dried over Na$_2$SO$_4$, filtered, and concentrated in vacuo, to yield the title compound as a dark red solid.

Preparation X: (R)-2-(5-Nitro-2-trifluoromethyl-phenoxymethyl)-1-(tert-butoxycarbonyl)pyrrolidine.

To a solution of 5-nitro-2-trifluoromethylphenol (2.83 g, 13.7 mmol), (R)-(+)-(tert-butoxy-carbonyl)-2-pyrrolidinemethanol (2.75 g, 13.7 mmol), and PPh$_3$ (3.58 g, 13.7 mmol) in 24 mL THF, cooled at −20° C. was added dropwise over 1.5 h a 12 mL THF solution containing DEAD (2.43 g, 13.9 mmol). The mixture turned a deep red. The reaction was warmed gradually to RT and stirred for 18 h. The reaction was concentrated in vacuo and treated with a small mixture of hexanes and Et$_2$O. After sonication, the solids were filtered off, and the filtrate was concentrated in vacuo. The crude was dissolved in a very small amount of EtOAc and Et$_2$O then diluted with hexanes, which were washed once with 0.1N HCl, 3× with 2N NaOH, and once with brine. The organic layer was dried over Na$_2$SO$_4$, filtered, and concentrated in vacuo. The residue was purified by silica gel column chromatography using 5% EtOAc in hexanes to yield the title compound as a clear thick oil.

Preparation XI: (R)-2-(5-Amino-2-trifluoromethyl-phenoxymethyl)-1-(tert-butoxycarbonyl)pyrrolidine.

(R)-2-(5-Nitro-2-trifluoromethyl-phenoxymethyl)-pyrrolidine-1-carboxylic acid tert-butyl ester (2.19 g, 5.60 mmol) was dissolved in 40 mL MeOH and 10 mL dioxane. To the nitrogen-degassed solution was added 10% Pd/C (0.3 g). The reaction was stirred vigorously at RT under 1 atm H$_2$ gas for 42 h. The reaction was filtered through Celite® and concentrated in vacuo to yield the title compound as a white foam. MS (MNa$^+$)=383.3; Calc'd 360.38 for C$_{17}$H$_{23}$F$_3$N$_2$O$_3$.

Preparation XII: (R)-2-(5-Acetylamino-2-trifluoromethyl-phenoxymethyl)-1-(tert-butoxycarbonyl)pyrrolidine.

(R)-2-(5-Amino-2-trifluoromethyl-phenoxymethyl)-)-1-(tert-butoxycarbonyl)pyrrolidine (1.22 g, 3.39 mmol) was dissolved in 6 mL CH$_2$Cl$_2$ at RT. To this solution was added NaHCO$_3$ (0.85 g, 10.2 mmol) then acetyl chloride (0.35 g, 4.44 mmol). The reaction was stirred for 1.5 h. The reaction was diluted with CH$_2$Cl$_2$ and H$_2$O. The layers were separated, and the organic layer was washed with brine. The aqueous layers were back-extracted once with CH$_2$Cl$_2$. The combined organic layers were dried over Na$_2$SO$_4$, filtered, and concentrated in vacuo to yield the title compound as an off-white foam.

Preparation XIII: (R)-N-[3-(Pyrrolidin-2-ylmethoxy)-4-trifluoromethyl-phenyl]-acetamide.

To a solution of (R)-2-(5-acetylamino-2-trifluoromethyl-phenoxymethyl)-1-(tert-butoxycarbonyl)pyrrolidine (1.34 g, 3.33 mol) in 10 mL CH$_2$Cl$_2$ at RT was added 5 mL TFA. The reaction was stirred for 50 min, neutralized with saturated aqueous NaHCO$_3$, and diluted with CH$_2$Cl$_2$ and 2N NaOH. The layers were separated, and the organic layer was brine-washed. The aqueous layers were back-extracted 4 times with CH$_2$Cl$_2$. The combined organic layers were dried over Na$_2$SO$_4$, filtered, and concentrated in vacuo to yield the title compound.

Preparation XIV: (R)-N-[3-(1-Methyl-pyrrolidin-2-ylmethoxy)-4-trifluoromethyl-phenyl]-acetamide.

To a solution of (R)-N-[3-(pyrrolidin-2-ylmethoxy)-4-trifluoromethyl-phenyl]-acetamide (0.85 g, 2.81 mmol) in 25 mL CH$_3$CN was added 1.13 mL formaldehyde (37% in H$_2$O) and NaBH$_3$CN (0.28 g, 4.50 mmol). The reaction was stirred for 1 h, and the pH of the reaction was neutralized every 15 min by introducing several drops of AcOH. The reaction was concentrated in vacuo and dissolved into Et$_2$O and 6 N NaOH. The layers were separated, and the organic layer was washed twice with 6N NaOH and extracted with 6 N HCl twice. The acidic aqueous layer was basified with NaOH pellets and extracted 4 times with CH$_2$Cl$_2$. The CH$_2$Cl$_2$ layers were combined, dried over Na$_2$SO$_4$, filtered, and concentrated in vacuo. The residue was purified by silica gel column chromatography to yield the title compound.

Preparation XV: (R)-3-(1-Methyl-pyrrolidin-2-ylmethoxy)-4-trifluoromethyl-phenylamine A solution of (R)-N-[3-(1-methyl-pyrrolidin-2-ylmethoxy)-4-trifluoromethyl-phenyl]-acetamide (0.49 g, 1.56 mmol) in 18 mL EtOH was added 11 mL concentrated HCl. The reaction was heated, in a sealed tube, at 70° C. for 6 h, then at 100° C. for 2 h. The reaction was cooled, concentrated to aqueous, basified with 6 N NaOH, and extracted 4 times with CH$_2$Cl$_2$. The combined organic layers were dried over Na$_2$SO$_4$, filtered, and concentrated in vacuo to yield the title compound as a tan solid.

Preparation XVI: 1-nitro-3-(2-Dimethylamino-ethoxy)-4-trifluoromethylbenzene.

5-Nitro-2-trifluoromethylphenol (3.48 g, 16.8 mmol) was heated in a sealed tube at 105° C. along with 2-(dimethylamino)ethylchloride hydrochloride (5.32 g, 37.0 mmol), K$_2$CO$_3$ (9.76 g, 70.7 mmol), 114 mL acetone, 33 mL H$_2$O, and Bu$_4$N$^+$I$^-$ (0.5 g, 1.34 mmol) for 24 h, then at 120° C. for 24 h. The reaction was cooled to RT and concentrated to aqueous layer, which was diluted with brine and 6 N NaOH and extracted with EtOAc. The organic layer was dried over Na$_2$SO$_4$, filtered, and concentrated in vacuo. Purification by silica gel column chromatography yielded the title compound as a light brown oil.

Preparation XVII: 3-(2-Dimethylamino-ethoxy)-4-trifluoromethylaniline.

The title compound was prepared similarly to the procedure outlined above for (R)-2-(5-amino-2-trifluoromethyl-phenoxymethyl)-1-(Boc)pyrrolidine. MS (MH$^+$)=249.1; Calc'd 248.25 for C$_{11}$H$_{15}$F$_3$N$_2$O.

Preparation XVIII: 2-Chloro-5-nitrophenol

2-Chloro-5-nitroanisole (9.7 g, 49.1 mmol) in HOAc (78 mL) and 48% HBr (97 mL) was heated for 18 h at 140° C. The reaction was cooled to RT, diluted with ice water, and extracted with EtOAc once the ice had melted. The organic layer was brine-washed 4×, dried over Na$_2$SO$_4$, filtered, concentrated, and dried under vacuum to yield the title compound as yellow-light brown solid.

Preparation XIX: (S)-2-(2-Chloro-5-nitro-phenoxymethyl)-pyrrolidine-1-carboxylic acid tert-butyl ester To a solution of 2-chloro-5-nitrophenol (5.06 g, 29.17 mmol), (S)-(−)-1-(tert-butoxycarbonyl)-2-pyrrolidinemethanol (5.87 g, 29.17 mmol), and Ph$_3$P (7.65 g, 29.17 mmol) in 50 mL THF, cooled to −15° C., was added dropwise, over 75 min, a solution of DIAD (6.02 g, 29.75 mmol). The reaction was warmed to RT and stirred for 18 h. The reaction was concentrated to dryness. The crude residue was treated with a small mix of $Et_2O$ and hexanes and sonicated so as to triturate out bulk of impurities, which were filtered off. The filtrate was concentrated to dryness. The resulting residue was purified by silica gel column chromatography using 7% EtOAc in hexanes to elute the title compound as a thick yellow oil.

Preparation XX: (S)-2-(2-Chloro-5-nitro-phenoxymethyl)-pyrrolidine (S)-2-(2-Chloro-5-nitro-phenoxymethyl)-pyrrolidine-1-carboxylic acid tert-butyl ester (6.94 g, 19.45 mmol) was stirred in 30 mL $CH_2Cl_2$ and 20 ml TFA for 3 h. The reaction was concentrated and dissolved in 0.1 N HCl (aq), which was basified to pH>12 with solid NaOH and extracted 3× with EtOAc. The organic layers were washed once with 1 N NaOH then once with a mixture of brine and 1 N NaOH. The organic layers were combined, dried over $Na_2SO_4$, filtered, and concentrated to dryness, to yield the title compound as a yellow solid.

Preparation XXI: (S)-2-(2-Chloro-5-nitro-phenoxymethyl)-1-methylpyrrolidine

To (S)-2-(2-chloro-5-nitro-phenoxymethyl)-pyrrolidine (4.82 g, 18.77 mmol) in 167 mL $CH_3CN$ at RT was added 37% aqueous formaldehyde (7.58 mL) then $NaCNBH_3$ (1.887 g, 30.03 mmol). The reaction was stirred for 1 h, as the reaction pH was adjusted every 10 min to about 7 by adding small amounts of HOAc. The reaction was concentrated to small aqueous volume and dissolved into 2 N NaOH (aq) and $Et_2O$. The layers were separated, and the organic layer was washed twice with 2 N NaOH then extracted twice with 1 N HCl (aq). The combined acidic aqueous layers were basified to pH>12 with solid NaOH and extracted 3× with EtOAc. The EtOAc layers were washed once with 2 N NaOH then once with a mixture of brine and 2 N NaOH, combined, dried over $Na_2SO_4$, filtered, and concentrated down to dryness, to yield the title compound.

Preparation XXII: (S)-β-Chloro-3-(1-methyl-pyrrolidin-2-ylmethoxy)-phenylamine (S)-2-(2-Chloro-5-nitro-phenoxymethyl)-pyrrolidine (3.42 g, 12.63 mmol) and $SnCl_2$ (7.19 g, 37.9 mmol) in 45 mL EtOH were heated at 75° C. for 11 h. The reaction was treated with about 15 mL 1 N $K_2CO_3$ (aq) and stirred for 40 min. The suspension was filtered through Celite® and concentrated to aqueous, which was then diluted with EtOAc and 1 N NaOH (aq). The layers were separated, and the organic layer was washed twice with 1 N NaOH and once with a mixture of brine and 1 N NaOH. The aqueous layers were extracted twice with fresh EtOAc. The combined organic layers were dried over $Na_2SO_4$, filtered, and concentrated to dryness to yield the title compound as a brown solid.

Preparation XXIII: (S)-2-(2-Chloro-5-nitro-phenoxymethyl)-1-methylpyrrolidine

To (S)-2-(2-chloro-5-nitro-phenoxymethyl)-pyrrolidine (4.82 g, 18.77 mmol) in 167 mL $CH_3CN$ at RT was added 37% aqueous formaldehyde (7.58 mL) then $NaCNBH_3$ (1.887 g, 30.03 mmol). The reaction was stirred for 1 h, as the reaction pH was adjusted every 10 min to about 7 by adding small amounts of HOAc. The reaction was concentrated to small aqueous volume and dissolved in 2 N NaOH (aq) and $Et_2O$. The layers were separated, and the organic layer was washed twice with 2 N NaOH then extracted twice with 1 N HCl (aq). The combined acidic aqueous layers were basified to pH>12 with solid NaOH and extracted 3 times with EtOAc. The EtOAc layers were washed once with 2 N NaOH and then once with mix of brine and 2 N NaOH, combined, dried over $Na_2SO_4$, filtered, and concentrated to dryness, to yield the title compound.

Preparation XXIV: (S)-4-Chloro-3-(1-methyl-pyrrolidin-2-ylmethoxy)-phenylamine (S)-2-(2-Chloro-5-nitro-phenoxymethyl)-pyrrolidine (3.42 g, 12.63 mmol) and $SnCl_2$ (7.19 g, 37.9 mmol) in 45 mL EtOH were heated at 75° C. for 11 h. The reaction was treated with about 15 mL 1 N $K_2CO_3$ (aq) and stirred 40 min. The suspension was filtered through Celite and concentrated down to aqueous, which was then diluted with EtOAc and 1 N NaOH (aq). The layers were separated, and the organic layer was washed twice with 1 N NaOH and once with mix of brine and 1 N NaOH. The aqueous layers were extracted twice with fresh EtOAc. The combined organic layers were dried over sodium sulfate, filtered, and concentrated down to dryness to yield the title compound as a brown solid.

Preparation XXV: 3-nitro-5-trifluoromethyl-phenol

1-Methoxy-3-nitro-5-trifluoromethyl-benzene (10 g, Aldrich) and pyridine-HCl (41.8 g, Aldrich) were mixed and heated neat at 210° C. in an open flask. After 2.5 h the mixture was cooled to RT and partitioned between 1 N HCl and EtOAc. The EtOAc fraction was washed with 1N HCl (4×), brine (1×), dried with $Na_2SO_4$, filtered and concentrated in vacuo to form 3-nitro-5-trifluoromethyl-phenol as an off-white solid.

Preparation XXVI: (R)-2-(3-nitro-5-trifluoromethyl-phenoxymethyl)-pyrrolidine-1-carboxylic acid tert-butyl ester The title compound was prepared similarly to the procedure outlined in the Preparation X starting from 3-nitro-5-trifluoromethyl-phenol.

Preparation XXVII: (R)-2-(3-nitro-5-trifluoromethyl-phenoxymethyl)-pyrrolidine:

1-Boc-2-(3-nitro-5-trifluoromethyl-phenoxymethyl)-pyrrolidine (2.35 g) was dissolved in $CH_2Cl_2$ (60 mL) and TFA (20 mL) was added. After stirring for 1 h at RT, the mixture was concentrated in vacuo to yield 2-(3-nitro-5-trifluoromethyl-phenoxymethyl)-pyrrolidine as an oil that solidified upon standing. The material was used as is without further purification.

Preparation XXVIII: (R)-1-methyl-2-(3-nitro-5-trifluoromethyl-phenoxymethyl)-pyrrolidine:

2-(3-Nitro-5-trifluoromethyl-phenoxymethyl)-pyrrolidine (6 mmol) was dissolved in $CH_3CN$ (20 mL) and formaldehyde (2.4 mL, 37% aqueous) was added. $NaBH_3CN$ (607 mg) was added, an exotherm was observed. The pH was monitored every 15 min and adjusted to ~7 with AcOH. After 45 min, the mixture was concentrated in vacuo and the residue was dissolved in EtOAc, washed with 6 N NaOH, 1 N NaOH, and 2 N HCl (3×). The acid washings were combined, adjusted to ~pH 10 with solid $Na_2CO_3$ and extracted with EtOAc (2×). The EtOAc fractions were combined, dried with $Na_2SO_4$, and purified with flash chromatography ($SiO_2$, 95:5: 0.5 $CH_2Cl_2$:MeOH:$NH_4OH$) to afford the title compound.

Preparation XXIX: (R)-3-(1-methyl-pyrrolidin-2-ylmethoxy)-5-trifluoromethyl-phenylamine 1-Methyl-2-(3-nitro-5-trifluoromethyl-phenoxymethyl)-pyrrolidine (2.5 g, 8.2 mmol) was dissolved in MeOH (80 ml) and HOAc (glacial, 10 mL) and placed under $N_2$. Pd/C was added and after blanketing with $H_2$, the mixture was shaken under $H_2$ for 18 h at 60 psi. The catalyst was removed by filtration through Celite® and the MeOH solution was concentrated in vacuo. The residue was purified with flash chromatography ($SiO_2$, 90:10:1 $CH_2Cl_2$:MeOH:$NH_4OH$) to afford the title compound as a yellow liquid.

Preparation XXX: (R)-2-(3-isothiocyanato-5-trifluoromethyl-phenoxymethyl)-1-methyl-pyrrolidine The title compound was prepared similarly to the procedure outlined for Preparation III. MS (MH$^+$)=NA; Calc'd 316.46 for $C_{14}H_{15}F_3N_2OS$.

Preparation XXXI: 4-(2-chloro-5-nitro-phenoxymethyl)-piperidine-1-carboxylic acid tert-butyl ester To a solution of 2-chloro-5-nitro phenol (10 g, 63.497 mmol), N-boc-4-piperidine methanol (13.67 g, 63.49 mmol), and PPh$_3$ (16.63 g, 63.49 mmol) in 130 mL THF, cooled at −20° C. was added dropwise over 1.5 h a 50 mL THF solution containing DIAD (12.75 ml, 64.76 mmol). The mixture turned a deep red. The reaction was warmed gradually to RT and stirred for 18 h. The mixture was concentrated in vacuo, dissolved in Et$_2$O, washed once with water, then NaHCO$_3$ (sat). The organic layer was dried over Na$_2$SO$_4$, filtered, and concentrated in vacuo. The residue was treated with a mixture of hexanes and EtOAc (1:1) and the solid was filtered. The filtrate was evaporated and the residue was purified by silica gel column chromatography to yield the title compound as a yellow solid. MS (MH$^+$)=NA; Calc'd 370.13 for $C_{17}H_{23}ClN_2O_5$.

Preparation XXXII: 4-(2-chloro-5-nitro-phenoxymethyl)-piperidine 4-(2-Chloro-5-nitro-phenoxymethyl)-piperidine-1-carboxylic acid tert-butyl ester (14.58 g, 39.3 mmol) was dissolved in TFA (100 mL). After stirring for 2 h at RT, the mixture was concentrated in vacuo and taken up into EtOAc and washed with NaOH, then NaHCO$_3$ (sat). The organic layer was dried with Na$_2$SO$_4$, filtered and evaporated to yield the title compound as a yellow solid. MS(MH$^+$)=NA; Calc'd 269.07 for $C_{12}H_{15}ClN_2O_3$.

Preparation XXXIII: 4-(2-chloro-5-nitro-phenoxymethyl)-1-methyl-piperidine 4-(2-Chloro-5-nitro-phenoxymethyl)-piperidine (4 g, 14.8 mmol) was dissolved in CH$_3$CN (20 ml), and formaldehyde (5.9 ml, 37% aqueous) and NaBH$_3$CN (1.49 g, 23.68 mmol) were added. After 4 h, the mixture was concentrated in vacuo and the residue was dissolved in EtOAc, washed with brine. The EtOAc portion was dried with Na$_2$SO$_4$, and evaporated. The title compound was purified by column chromatography using 0-75% of a 90:10:1 (CH$_2$Cl$_2$:MeOH: NH$_4$OH) solution as the eluent to yield a yellow solid. MS(MH$^+$)=NA; Calc'd 284.09 for $C_{13}H_{17}ClN_2O_3$.

Preparation XXXIV: 4-chloro-3-(1-methyl-piperidin-4-ylmethoxy)-phenylamine

The title compound was prepared from 4-(2-chloro-5-nitro-phenoxymethyl)-1-methyl-piperidine using the procedure outlined in the preparation of Example 377, Step D. MS(MH$^+$)=NA; Calc'd 254.12 for $C_{13}H_{19}ClN_2O$.

Preparation XXXV: 4-(2-Chloro-5-isothiocyanato-phenoxymethyl)-1-methyl-piperidine The title compound was prepared similarly as Preparation III using the corresponding aniline. MS(MH$^+$)=NA; Calc'd 296.08 for $C_{14}H_{17}ClN_2OS$.

Preparation XXXVI: 4-(2-Chloro-5-nitro-phenoxymethyl)-1-isopropyl-piperidine 4-(2-Chloro-5-nitro-phenoxymethyl)-piperidine (7 g, 25.9 mmol) was dissolved in CH$_3$CN (50 mL) and acetone (9.48 ml, 129 mmol) was added. NaBH$_3$CN (2.6 g, 41.4 mmol) was added. After 14 h, the mixture was concentrated in vacuo and the residue was dissolved in EtOAc, washed with brine. The EtOAc portion was dried with Na$_2$SO$_4$, and evaporated. The title compound was purified by column chromatography using 0-75% of a 90:10:1 (CH$_2$Cl$_2$:MeOH: NH$_4$OH) solution as the eluent to yield a yellow solid. MS(MH$^+$)=NA; Calc'd 312.12 for $C_{15}H_{21}ClN_2O_3$.

Preparation XXXVII: 4-Chloro-3-(1-isopropyl-piperidin-4-ylmethoxy)-phenylamine

The title compound was prepared from 4-(2-chloro-5-nitro-phenoxymethyl)-1-isopropyl-piperidine using the procedure outlined in the preparation of Example 377, Step D. MS(MH$^+$)=NA; Calc'd 282.15 for $C_{15}H_{23}ClN_2O$.

Preparation XXXVIII: 4-(2-Chloro-5-isothiocyanato-phenoxymethyl)-1-isopropyl-piperidine The title compound was prepared similarly to the procedure outlined for Preparation III. MS(MH$^+$)=NA; Calc'd 324.11 for $C_{16}H_{21}ClN_2OS$.

Preparation XLIX: 2-(2-Chloro-5-nitro-phenoxymethyl)-tetrahydrofuran

To a solution of 2-chloro-5-nitrophenol (3.39 g, 19.52 mmol), tetrahydrofurfuryl alcohol (1.99 g, 19.52 mmol), and Ph$_3$P (5.12 g, 19.52 mmol) in 34 ml THF, cooled to −15° C., was added dropwise, over 90 min, a solution of DIAD (4.15 g, 20.5 mmol). The reaction was warmed to RT and stirred for 18 h. The reaction was concentrated to dryness. The crude residue was treated with a small mix of Et$_2$O and hexanes and sonicated so as to triturate out bulk of impurities, which were filtered off. The filtrate was concentrated to dryness. The resulting residue was purified by silica gel column chromatography using EtOAc in hexanes to elute the title compound.

Preparation XL: 4-Chloro-3-(tetrahydrofuran-2-ylmethoxy)-phenylamine

A solution of 2-(2-chloro-5-nitro-phenoxymethyl)-tetrahydrofuran (0.45 g, 1.75 mmol) in EtOAc (10 mL) was degassed with argon then charged with 10% by weight Pd/C (0.4 g). The mixture was stirred for 7 h under an H$_2$ atmosphere, filtered through Celite® and concentrated in vacuo. A mixture contained the title compound along with starting material in a 7:3 ratio. MS: (MH+)=227.1; Calc'd 227.69 for $C_{11}H_{15}ClNO_2$.

Preparation XLI: 5-Amino-2-chlorophenol

2-Chloro-5-nitrophenol (3.06 g, 17.6 mmol) and SnCl$_2$ (10.0 g, 52.8 mmol) in EtOH (120 mL) were heated for 10 h at 80° C. The reaction was treated with 1N K$_2$CO$_3$ (aq) and filtered through Celite. Most of the solvent was removed under vacuum. The crude was treated with saturated NaHCO$_3$ and extracted with EtOAc twice. The organic layers were washed with water then brine, dried over Na$_2$SO$_4$, filtered, and concentrated in vacuo to yield the title compound as a brown-green solid.

Preparation XLII: 4-Chloro-3-(2-pyrrolidin-1-yl-ethoxy)-phenylamine

To a stirring RT slurry of NaH (0.10 g of a 60% by weight oil dispersion, 2.5 mmol) in DMF (2 mL) was added 5-amino-2-chlorophenol (0.20 g, 1.4 mmol). The mixture was stirred for 10 min before adding 1-(2-chloroethyl-pyrrolidine hydrochloride (0.17 g, 1.0 mmol). The reaction was heated at 80° C. for 15 h. The reaction was quenched with water, treated with 1N NaOH, and extracted twice with EtOAc. The combined organic layers were washed with brine, dried over Na$_2$SO$_4$, filtered, and concentrated in vacuo. The crude residue was purified by silica gel chromatography to yield title compound. MS: (MH$^+$)=241.2; Calc'd 240.74 for $C_{12}H_{17}ClN_2O$.

Preparation XLIII: 1-Chloro-2-(2-chloro-ethoxy)-4-nitrobenzene

A mixture of 2-chloro-5-nitrophenol (4 g, 23 mmol), 1-bromo-2-chloroethane (9 mL, 115 mmol), and K$_2$CO$_3$ (8 g, 58 mmol) in DMF (50 mL) was heated at 80° C. for 18 h. The mixture was diluted with water and extracted several times with EtOAc. The combined organic layers were washed with 1N NaOH (aq) and concentrated in vacuo to yield the title compound and a bromo adduct contaminant.

Preparation XLIV: 4-Chloro-3-(2-chloro-ethoxy)-phenylamine

To an argon-degassed solution of 1-chloro-2-(2-chloroethoxy)-4-nitro-benzene (2.9 g, <12.5 mmol due to contamination) in EtOAc (50 mL) was added 10% by weight Pd/C (1 g). The reaction was stirred under $H_2$ for 18 h then filtered through Celite® and concentrated in vacuo to yield the title compound contaminated by the bromo adduct. MS (MH$^+$) =206.1; Calc'd 206.07 for $C_8H_9Cl_2NO$.

EXAMPLE 1

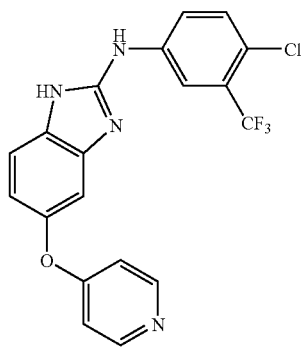

(4-Chloro-3-trifluoromethyl-phenyl)-[5-(pyridin-4-yloxy)-1H-benzimidazol-2-yl]-amine To a solution of 4-(pyridin-4-yloxy)-benzene-1,2-diamine (0.273 g, 1.36 mmol) in 20 mL $CH_3CN$ was added 1-chloro-4-isothiocyanato-2-trifluoromethyl-benzene (prepared similarly to the procedure described in Preparation III, 0.322 g, 1.36 mmol). The reaction was stirred 18 h at RT. The reaction was diluted with 25 mL $CH_3CN$, and then EDC (0.39 g, 2.03 mmol) was added. The reaction was heated at 80° C. for 2.5 h. The reaction was cooled to RT and concentrated in vacuo. The crude mix was dissolved into EtOAc and water. The layers were separated, and the organic layer was washed with brine, dried over $Na_2SO_4$, filtered, and concentrated in vacuo. The residue was purified by silica gel column chromatography using a hexane-EtOAc gradient. The partially pure compound was triturated with $CH_2Cl_2$ to yield the title compound. MS (MH$^+$)=405.1; Calc'd 404.78 for $C_{19}H_{12}ClF_3N_4O$.

EXAMPLE 1a TO 1k

The following compounds were prepared similarly to the procedure outlined above in Example 1.

| Ex. | Structure | Mol Formula | Mol Weight | MS (MH+) |
|---|---|---|---|---|
| 1a | N-(4-(1,1-Dimethylethyl)-phenyl)-5-(4-pyridinyloxy)-1H-benzimidazol-2-amine | $C_{22}H_{22}N_4O$ | 358.18 | 359.2 |
| 1b | N-(2-Chloro-4-(1,1-dimethylethyl)phenyl)-5-(4-pyridinyloxy)-1H-benzimidazol-2-amine | $C_{22}H_{21}ClN_4O$ | 392.14 | 393.0 |

-continued

| Ex. | Structure | Mol Formula | Mol Weight | MS (MH+) |
|---|---|---|---|---|
| 1c | 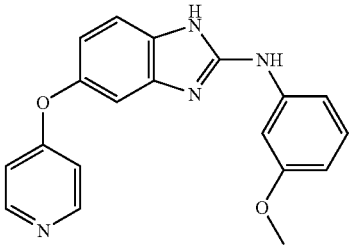<br>N-(3-(Methoxy)phenyl)-5-(4-pyridinyl-oxy)-1H-benzimidazol-2-amine | $C_{19}H_{16}N_4O_2$ | 332.13 | 333.0 |
| 1d | 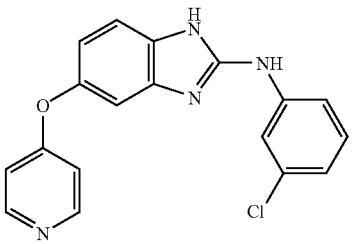<br>N-(3-Chlorophenyl)-5-(4-pyridinyloxy)-1H-benzi-midazol-2-amine | $C_{18}H_{13}ClN_4O$ | 336.08 | 337.0 |
| 1e | 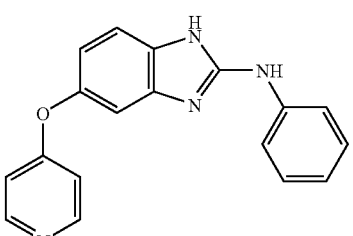<br>N-Phenyl-5-(4-pyridinyloxy)-1H-benzimi-dazol-2-amine | $C_{18}H_{14}FN_4O$ | 302.12 | 303.0 |
| 1f | 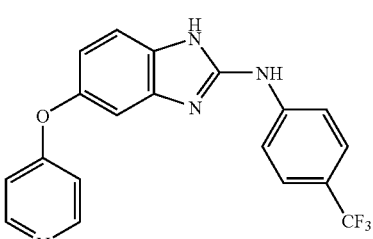<br>5-(4-Pyridinyloxy)-N-(3-(trifluorometh-yl)phenyl)-1H-benzimidazol-2-amine | $C_{19}H_{13}F_3N_4O$ | 370.11 | 371.0 |
| 1g | 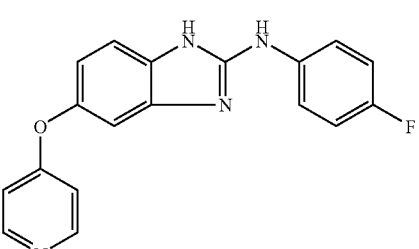<br>(4-Fluoro-phenyl)-[5-(pyridin-4-yloxy)-1H-benzi-midazol-2-yl]-amine | $C_{18}H_{13}FN_4O$ | 320.11 | 320.8 |

-continued

| Ex. | Structure | Mol Formula | Mol Weight | MS (MH+) |
|---|---|---|---|---|
| 1h | (3-Fluoro-phenyl)-[5-(pyridin-4-yloxy)-1H-benzimidazol-2-yl]-amine | C$_{18}$H$_{13}$FN$_4$O | 320.11 | 320.9 |
| 1i | (3,4-Difluoro-phenyl)-[5-(pyridin-4-yloxy)-1H-benzimidazol-2-yl]-amine | C$_{18}$H$_{12}$F$_2$N$_4$O | 338.10 | 339.2 |
| 1j | (3-Trifluoromethyl-phenyl)-[5-(pyridin-4-yloxy)-1H-benzimidazol-2-yl]-amine | C$_{19}$H$_{13}$F$_3$N$_4$O | 370.10 | 370.9 |
| 1k | N-(3-chloro-4-fluorophenyl)-5-(4-pyridinyloxy)-1H-benzimidazol-2-amine | C$_{18}$H$_{12}$ClFN$_4$O | 354.07 | 355.0 |

EXAMPLE 2

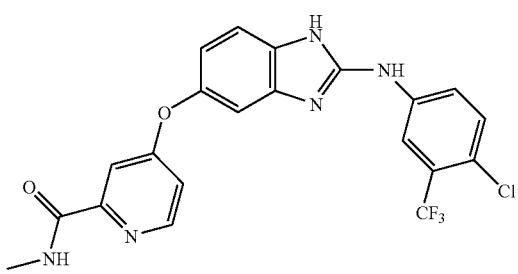

4-[2-(4-Chloro-3-trifluoromethylphenylamino)-1H-benzimidazol-5-yloxy]-pyridine-2-carboxylic acid methylamide Step A: 4-(3,4-Dinitrophenoxy)pyridine-2-carboxylic acid methylamide.

3,4-Dinitrophenol (12.3 g, 66.8 mmol) and 4-chloro-pyridine-2-carboxylic acid methylamide prepared similarly as described in patent WO 00/42012 (less than 7.79 g, 45.7 mmol, due to contaminant) in an open 50 mL round-bottom flask provided with stir bar and fitted with running water condenser. The reaction was heated at 150° C. for 1 h and at 170° C. for 16 h. The reaction was cooled to RT and dissolved in CH$_2$Cl$_2$ and 2N NaOH (aq). The layers were separated, and the organic layer was washed with a mix of brine and 2 N NaOH. The aqueous layers were back-extracted with CH$_2$Cl$_2$. The combined organic layers were dried over Na$_2$SO$_4$, filtered, and concentrated in vacuo. The crude residue was purified by silica gel column chromatography using a hexanes-to-hexanes/EtOAc gradient, to yield the title compound.

Step B: 4-(3,4-Diamino-phenoxy)-pyridine-2-carboxylic acid methylamide.

4-(3,4-Dinitro-phenoxy)-pyridine-2-carboxylic acid methylamide (Step A) (0.71 g, 2.23 mmol) was dissolved in 40 mL MeOH and 80 mL EtOAc. To the argon-degassed solution was added 10% Pd/C (0.20 g). The reaction was vigorously stirred for 42 h at RT under 1 atm of H$_2$ gas. The reaction was filtered through a Celite® plug. The solvent was removed under reduced pressure to obtain the title compound.

Step C: 4-[2-(4-Chloro-3-trifluoromethyl-phenylamino)-1H-benzimidazol-5-yloxy]-pyridine-2-carboxylic acid methylamide.

To a solution of 4-(3,4-diamino-phenoxy)-pyridine-2-carboxylic acid methylamide (Step B) (0.07 g, 0.27 mmol) in 20 mL CH$_3$CN was added dropwise, over 5 min, a solution 1-chloro-4-isothiocyanato-2-trifluoromethyl-benzene (0.055 g, 0.27 mmol) in 10 mL CH$_3$CN. The reaction was stirred 18 h at RT. The reaction was diluted with 10 mL CH$_3$CN, then EDC (0.078 g, 0.41 mmol) was added. The reaction was heated at 80° C. for 3 h. The reaction was cooled to RT and concentrated in vacuo. The crude mix was dissolved in EtOAc and water. The layers were separated, and the organic layer was washed with brine, dried over Na$_2$SO$_4$, filtered, and concentrated in vacuo. The residue was purified by silica gel column chromatography using a hexane-EtOAc gradient to yield the title compound. MS (MH$^+$)=461.9; MW Calc'd 461.09 for C$_{21}$H$_{15}$ClF$_3$N$_5$O$_2$.

EXAMPLE 3 chloride (9.71 g, 57.1 mmol), K$_2$CO$_3$ (7.9 g, 57.1 mmol), and acetone (20 mL). The reaction was heated at 70° C. for 3 days. The acetone evaporated from the reaction. No reaction was observed, so the organic material was recovered by extraction of water with EtOAc. The organic layer was dried with MgSO$_4$, filtered and concentrated in vacuo. This crude mixture was dissolved in DMF (20 mL), combined with K$_2$CO$_3$ (5.9 g, 42.1 mmol) and heated to 70° C. for 24 h. The reaction mixture was cooled to RT, taken up in EtOAc and washed with 2 N NaOH, and brine. The organic layer was dried with MgSO$_4$, filtered and concentrated in vacuo. The aqueous layer was acidified, extracted with EtOAc and dried with MgSO$_4$, filtered, concentrated in vacuo and combined with the other portion. The title compound was purified by column chromatography using 0-10% MeOH in CH$_2$Cl$_2$.

Step B: 4-Pentafluoroethyl-3-(2-pyrrolidin-1-yl-ethoxy)-phenylamine.

A flask was charged with 1-[-(5-nitro-2-pentafluoroethyl-phenoxy)-ethyl]-pyrrolidine (Step A) (1.8 g) and MeOH (25 mL) and placed under argon. Pd/C was added carefully and the atmosphere was replaced with H$_2$. The reaction was stirred for 2.5 days at RT. The reaction mixture was blanketed with N$_2$, filtered through a pad of Celite® and evaporated. The reaction mixture was taken up in a small amount of acetone, and filtered through a plug of silica gel using 90:10:1 (CH$_2$Cl$_2$:MeOH:NH$_4$OH) as the eluant. The title compound was isolated as a yellow solid.

Step C: 4-{2-[4-Pentafluoroethyl-3-(2-pyrrolidin-1-yl-ethoxy)-phenylamino]-1H-benzimidazol-5-oloxy}-pyridine-2-carboxylic acid methylamide.

The title compound was prepared similarly to the procedures described in Preparation III and Example 1, and purified by preparatory HPLC to yield an off-white solid. M+H 591.2, Calc'd for C$_{28}$H$_{27}$F$_5$N$_6$O$_3$— 590.21.

EXAMPLE 4

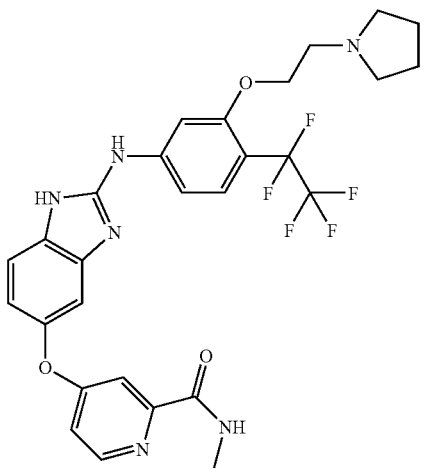

4-{2-[4-Pentafluoroethyl-3-(2-pyrrolidin-1-yl-ethoxy)-phenylamino]-1H-benzimidazol-5-yloxy}-pyridine-2-carboxylic acid methylamide Step A: 1-[2-(5-Nitro-2-pentafluoroethylphenoxy)-ethyl]-pyrrolidine.

A flask was charged with 5-nitro-2-pentafluoroethyl-phenol (3.67 g, 14.2 mmol), 1-(2-chloroethyl)pyrrolidine hydro-

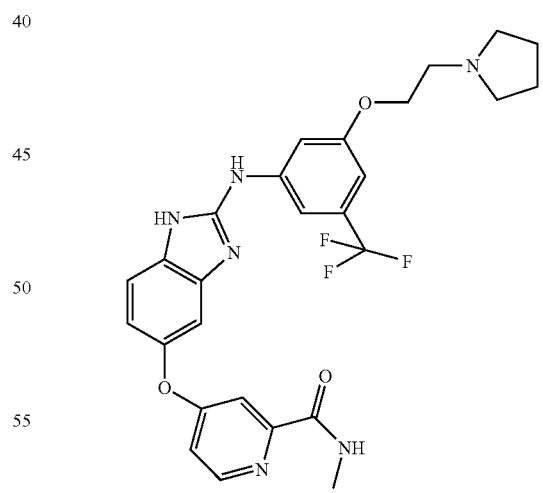

4-{2-[3-(2-Pyrrolidin-1-yl-ethoxy)-5-trifluoromethyl-phenylamino]-1H-benzimidazol-5-yloxy}-pyridine-2-carboxylic acid methylamide Step A: 3-Nitro-5-trifluoromethyl-phenol.
1-Methoxy-3-nitro-5-trifluoromethyl-benzene (10 g, Aldrich) and pyridine-HCl (41.8 g, Aldrich) were mixed together and heated neat at 210° C. in an open flask. After 2.5 h, the mixture was cooled to RT and partitioned between 1N HCl and EtOAc. The EtOAc fraction was washed with 1 N HCl (4×), brine (1×), dried with $Na_2SO_4$, filtered and concentrated in vacuo to form 3-nitro-5-trifluoromethyl-phenol as an off-white solid.

Step B: 1-[2-(3-Nitro-5-trifluoromethyl-phenoxy)ethyl]-pyrrolidine.

The title compound was prepared similarly to the compound in Example 3, Step A.

Step C: 3-(2-Pyrrolin-1-yl-ethoxy)-5-trifluoromethyl-phenylamine.

The title compound was prepared similarly to the compound in Example 3, Step B.

Step D: 1-[2-(3-Thioisocyanato-5-trifluoromethyl-phenoxy)-ethyl]-pyrrolidine.

A flask was charged with 3-(2-pyrrolin-1-yl-ethoxy)-5-trifluoromethyl-phenylamine (Step C), (560.0 mg, 2 mmol) and $CH_2Cl_2$ (10 mL) and placed in an ice bath. To this solution, 1,1-thiocarbonyldiimidazole (463 mg, 2.6 mmol) was added and the reaction was warmed to RT. After 4 h, the solvent was concentrated in vacuo and the residual yellow solid was titrated with acetone to yield the title compound as a 1/1 mixture with imidazole. This mixture was used directly in the next step.

Step E: 4-{2-[3-(2-Pyrrolidin-1-yl-ethoxy)-5-trifluoromethyl-phenylamino]-1H-benzimidazol-5-yloxy}-pyridine-2-carboxylic acid methylamide.

The title compound was prepared similarly to the procedure described for Example 2, Step C, and purified by preparatory HPLC to yield an off-white solid. M+H 541.3, Calc'd for $C_{27}H_{27}F_3N_6O_3$— 540.21.

EXAMPLE 5

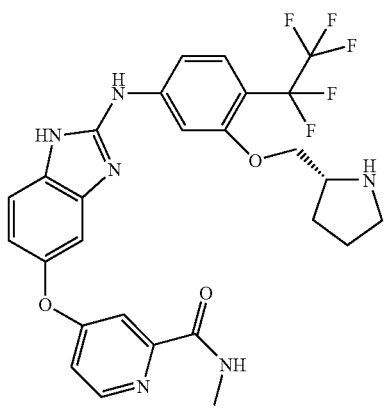

4-(2-R-[4-Pentafluoro-3-(pyrrolidin-2-ylmethoxy)-phenylamino]-1H-benzimidazol-5-yloxy)-pyridine-2-carboxylic acid methylamide.

Step A: 2-Methoxy-4-nitro-1-pentafluoroethylbenzene

3-Methoxy-1-nitro-4-(perfluoroethyl)benzene can be synthesized by the method similar to that described in J. Freskos, Synthetic Communications, 18(9):965-972 (1988)]. Alternatively, 3-methoxy-1-nitro-4-(perfluoroalkyl)benzene can be synthesized from a p-iodonitrobenzene compound by the method described by W. Gregory, et al., J. Med. Chem., 33:2569-2578 (1990).

Step B: 5-Nitro-2-pentafluoroethylphenol

2-Methoxy-4-nitro-1-pentafluoroethylbenzene (9.35 g) and pyridine hydrochloride were combined in a round bottom flask and heated at 210° C. for 1 h, then cooled to RT. The mixture was diluted with EtOAc and 2 N HCl (>500 mL) until all residues dissolved. The organic layer was removed, washed with 2 N HCl (2×) and concentrated in vacuo. The residue was dissolved in hexanes and $Et_2O$, washed with 2 N HCl, then brine. The organic layer was dried over $Na_2SO_4$, filtered, concentrated in vacuo and dried under high vacuum to provide 5-nitro-2-pentafluoromethylphenol.

Step C: R-2-(5-Nitro-2-pentafluoroethyl-phenoxymethyl)-1-(tert-butoxycarbonyl)pyrrolidine.

A flask was charged with 5-nitro-2-pentafluoroethyl-phenol (945.0 mg, 3.7 mmol Step A), $PPh_3$ (965.0 mg, 3.7 mmol), R-(+)-(1-tert-butoxycarbonyl)-2-pyrrolidine-methanol (740 mg, 3.7 mmol) and THF (9 mL). The mixture was stirred to dissolve the solids and cooled to −20° C. DIAD (738 μL, 3.8 mmol) in THF (4 mL) was added over 2 h using a syringe pump, keeping the reaction temperature between −10 to −20° C. The reaction was warmed to RT and stirred for 19 h. The THF was stripped and the crude mixture was dissolved in EtOAc, washed with water and brine, dried with $MgSO_4$, filtered and evaporated. The mixture was purified by column chromatography using EtOAc/hexanes as the eluant. The title compound was obtained as a viscous liquid.

Step D: R-2-(5-Amino-2-pentafluoroethyl-phenoxymethyl)-1-(tert-butoxycarbonyl)pyrrolidine.

The title compound was prepared similarly to the compound in Example 3, Step B.

Step E: R-2-(5-Thioisocyanato-2-pentafluoroethyl-phenoxymethyl)-1-(tert-butoxycarbonyl)pyrrolidine.

A mixture of R-2-(5-amino-2-pentafluoroethyl-phenoxymethyl)-1-(tert-butoxycarbonyl)pyrrolidine (Step C) (165.0 mg, 0.4 mmol) in $CH_2Cl_2$ (5 mL) was cooled in an ice bath and 1,1'-thiocarbonyldiimidazole (75 mg, 0.42 mmol) was added. The ice bath was removed, the reaction was warmed to RT and stirred until the aniline was consumed (as judged by TLC). The reaction mixture was filtered through a pad of silica gel using $CH_2Cl_2$ as the eluant, and concentrated in vacuo to yield the title compound as a mixture with the imidazole. The mixture was used directly in the next reaction.

Step F: R-2-{5-[5-(2-Methylcarbamoyl-pyridin-4-yloxy)-1H-benzimidazol-2-ylamino]-2-pentafluoroethyl-phenoxymethyl}-1-(tert-butoxycarbonyl)pyrrolidine.

The title compound was prepared similarly to the procedure described for Example 2, Step C and purified by column chromatography using 0-50% of a 90:10:1 ($CH_2Cl_2$:MeOH:$NH_4OH$) solution as the eluant to yield a white solid.

Step G: 4-{2-R-[4-Pentafluoro-3-(pyrrolidin-2-ylmethoxy)-phenylamino]-1H-benzimidazol-5-yloxy}-pyridine-2-carboxylic acid methylamide.

To a solution of R-2-{5-[5-(2-methylcarbamoyl-pyridin-4-yloxy)-1H-benzimidazol-2-ylamino]-2-pentafluoroethyl-phenoxymethyl}-1-(tert-butoxycarbonyl)pyrrolidine (Step E, 89 mg) in $CH_2Cl_2$ (2 mL), TFA (1 mL) was added and stirred at RT for 1 h. The mixture was diluted with $CH_2Cl_2$ (15 mL) and neutralized with solid $NaHCO_3$, then 2N NaOH. The mixture was transferred to a seperatory funnel and the layers separated. The aqueous layer was extracted with EtOAc and the combined organic layers were dried with $MgSO_4$, filtered

EXAMPLE 6

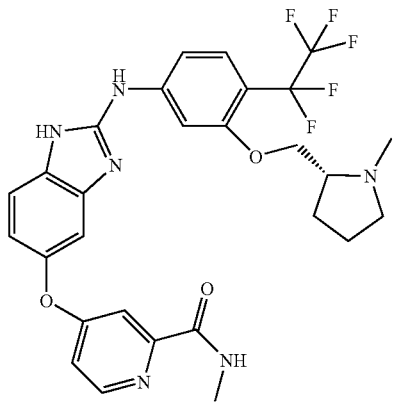

R-4-{2-[3-(1-Methyl-pyrrolidin-2-ylmethoxy)-4-pentafluoroethyl-phenylamino]-1H-benzimidazol-5-yloxy}-pyridine-2-carboxylic acid methylamide Step A: R-2-(5-Nitro-2-pentafluoroethyl-phenoxymethyl)-pyrrolidine.

To a solution of 2-(5-nitro-2-pentafluoroethyl-phenoxymethyl)-1-(tert-butoxycarbonyl)pyrrolidine (Example 5, Step C) in $CH_2Cl_2$ (5 mL), TFA (2.5 mL) was added and stirred at RT for 1 h. The mixture was diluted with $CH_2Cl_2$ (20 mL) and neutralized with sat $NaHCO_3$, then 2 N NaOH. The mixture was transferred to a seperatory funnel and the layers separated. The aqueous layer was extracted with EtOAc and the combined organic layers were dried with $MgSO_4$, filtered and concentrated in vacuo to yield the title compound as a yellow solid.

Step B: R-1-Methyl-2-(5-nitro-2-pentafluoroethyl-phenoxymethyl)-pyrrolidine.

A solution of 2-(5-nitro-2-pentafluoroethyl-phenoxymethyl)-pyrrolidine, (Step A, est 603.0 mg, 1.8 mmol), formaldehyde (37% in $H_2O$, 1 mL), and $NaBH(OAc)_3$ (600 mg, 2.8 mmol) in $CH_2Cl_2$ (25 mL) was stirred at RT for 15 h. The reaction was quenched with water and the organic layer was washed with 2 N NaOH. The organic layer was dried with $Na_2SO_4$, filtered and evaporated to give the title compound.

Step C: R-1-Methyl-2-(5-amino-2-pentafluoroethyl-phenoxymethyl)-pyrrolidine.

The title compound was prepared similarly to the compound in Example 3, Step B.

Step D: R-4-{2-[3-(1-Methyl-pyrrolidin-2-ylmethoxy)-4-pentafluoroethyl-phenylamino]-1H-benzimidazol-5-yloxy}-pyridine-2-carboxylic acid methylamide.

The title compound was prepared similarly to the procedure described for Example 2, Step D and purified by column chromatography using 0-50% of a 90:10:1 ($CH_2Cl_2$:MeOH:$NH_4OH$) solution as the eluant to yield an off-white solid. M+H 591.2, Calc'd for $C_{28}H_{27}F_5N_6O_3$— 590.21.

EXAMPLE 7

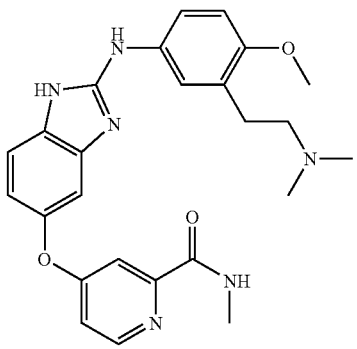

4-{2-[3-(2-Dimethylamino-ethyl)-4-methoxy-phenylamino]-1H-benzimidazol-5-yloxy}-pyridine-2-carboxylic acid methylamide Step A: (2-Methoxy-5-nitrophenyl)-acetonitrile.

2-Bromomethyl-1-methoxy-4-nitro-benzene (25 g) was dissolved in warm EtOH (45 mL) and stirred while slowly adding a solution of NaCN (6.0 g in 12 mL $H_2O$) at 70° C. After the addition was complete, the reaction was stirred at 70° C. for 90 min. The inorganic solid, which separated on cooling, was collected and washed well with $CH_3CN$. The $CH_3CN$ filtrate was filtered again giving further inorganic solid, and again washed with $CH_3CN$. The final $CH_3CN$ filtrate was evaporated giving a red-brown solid. This solid was triturated with $CH_2Cl_2$ until the washings were colorless. Evaporation of the $CH_2Cl_2$ filtrate gave (2-methoxy-5-nitrophenyl)-acetonitrile as a red-brown solid, which was used without further purification.

Step B: 2-(2-Methoxy-5-nitrophenyl)acetic acid.

The crude (2-methoxy-5-nitrophenyl)-acetonitrile (Step A) was stirred, heated with 20 mL of 12 M HCl at reflux for 3 h, then at 60° C. overnight. After cooling, the product was extracted in $CH_2Cl_2$ (3×40 mL), washed with $H_2O$ then extracted into 3 M NaOH. The basic extracts were washed with $CH_2Cl_2$, acidified (6 M HCl) and the solid was collected, washed well with water and dried in air giving pure 2-(2-methoxy-5-nitrophenyl)acetic acid. Evaporation of the $CH_2Cl_2$ extracts and retreating the residual solid with 50 mL of 12 M HCl/20 mL water at reflux for 6 h followed by purification as above gave additional pure 2-(2-methoxy-5-nitrophenyl)acetic acid.

Step C: 2-(2-Methoxy-5-nitrophenyl)-N,N-dimethyl-acetamide.

2-(2-Methoxy-5-nitrophenyl)acetic acid (17.1 g, 1 eq, Step B), EDC (18.6 g, 1.2 eq.), $Et_3N$ (9.8 g, 13.6 mL, 1.2 eq) and dimethylamine hydrochloride (7.9 g, 1.2 eq.) in 150 mL of $CH_2Cl_2$ were stirred together with exclusion of air overnight. $CH_2Cl_2$ (150 mL) was added and the mixture was washed twice with 1M HCl, twice with 1M NaOH, $H_2O$ and brine. Removal of the solvent under reduced pressure followed by silica gel chromatography (90:10 $CH_2Cl_2$:EtOAc) afforded pure 2-(2-methoxy-5-nitrophenyl)-N,N-dimethyl-acetamide as a white solid.

Step D: [2-(2-Methoxy-5-nitrophenyl)-ethyl]-dimethyl-amine.

2-(2-Methoxy-5-nitrophenyl)-N,N-dimethyl-acetamide (15.0 g, Step C) was added to 126 mL of 1M $BH_3$-THF (2 eq.) under $N_2$ and the resulting mixture was heated at reflux. After 2 h, additional $BH_3$-THF was added (120 mL) followed by 0.2 mL of boron trifluoride etherate and heating was continued for 13 h. Evaporation and azeotroping the residue from MeOH 3× gave a semi-solid residue which was washed with MeOH and filtered to give the boric acid salt of [2-(2-methoxy-5-nitrophenyl)-ethyl]-dimethyl-amine as a white solid.

Step E: 3-(2-Dimethylamino-ethyl)-4-methoxy-phenylamine.

To a solution of [2-(2-methoxy-5-nitrophenyl)-ethyl]-dimethyl-amine (1.0 g, Step D) dissolved in EtOH (20 mL) was added 10% Pd/C (0.1 g). The reaction vessel was capped with a rubber septum and $H_2$ gas was introduced through a balloon/needle. The reaction was stirred vigorously overnight at RT, and which time it was filtered through sand/Celite®. Concentration of the crude mixture provided a beige oil which was purified by chromatography on silica gel (97:3 $CH_2Cl_2$:MeOH) to afford pure 3-(2-dimethylamino-ethyl)-4-methoxy-phenylamine as a white solid.

Step F: 4-{2-[3-(2-Dimethylamino-ethyl)-4-methoxy-phenylamino]-1H-benzimidazol-5-yloxy}-pyridine-2-carboxylic acid methylamide The title compound was prepared similarly to the procedure outlined above in Preparation III, Example 1. MS (MH$^+$)= 461.1, MW: 460.21 Calc'd for: $C_{25}H_{28}N_6O_3$.

EXAMPLE 8

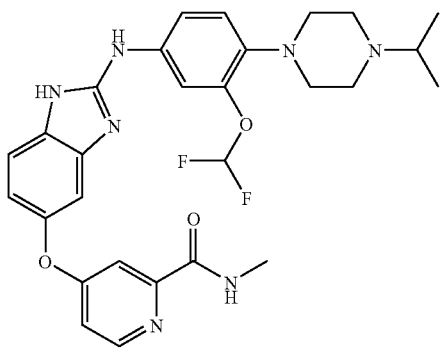

4-{2-[3-Difluoromethoxy-4-(4-isopropylpiperazin-1-yl)-phenylamino]-1H-benzimidazol-5-yloxy}-pyridine-2-carboxylic acid methylamide Step A: 1-Bromo-2-difluoromethoxy-4-nitro-benzene.

To a $N_2$ purged round bottom flask was added 2-bromo-5-nitrophenol (29.0 g, 133 mmol, 1.0 eq.) followed by 16.8 mL (133 mmol, 1.0 eq) of ethyl chlorodifluoroacetate and 18.8 g of $K_2CO_3$ (133 mmol, 1.0 eq.). Anhydrous DMF (300 mL) was added and the mixture was stirred at 70° C. for 5 h. The mixture was cooled to RT and the solvent was removed. The obtained crude mixture was dissolved in $CH_2Cl_2$ (500 mL) and washed with 1 N NaOH (aq.). The organic layer was dried (MgSO$_4$), filtered and evaporated. The crude material was further purified by column chromatography (0-5% EtOAc in hexanes) providing pure 1-bromo-2-difluoromethoxy-4-nitro-benzene.

Step B: 1-(2-Difluoromethoxy-4-nitro-phenyl)-4-isopropyl-piperazine.

1-Bromo-2-difluoromethoxy-4-nitro-benzene (Step A, 2.0 g, 7.5 mmol, 1.0 eq.) and N-(2-propyl)piperazine (0.85 mL, 9.7 mmol, 1.3 eq.) were dissolved in 20 mL of DMSO. $K_2CO_3$ (1.5 g, 11.2 mmol, 1.5 eq.) and Bu$_4$N$^+$Br$^-$ (240 mg, 0.75 mmol, 0.1 eq.) were added and the mixture was heated to 120° C. The mixture was stirred for 3 h and cooled to RT, poured into $H_2O$ (200 mL) and 6 N HCl (20 mL). The aqueous solution was washed with EtOAc, and alkalinized with 6 N NaOH then extracted with EtOAc. The combined organic layers were dried (MgSO$_4$), filtered and concentrated. The crude material was further purified by column chromatography (0-100% EtOAc in hexanes) providing pure 1-(2-difluoromethoxy-4-nitro-phenyl)-4-isopropyl-piperazine.

Step C: 3-Difluoromethoxy-4-(4-isopropyl-piperazin-1-yl)-phenylamine.

1-(2-Difluoromethoxy-4-nitro-phenyl)-4-isopropyl-piperazine (Step B, 0.5 g, 1.9 mmol, 1.0 eq.) was dissolved in MeOH (10 mL). The atmosphere was replaced by argon. A catalytic amount of 10% Pd/C was added and the argon was replaced by a $H_2$ atmosphere. The mixture was stirred for 16 h at RT at balloon pressure. The Pd/C was removed by filtration and the solvent was removed under vacuum to yield 3-difluoromethoxy-4-(4-isopropyl-piperazin-1-yl)-phenylamine. The crude material was used as is in the next step.

Step D: 4-{2-[3-Difluoromethoxy-4-(4-isopropyl-piperazin-1-yl)-phenylamino]-1H-benzimidazol-5-yloxy}-pyridine-2-carboxylic acid methylamide.

The title compound was prepared similarly to the procedure outlined above in Preparation III and Example 1. MS m/z=552.3 (M+H)+Calc'd for $C_{28}H_{31}N_7O_3$: 551.25.

EXAMPLE 9

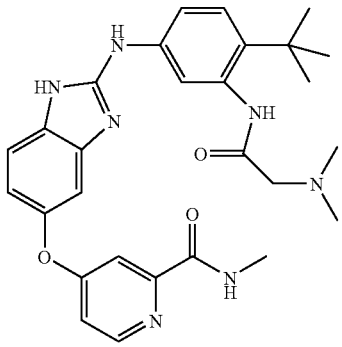

4-{2-[4-tert-Butyl-3-(2-dimethylamino-acetylamino)-phenylamino]-1H-benzimidazol-5-yloxy}-pyridine-2-carboxylic acid methylamide Step A: 5-Nitro-2-t-butylaniline.

Concentrated $H_2SO_4$ (1 L) was cooled to −10° C. with a dry ice/i-PrOH bath in a 2 L 3-neck round bottom flask fitted with a mechanical stirrer and temperature probe. 2-t-Butylaniline (109 g, 730 mmol) was added, giving a clumpy solid. Once the temperature stabilized at −10° C., KNO$_3$ (101 g, 1001 mmol) was added portion wise, as a solid, for 4 h, maintaining the temperature between −20 and −5° C. Once all of the KNO$_3$ was added, the reaction was stirred overnight with gradual warming to RT. The reaction was quenched by diluting with water and extracted with EtOAc (3×). The EtOAc extracts were washed multiple times with saturated NaHCO$_3$ (aq), until gas evolution ceased, then with brine. The EtOAc extracts were combined, dried over anh. Na$_2$SO$_4$, filtered and concentrated under reduced pressure giving a black oil. The oil was eluted through a 36×7 cm column of silica gel with a 5%; 10%; 15%; 25%; and 50% EtOAc:Hexanes step gradient (2 L each step) giving a red solid.

Step B: 2-Bromo-N-(2-tert-butyl-5-nitro-phenyl)-acetamide.

5-Nitro-2-t-butylaniline (Step A, 70 g, 359 mmol) and a catalytic amount of DMAP were dissolved in THF (1.5 L) under $N_2$. $Et_3N$ (109 g, 1077 mmol) was added and the solution was cooled to 0° C. Bromoacetyl bromide (207 g, 1023 mmol) was added and the reaction was gradually warmed to RT with stirring overnight. The reaction was partially concentrated under reduced pressure, treated with water and extracted with EtOAc (3×). The EtOAc extracts were washed with brine, combined, dried over anhydrous $Na_2SO_4$, filtered and concentrated under reduced pressure, giving a black oil. This oil was eluted through a 38×7 cm column of silica gel with 95:5:0.5 $CH_2Cl_2$:MeOH:$NH_4$OH(aq) eluant giving a brown solid.

Step C: N-(2-tert-Butyl-5-nitro-phenyl)-2-dimethylamino-acetamide.

2-Bromo-N-(2-tert-butyl-5-nitro-phenyl)-acetamide (Step B, 80 g, 253 mmol) and $K_2CO_3$ (70 g, 506 mmol) were combined in a 3 L 3-neck round bottom flask fitted with a mechanical stirrer, $N_{2(g)}$ inlet, and pressure equalizing addition funnel. THF (1.75 L) was added and the mixture cooled to 0° C. under $N_{2(g)}$. N,N-Dimethylamine (400 mL of a 2 M solution in THF, 800 mmol) was added to the mixture through the pressure equalizing addition funnel over 30 min. The mixture was gradually warmed to RT with stirring overnight. The reaction was quenched by filtering under vacuum and concentrating the filtrate under reduced pressure. The recovered material was eluted through a 36×7 cm column of silica gel with 50% EtOAc:Hexanes giving a brown solid.

Step D: N-(5-Amino-2-tert-butyl-phenyl)-2-dimethylamino-acetamide.

N-(2-tert-Butyl-5-nitro-phenyl)-2-dimethylamino-acetamide (25.8 g, 92 mmol) was dissolved into EtOH (1.4 liters) and 1,4-dioxane (200 mL). The solution was degassed under vacuum with stirring. 10% Pd/C (2.5 g) was added (as a slurry in EtOH). The mixture was degassed again, then the reaction vessel was charged with $H_2$ gas (balloon) and stirred overnight at RT. The reaction was filtered through Celite® with MeOH and the filtrate was concentrated under reduced pressure. The recovered material was eluted through a 36×7 cm column of silica gel with a 97.5:2.5:0.25 and 95:5:0.5 $CH_2Cl_2$:MeOH:$NH_4$OH(aq) step gradient giving a brown solid.

Step E: 4-{2-[4-tert-Butyl-3-(2-dimethylamino-acetylamino)-phenylamino]-1H-benzimidazol-5-yloxy}-pyridine-2-carboxylic acid methylamide.

The title compound was prepared similarly to the procedure outlined above in Preparation III and Example 1. MS (MH$^+$)=516.3, MW: 515.26 Calc'd for: $C_{28}H_{33}N_7O_3$.

EXAMPLE 10

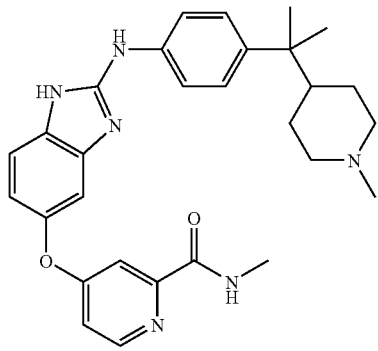

4-(2-{4-[1-Methyl-1-(1-methyl-piperidin-4-yl)-ethyl]-phenylamino}-1H-benzimidazol-5-yloxy)-pyridine-2-carboxylic acid methylamide Step A: 1-Methyl-4-[1-methyl-1-(4-nitro-phenyl)-ethyl]-pyridinium iodide.

4-(4-Nitrobenzyl)pyridine (64 g, 300 mmol) and $Bu_4NI$ (6 g, 16.2 mmol) were dissolved in $CH_2Cl_2$ (500 mL) and the solution was suspended with NaOH (aq. 5N, 450 mL). With vigorous stirring, MeI (213 g, 1500 mmol) was added. The resulting solution was placed under $N_2$ and stirred vigorously at RT for 60 h until the blue color disappeared. (MS: M$^+$=257). The mixture was used in the next step without further purification.

Step B: 1-Methyl-4-[1-methyl-1-(4-nitro-phenyl)-ethyl]-1,2,3,6-tetrahydro-pyridine.

1-Methyl-4-[1-methyl-1-(4-nitro-phenyl)-ethyl]-pyridinium (Step A) was treated with DEA (100 mL) in MeOH (300 mL) for 2 h. $NaBH_4$ (19 g, 500 mmol) was added in small portions. The resulting mixture was stirred for 30 min at RT, then partitioned between $CH_2Cl_2$/$H_2O$ (500 mL/500 mL). The organic layer was collected and the upper layer was washed with $CH_2Cl_2$ (300 mL×3). The combined organic layer was washed with brine then concentrated in vacuo. The residue was purified on a silica washed-column (7% TEA in EtOAc). The desired fractions were combined and concentrated under vacuum to give the desired compound as a dark gray solid. (MS: M+1=261).

Step C: 4-[1-Methyl-1-(1-methyl-piperidin-4-yl)-ethyl]-phenylamine.

1-Methyl-4-[1-methyl-1-(4-nitro-phenyl)-ethyl]-1,2,3,6-tetrahydro-pyridine (Step B) was hydrogenated with Pd/C 10% at atmospheric pressure at RT in EtOH to yield the title compound.

Step D: 4-(2-{4-[1-Methyl-1-(1-methyl-piperidin-4-yl)-ethyl]-phenylamino}-1H-benzimidazol-5-yloxy)-pyridine-2-carboxylic acid methylamide.

The title compound was prepared according the procedure similar to that described for Preparation III and Example 1. MS (MH$^+$)=499.2; Calc'd 498.27 for $C_{29}H_{34}N_6O_2$.

EXAMPLE 11

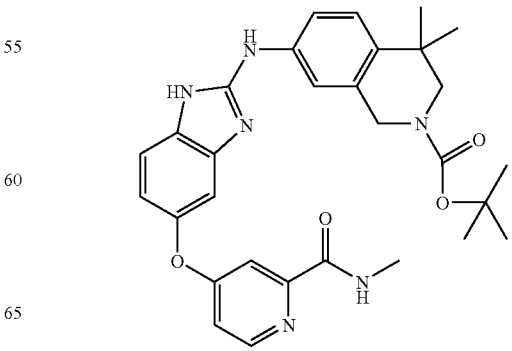

2-tert-Butoxycarbonyl-4,4-dimethyl-7-[5-(2-methyl-carbamoyl-pyridin-4-yloxy)-1H-benzimidazol-2-ylamino]-3,4-dihydro-1H-isoquinoline Step A: (2-Chloro-5-nitro-benzyl)-(2-methyl-allyl)-amine.

To a solution of 2-chloro-5-nitrobenzaldehyde (25 g) in EtOH (200 mL) was added 3-methylallylamine (10.6 g, 1.1 eq). HOAc (9 g) was added to the solution. The mixture was stirred at 20~25° C. for 3 h. NaBH(OAc)$_3$ (43 g, 1.5 eq) was added in one portion at ~5° C. The mixture was warmed to RT in 30 min and stirred for 1 h. The EtOH was removed under reduced pressure and saturated Na$_2$CO$_3$ aqueous solution (200 mL) was added. The mixture was extracted with toluene (100 mL). To the toluene solution was added 5 N HCl in IPA (20 mL) at ~5° C. in 1 h. The mixture was stirred for 1 h. The solids were filtered off, and dried under vacuum.

Step B: N-Boc-(2-Chloro-5-nitro-benzyl)-(2-methyl-allyl)-amine.

To a mixture of the (2-chloro-5-nitro-benzyl)-(2-methyl-allyl)-amine (12 g) in THF (120 mL) and 2N NaOH aqueous solution (25 mL) was added. Boc anhydride (11.4 g, 1.2 eq) was added. The mixture was stirred at 25° C. for 3 h. The THF was removed under reduced pressure and the mixture was extracted with toluene. The toluene was removed under reduced pressure to give an oil residue.

Step C: 2-Boc-4,4-dimethyl-7-nitro-3,4-dihydro-2H-isoquinoline.

To a solution of the residue Step B (10 g) in DMF (100 mL) was added Pd(OAc)$_2$ (0.6 g), sodium formate (2.2 g), NaOAc (6.1 g) and tetraethylammonium hydrate (5.4 g). N$_2$ was bubbled (under surface) through the mixture for 30 min. The mixture was heated to 83-85° C. for 4.5 h. The mixture was cooled to ~25° C. and filtered through Celite® bed. The Celite® bed was washed with water (300 mL) and EtOAc (200 mL). The organic phase was separated.

Step D: 2-Boc-4,4-dimethyl-7-amino-3,4-dihydro-2H-isoquinoline.

To the organic phase (Step C) was added 10% Pd/C (wet) (1.2 g). H$_2$ (1 atm) was applied. The mixture was stirred overnight. The mixture was filtered through Celite® bed. The bed was washed with EtOAc (50 mL). The solvent was removed under reduced pressure to give an oil residue that solidified upon standing.

Step E: 2-tert-Butoxycarbonyl-4,4-Dimethyl-7-[5-(2-methylcarbamoyl-pyridin-4-yloxy)-1H-benzimidazol-2-ylamino]-3,4-dihydro-1H-isoquinoline.

The title compound was prepared according the procedure similar to that described for Preparation III and Example 1. MS (MH$^+$)=543.30; Calc'd 542.26 for $C_{30}H_{34}N_6O_4$.

EXAMPLE 12

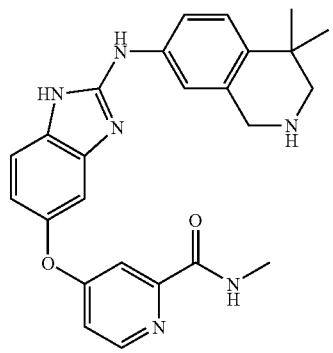

4-[2-(4,4-Dimethyl-1,2,3,4-tetrahydroisoquinolin-7-ylamino)-1H-benzimidazol-5-yloxy]-pyridine-2-carboxylic acid methylamide To a solution of 2-tert-butoxycarbonyl-4,4-dimethyl-7-[5-(2-methylcarbamoyl-pyridin-4-yloxy)-1H-benzimidazol-2-ylamino]-3,4-dihydro-1H-isoquinoline (230 mg) (Example 11) in CH$_2$Cl$_2$ (10 mL) was added TFA (1 mL). The mixture was stirred at RT for 2 h. Solvent was evaporated, aqueous NaHCO$_3$ solution was added, and the mixture was extracted with EtOAc. The organic phase was dried, filtered and evaporated to give the title compound. MS (MH$^+$)=443.2; Calc'd 442.21 for $C_{25}H_{26}N_6O_2$.

EXAMPLE 13

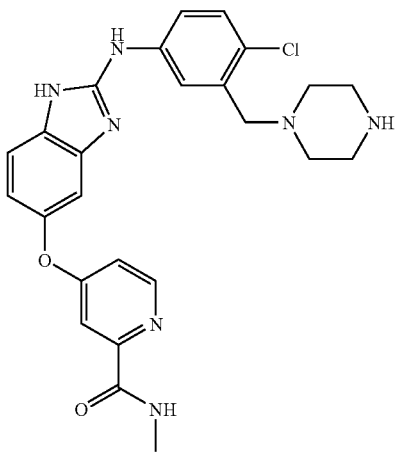

4-[2-(4-Chloro-3-piperazin-1-ylmethyl-phenylamino)-1H-benzimidazol-5-yloxy]-pyridine-2-carboxylic acid methylamide Step A: 4-{2-Chloro-5-[5-(2-methylcarbamoyl-pyridin-4-yloxy)-1H-benzimidazol-2-ylamino]-benzyl}-piperazino-1-carboxylic acid tert-butyl ester The title compound was prepared by a method described in Example 2, Steps 3 and 4. MS (MH$^+$)=592.2; Calc'd 592.10 for $C_{30}H_{34}ClN_7O_4$.

Step B: 4-[2-(4-Chloro-3-piperazin-1-ylmethyl-phenylamino)-1H-benzimidazol-5-yloxy]-pyridine-2-carboxylic acid methyl amide 4-{2-Chloro-5-[5-(2-methylcarbamoyl-pyridin-4-yloxy)-1H-benzimidazol-2-ylamino]-benzyl}-piperazino-1-carboxylic acid tert-butyl ester (0.228 g, 0.385 mmol) was dissolved in 10 mL CH$_2$Cl$_2$ and treated with 5 mL TFA. After stirring at RT for 1.5 h, the reaction was concentrated in vacuo and dissolved in EtOAc and 6 N NaOH. The layers were extracted, and the organic layer was washed twice with 6 N NaOH and once with a mix of brine and 6 N NaOH. All aqueous layers were back-extracted once with EtOAc. The combined organic layers were dried over Na$_2$SO$_4$, filtered, and concentrated in vacuo, to yield the title compound. MS (MH$^+$)=492.2; MW Calc'd 491.18 for $C_{25}H_{26}ClN_7O_2$.

EXAMPLE 13a to 13e

The following compounds were prepared similarly to the procedure outlined above in Example 2, step using the corresponding isothiocyanates:

| Ex. | Structure | Mol. Formula | Mass | MS (MH+) |
|---|---|---|---|---|
| 13a | 4-{2-[3-(2-Dimethylamino-ethoxy)-4-trifluoromethyl-phenyl-amino]-1H-benzimidazol-5-yloxy}-pyridine-2-carboxylic acid methyl-amide | $C_{25}H_{25}F_3N_6O_3$ | 514.19 | 515.0 |
| 13b | 4-{2-[4-Chloro-3-(4-methyl-piperazin-1-ylmethyl)-phenyl-amino]-1H-benzimidazol-5-yloxy}-pyridine-2-carboxylic acid methylamide | $C_{26}H_{28}ClN_7O_2$ | 505.20 | 506.4 |
| 13c | 4-{2-[3-(1-Methyl-pyrrolidin-2-ylmethoxy)-4-trifluoromethyl-phenylamino]-1H-benzimidazol-5-yloxy}-pyridine-2-carboxylic acid methylamide | $C_{27}H_{27}F_3N_6O_3$ | 540.21 | 541.2 |
| 13d | 4-{2-[4-Chloro-3-(4-isopropyl-piperazin-1-ylmethyl)-phenyl-amino]-1H-benzimidazol-5-yloxy}-pyridine-2-carboxylic acid methylamide | $C_{28}H_{32}ClN_7O_2$ | 533.23 | 534.2 |

| Ex. | Structure | Mol. Formula | Mass | MS (MH+) |
|---|---|---|---|---|
| 13e | 4-{2-[4-Chloro-3-(4-methanesulfonyl-piperazin-1-ylmethyl)-phenylamino]-1H-benzimidazol-5-yloxy}-pyridine-2-carboxylic acid methylamide | C$_{26}$H$_{28}$ClN$_7$O$_4$S | 569.16 | 570.3 |

EXAMPLE 14

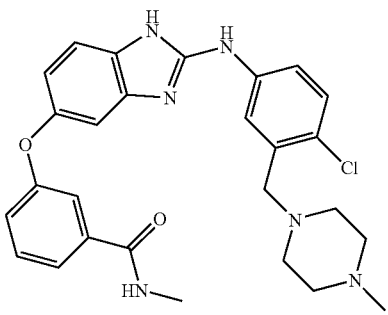

3-{2-[4-Chloro-3-(4-methyl-piperazin-1-ylmethyl)-phenylamino]-1H-benzimidazol-5-yloxy}-N-methyl-benzamide Step A: 3-Hydroxy-N-methylbenzamide To a solution of 3-hydroxybenzoic acid (10 g, 72 mmol, 1.0 eq.) in 100 mL of anhydrous dioxane was added SOCl$_2$ (6.5 mL, 72 mmol, 1.0 eq.). The solution was heated to reflux and stirred for 4 h. The solvent was removed and the crude was dissolved in anhydrous THF (100 mL). A solution of 2 M CH$_3$NH$_2$ in THF (7.2 mL, 144 mmol, 2.0 eq.) was added upon which a white suspension was formed. The solvent was evaporated and the residue was dissolved in MTBE, washed with sat. NH$_4$Cl (aq.). The organic layer was dried (MgSO$_4$), filtered and concentrated. Further purification by column chromatography (0-100% EtOAc in hexanes) yielded 3-hydroxy-N-methyl-benzamide.

Step B: 3-(4-Amino-3-nitro-phenoxy)-N-methyl-benzamide

To a solution of 3-hydroxy-N-methyl-benzamide (Step A, 700 mg, 4.6 mmol, 1.0 eq.) in anhydrous DMF (10 mL) was added NaH (200 mg, 5.1 mmol, 1.1 eq.). The reaction was stirred for 10 min. at RT after which 4-chloro-2-nitro-phenylamine (2.0 g, 11.6 mmol, 2.5 eq.) was added. The resulting mixture was heated to 80° C. for 4 h. The reaction was quenched with NaHCO$_3$ (aq.), diluted with CH$_2$Cl$_2$ (50 mL), and washed with 1 N NaOH (25 mL). The organic layer was dried over MgSO$_4$, filtered and concentrated. The crude was further purified by column chromatography (0-100% EtOAc in hexanes) to give pure 3-(4-amino-3-nitro-phenoxy)-N-methyl-benzamide.

Step C: 3-(3,4-Diamino-phenoxy)-N-methyl-benzamide 3-(4-Amino-3-nitro-phenoxy)-N-methyl-benzamide (Step B, 0.5 g, 1.7 mmol, 1.0 eq.) was dissolved in MeOH (10 mL) and the atmosphere was replaced by argon. A catalytic amount of 10% Pd/C was added and the argon was replaced by a H$_2$ atmosphere. The mixture was stirred for 16 h at RT at atmospheric pressure. The Pd/C was filtered off and the obtained 3-(3,4-diamino-phenoxy)-N-methyl-benzamide was used crude in the next step.

Step D: 3-{2-[4-Chloro-3-(4-methyl-piperazin-1-ylmethyl)-phenylamino]-1H-benzimidazol-5-yloxy}-N-methyl-benzamide.

3-(3,4-Diamino-phenoxy)-N-methyl-benzamide (Step C, 400 mg, 1.5 mmol, 1.0 eq.) was dissolved in anh. CH$_3$CN (10 mL) and a solution of 1-(2-chloro-5-isothiocyanato-benzyl)-4-methyl-piperazine (330 mg, 1.2 mmol, 0.8 eq.) in CH$_3$CN (10 mL) was added dropwise. The reaction was stirred at RT for 2 h. EDC (240 mg, 1.3 mmol, 0.9 eq.) was added, the mixture was heated to 80° C. and stirred for 2 h. The CH$_3$CN was evaporated and the crude compound was dissolved in CH$_2$Cl$_2$, washed with water and sat. NaHCO$_3$ (aq.). The organic layer was dried (MgSO$_4$), filtered and concentrated. Further purification by column chromatography (0-10% EtOH/CH$_2$Cl$_2$, two runs were required) gave pure 3-{2-[4-chloro-3-(4-methyl-piperazin-1-ylmethyl)-phenylamino]-1H-benzimidazol-5-yloxy}-N-methyl-benzamide. MS m/z=505.2 (M+H)$^+$; MW Calc'd for C$_{27}$H$_{29}$N$_6$O$_2$: 504.20.

EXAMPLE 15

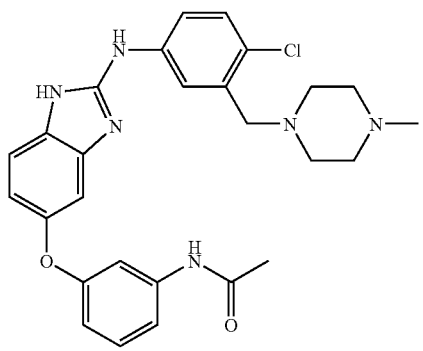

N-(3-{2-[4-Chloro-3-(4-methyl-piperazin-1-ylmethyl)-phenylamino]-1H-benzimidazol-5-yloxy}-phenyl)-acetamide Step A: N-[3-(3,4-Dinitro-phenoxy)-phenyl]-acetamide To a mixture of 3,4-dinitrofluorobenzene (1.0 g, 5.4 mmol, 1.0 eq.) and 3-acetamidophenol (0.8 g, 5.4 mmol, 1.0 eq.) in 10 mL of anhydrous DMF, $K_2CO_3$ (0.7 g, 5.4 mmol, 1.0 eq) was added. The reaction mixture was heated to 120° C. and stirred for 16 h. The mixture was cooled to RT and EtOAc was added (100 mL). After washing with $H_2O$ (100 mL), the organic layer was dried ($MgSO_4$), filtered and concentrated. The resulting crude material was purified by column chromatography (20-100% EtOAc in hexanes) to obtain pure N-[3-(3,4-dinitro-phenoxy)-phenyl]-acetamide.

Step B: N-[3-(3,4-Diamino-phenoxy)-phenyl]-acetamide.

N-[3-(3,4-Dinitro-phenoxy)-phenyl]-acetamide (Step A, 0.4 g, 1.3 mmol, 1.0 eq.) was dissolved in MeOH (10 mL) and the atmosphere was replaced by argon. A catalytic amount of 10% Pd/C was added and the argon was replaced by a $H_2$ atmosphere. The mixture was stirred for 16 h at RT at balloon pressure. The Pd/C was filtered and the obtained N-[3-(3,4-diamino-phenoxy)-phenyl]-acetamide was used crude in the next step. MS m/z=259.1 (M+H)+Calc'd for $C_{14}H_{15}N_3O_2$: 257.29.

Step C: N-(3-{2-[4-Chloro-3-(4-methyl-piperazin-1-ylmethyl)-phenylamino]-1H-benzimidazol-5-yloxy}-phenyl)-acetamide.

A solution of N-[3-(3,4-diamino-phenoxy)-phenyl]-acetamide (Step B, 320 mg, 1.2 mmol, 1.0 eq.) in 20 mL of anhydrous $CH_3CN$ was added drop-wise to a solution of 1-(2-chloro-5-isothiocyanato-benzyl)-4-methyl-piperazine (300 mg, 1.2 mmol, 1.0 eq.) in 10 mL of $CH_3CN$. The reaction was stirred for 2 h at RT. EDC (360 mg, 1.9 mmol, 1.5 eq.) was added and the reaction was heated to 80° C. and stirred for 1 h. The mixture was cooled and concentrated. The residue was dissolved into EtOAc and washed with $H_2O$ and sat. $NaHCO_3$ (aq.). The organic layer was dried ($MgSO_4$), filtered and concentrated. The crude was further purified by column chromatography (0-10% MeOH/$CH_2Cl_2$ with 1% $NH_4OH$) followed by recrystallization from $CH_2Cl_2$ to give pure N-(3-{2-[4-chloro-3-(4-methyl-piperazin-1-ylmethyl)-phenylamino]-1H-benzimidazol-5-yloxy}-phenyl)-acetamide. MS m/z=506.2 (M+H)+; Calc'd for $C_{27}H_{29}N_6O_2$: 504.20.

EXAMPLE 16

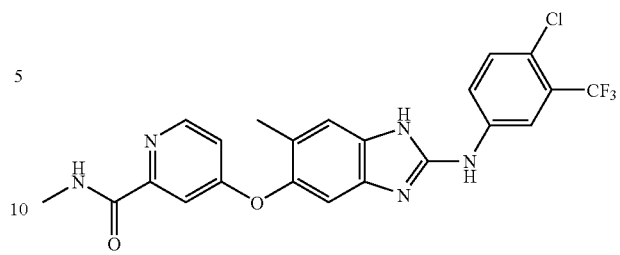

4-[2-(4-Chloro-3-trifluoromethyl-phenylamino)-6-methyl-1H-benzimidazol-5-yloxy]-pyridine-2-carboxylic acid methylamide Step A: 2-methyl-4,5-dinitrophenol.

A solution of $HNO_3$ (27 mL, 70% solution) and $H_2O$ (14 mL) was cooled using an ice bath and 2-methyl-5-nitrophenol (10 g, 65 mmol) was added slowly, followed by $NaNO_3$ (90 mg, 1.3 mmol). The reaction was stirred and warmed to RT. After 4 h, $H_2O$ was added and the reaction was filtered to collect a yellow solid. This yellow solid was purified by titration with $CH_2Cl_2$ to yield the title compound as a solid that is 98% the desired isomer.

Step B: 4-(4,5-Dinitro-2-methyl-phenoxy)-pyridine-2-carboxylic acid methylamide.

2-Methyl-4,5-dinitrophenol (Step A, 1.34 g, 6.77 mmol) and 4-chloro-pyridine-2-carboxylic acid methylamide (1.16 g, 6.77 mmol) were combined and heated at 160-180° C. (round bottom flask with condenser). The reaction was cooled to RT, the contents of the flask were dissolved in $CH_2Cl_2$ and the organic layer washed with 2 N NaOH, then water. The organic layer was dried with $Na_2SO_4$, filtered and evaporated. The mixture was purified by column chromatography using EtOAc/hexanes as the eluant. The title compound was obtained as a tan solid.

Step C: 4-(4,5-Diamino-2-methyl-phenoxy)-pyridine-2-carboxylic acid methylamide

The title compound was prepared similarly to the compound in Example 2, Step B.

Step D: 4-[2-(4-Chloro-3-trifluoromethyl-phenylamino)-6-methyl-1H-benzimidazol-5-yloxy]-pyridine-2-carboxylic acid methylamide The title compound was prepared similarly to the procedure described for Example 2, Step C and purified by prep HPLC to yield a yellow solid. MS: (MH+) 475.9, MW Calc'd for $C_{22}H_{17}ClF_3N_5O_2$— 475.10.

EXAMPLE 17

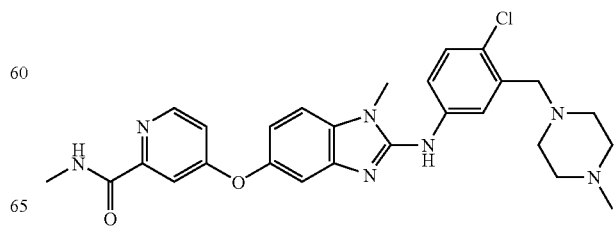

4-{2-[4-Chloro-3-(4-methyl-piperazin-1-ylmethyl)-phenylamino]-1-methyl-1H-benzimidazol-5-yloxy}-pyridine-2-carboxylic acid methylamide Step A: 3-(4-Amino-3-nitro-phenoxy)-N-methyl-benzamide.

A solution of 4-amino-3-nitrophenol (0.6 g, 3.84 mmol, 1.2 eq) in DMSO (2.75 mL, 5×) was treated with KOt-Bu (0.44 g, 3.84 mmol, 1.2 eq), and the mixture was stirred at RT for 2 h. The contents were treated with 4-chloro-N-methyl-2-pyridinecarboxamide (0.55 g, 3.2 mmol, 1.0 eq), $K_2CO_3$ (0.24 g, 1.7 mmol, 0.53 eq), and heated at 110° C. for 16 h. HPLC showed N-methylamide <2%. To the stirred mixture was added water (about 30 mL) slowly, and the compound precipitated. The solid was filtered off (slow filtration) and washed with water (about 60 mL). The filtrant was dried in a vacuum oven over night to give the title compound as a brown solid.

Step B: 4-(4-methylamino-3-nitrophenoxy)-pyridine-2-carboxylic acid methylamide.

To a flask containing $CH_3CN$ (50 mL) and HCl (6 N, 550 mL) 3-(4-amino-3-nitro-phenoxy)-N-methyl-benzamide (2.0 g, 6.9 mmol) was added and stirred at RT. To this suspension, formaldehyde (37% in water, 613 mL, 8.2 mmol) and $NaBH_3CN$ (477 mg, 7.6 mmol) were added. After 20 h, the mixture was diluted with EtOAc, the reaction filtered through Celite®, and the filtrate was concentrated in vacuo. The residue was purified by preparatory HPLC to yield the title compound as an orange, glassy solid.

Step C: 3-(3-Amino-4-methylamino-phenoxy)-N-methyl-benzamide

The title compound was prepared similarly to the compound in Example 2, Step B.

Step D: 4-{2-[4-Chloro-3-(4-methyl-piperazin-1-ylmethyl)-phenylamino]-1-methyl-1H-benzimidazol-5-yloxy}-pyridine-2-carboxylic acid methylamide The title compound was prepared similarly to the procedure described for Example 2, Step C to yield an off-white solid. MS (MH$^+$)=520.1, MW Calc'd for $C_{27}H_{30}ClN_7O_2$—519.21.

EXAMPLE 18

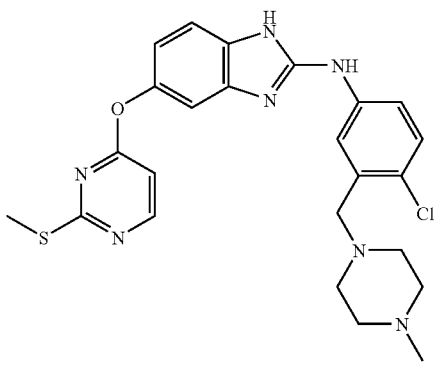

[4-Chloro-3-(4-methyl-piperazin-1-ylmethyl)-phenyl]-[5-(2-methylsulfanyl-pyrimidin-4-yloxy)-1H-benzimidazol-2-yl]-amine Step A: 4-(3,4-Dinitro-phenoxy)-2-methylsulfanyl-pyrimidine.

A mixture of 3,4-dinitrophenol (6.1 g, 38 mmol) and 2-thiomethyl-4-chloro-1,2-pyrimidine (7.02 g, 38 mmol) was heated at 150° C. for 2 h. The resulting solid was finely ground and washed several times with MTBE to remove traces of 2-thiomethyl-4-chloro-1,2-pyrimidine. The solid was suspended in 2 N NaOH and recovered by filtration. The solid was washed several times with water and dried under vacuum over $P_2O_5$ to give the desired 4-(3,4-dinitro-phenoxy)-2-methylsulfanyl-pyrimidine.

Step B: 4-(2-Methylsulfanyl-pyrimidin-4-yloxy)-benzene-1,2-diamine.

4-(3,4-Dinitro-phenoxy)-2-methylsulfanyl-pyrimidine (Step A, 1.0 g, 3.2 mmol, 1.0 eq.) was dissolved in MeOH (10 mL) and the atmosphere was replaced by argon. A catalytic amount of 10% Pd/C was added and the argon was replaced by a $H_2$ atmosphere. The mixture was hydrogenated for 2 h at RT at 60 psi using a Parr hydrogenation apparatus. More Pd/C was added and the mixture was hydrogenated for another 4 h at 60 psi. The Pd/C was removed by filtration. The crude aniline was purified using column chromatography (0-100% EtOAc in hexanes) to give 4-(2-methylsulfanyl-pyrimidin-4-yloxy)-benzene-1,2-diamine.

Step C: [4-Chloro-3-(4-methyl-piperazin-1-ylmethyl)-phenyl]-[5-(2-methylsulfanyl-pyrimidin-4-yloxy)-1H-benzimidazol-2-yl]-amine.

To a solution of 4-(2-methylsulfanyl-pyrimidin-4-yloxy)-benzene-1,2-diamine (Step B, 400 mg, 1.6 mmol, 1.0 eq.) in anhydrous $CH_3CN$ (30 mL) was added dropwise a solution of 1-(2-chloro-5-isothiocyanato-benzyl)-4-methyl-piperazine (900 mg [slightly contaminated with imidazole], 1.6 mmol, 1.0 eq.) in 20 mL of anhydrous $CH_3CN$. The reaction was stirred for 16 h at RT then EDC (0.5 g, 2.6 mmol, 1.5 eq.) was added. The resulting mixture was heated to 80° C. for 1 h. The solvent was evaporated and the residue was diluted with $CH_2Cl_2$ (25 mL). The solution was washed with $H_2O$ (25 mL), $NaHCO_3$ (25 mL, aq.) and brine (25 mL). The aqueous layers were back extracted with $CH_2Cl_2$ and the combined organic layers were dried over $MgSO_4$, filtered and concentrated. The crude was further purified by column chromatography (0-7.5% MeOH/$CH_2Cl_2$) to give pure [4-chloro-3-(4-methyl-piperazin-1-ylmethyl)-phenyl]-[5-(2-methylsulfanyl-pyrimidin-4-yloxy)-1H-benzimidazol-2-yl]-amine. MS m/z=496.2 (M+H)$^+$; MW Calc'd for $C_{24}H_{26}N_7OS$: 495.16.

EXAMPLE 19

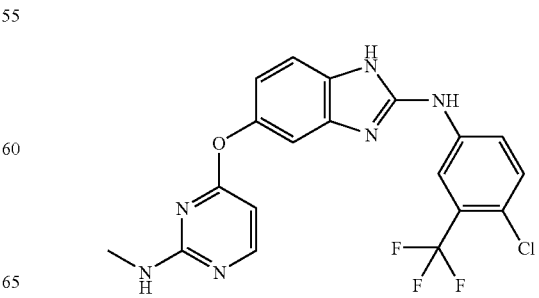

93

(4-Chloro-3-trifluoromethyl-phenyl)-[5-(2-methy-lamino-pyrimidin-4-yloxy)-1H-benzimidazol-2-yl]-amine Step A: (4-Chloro-3-trifluoromethyl-phenyl)-[5-(2-methyl-sulfanyl-pyrimidin-4-yloxy)-1H-benzimidazol-2-yl]-amine.

To a solution of 4-(2-methylsulfanyl-pyrimidin-4-yloxy)-benzene-1,2-diamine (Example 18, Step B, 400 mg, 1.6 mmol, 1.0 eq.) in anhydrous $CH_3CN$ (20 mL) was added drop wise a solution of 1-chloro-4-isothiocyanato-2-trifluorom-ethylbenzene (380 mg, 1.6 mmol, 1.0 eq.) in anhydrous $CH_3CN$ (10 mL). The solution was stirred for 16 h at RT. EDC (470 mg, 2.4 mmol, 1.5 eq.) was added and the reaction was heated to 80° C. and stirred for 2 h. The solvent was removed under reduced pressure. The residue was dissolved in $CH_2Cl_2$, and the solution was washed with $H_2O$ (25 mL), $NaHCO_3$ (aq., 25 mL) and brine (25 mL). The aqueous layers were back extracted with $CH_2Cl_2$ and the combined organic layers were dried over $MgSO_4$, filtered and concentrated. The crude was further purified by column chromatography (0-100% EtOAc/hexanes) to yield (4-chloro-3-trifluorom-ethyl-phenyl)-[5-(2-methylsulfanyl-pyrimidin-4-yloxy)-1H-benzimidazol-2-yl]-amine. MS m/z=452.1 $(M+H)^+$; MW Calc'd for $C_{19}H_{13}ClF_3N_5OS$: 451.86.

Step B: (4-Chloro-3-trifluoromethylphenyl)-[5-(2-methyl-sulfonylpyrimidin-4-yloxy)-1H-benzimidazol-2-yl]-amine.

To a solution of (4-chloro-3-trifluoromethyl-phenyl)-[5-(2-methylsulfanyl-pyrimidin-4-yloxy)-1H-benzimidazol-2-yl]-amine (Step A, 280 mg, 0.6 mmol, 1.0 eq.) in MeOH (10 mL) was added dropwise an aqueous solution (10 mL) of Oxone® (1.14 g, 1.8 mmol, 3.0 eq.), and a white solid formed. The reaction was stirred for 4 h at RT. The MeOH was removed under reduced pressure, the residue was diluted with 10% aq. $NaHCO_3$ and extracted with $CH_2Cl_2$. The organic layer was washed with 10% aq. $NaHCO_3$ and the organic layers were extracted with $CH_2Cl_2$. The combined organic layers were dried over $MgSO_4$, filtered and concentrated. The crude was further purified by column chromatography (0-100% EtOAc/hexanes) to yield (4-chloro-3-trifluorom-ethyl-phenyl)-[5-(2-methylsulfonylpyrimidin-4-yloxy)-1H-benzimidazol-2-yl]-amine. MS m/z=484.0 $(M+H)^+$; MW Calc'd for $C_{19}H_{13}ClF_3N_5O_3S$: 483.86.

Step C: (4-Chloro-3-trifluoromethyl-phenyl)-[5-(2-methy-lamino-pyrimidin-4-yloxy)-1H-benzimidazol-2-yl]-amine.

To a solution of (4-chloro-3-trifluoromethyl-phenyl)-[5-(2-methanesulfonyl-pyrimidin-4-yloxy)-1H-benzimidazol-2-yl]-amine (Step B, 120 mg, 0.2 mmol, 1.0 eq.) in anhydrous THF (4 mL) was added 1 mL of 2 M $CH_3NH_2$ in THF (2 mmol, 10 eq). The solution was heated to 80° C. for 1 h. The THF was removed under reduced pressure and the crude was purified by column chromatography (0-10% MeOH/$CH_2Cl_2$ with 1% $NH_4OH$) to yield pure (4-chloro-3-trifluoromethyl-phenyl)-[5-(2-methylamino-pyrimidin-4-yloxy)-1H-benz-imidazol-2-yl]-amine. MS m/z=435.1 $(M+H)^+$; MW Calc'd for $C_{19}H_{14}ClF_3N_6O$: 434.09.

94

EXAMPLE 20

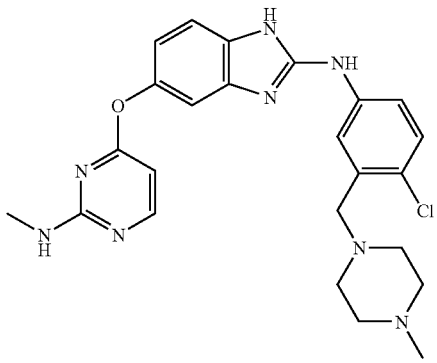

[4-chloro-3-(4-methyl-piperazin-1-ylmethyl)-phe-nyl]-[5-(2-methylamino-pyrimidin-4-yloxy)-1H-benzimidazol-2-yl]-amine Step A: 4-(3,4-Dinitro-phenoxy)-2-methylsulfonyl-pyrimi-dine.

To a cooled solution (0° C.) of 4-(3,4-dinitro-phenoxy)-2-methylsulfanyl-pyrimidine [Example 5, Step A] (2.0 g, 6.5 mmol, 1.0 eq) in $CH_2Cl_2$ (100 mL) was added m-CPBA (2.8 g, 16.2 mmol, 2.5 eq) in one portion. The solution was warmed to RT and stirred for 16 h at RT. The reaction mixture was washed with sat. $NaHCO_3$ (aq, 100 mL). The organic layer was dried over $MgSO_4$, filtered and concentrated to yield 4-(3,4-dinitro-phenoxy)-2-methylsulfonyl-pyrimidine.

Step B: 4-(2-Methylsulfonyl-pyrimidin-4-yloxy)-benzene-1, 2-diamine.

4-(3,4-Dinitro-phenoxy)-2-methylsulfonyl-pyrimidine (Step A, 1.0 g, 2.9 mmol, 1.0 eq.) was dissolved in MeOH (50 mL) and the atmosphere was replaced by argon. A catalytic amount of 10% Pd/C was added and the argon was replaced by a $H_2$ atmosphere. The mixture was stirred for 16 h at RT at atmospheric pressure. More Pd/C was added after the atm was replaced by argon, then the reaction was stirred under $H_2$ at RT for 48 h. The Pd/C was filtered off and the crude aniline was purified using column chromatography (0-100% EtOAc in hexanes) to give 4-(2-methanesulfonyl-pyrimidin-4-yloxy)-benzene-1,2-diamine.

Step C: 4-(2-Methylamino-pyrimidin-4-yloxy)-benzene-1,2-diamine.

To a solution of 4-(2-methanesulfonyl-pyrimidin-4-yloxy)-benzene-1,2-diamine (Step B, 400 mg, 1.4 mmol, 1.0 eq) in anhydrous THF (4 mL) was added 1 mL of 2 M $CH_3NH_2$ in THF (2 mmol, 1.4 eq). The solution was heated to 80° C. for 1 h. The THF was removed under reduced pressure. The crude was purified by column chromatography (0-10% MeOH/$CH_2Cl_2$ with 1% $NH_4OH$) to yield 4-(2-methy-lamino-pyrimidin-4-yloxy)-benzene-1,2-diamine.

Step D: [4-Chloro-3-(4-methylpiperazin-1-ylmethyl)phe-nyl]-[5-(2-methylamino-pyrimidin-4-yloxy)-1H-benzimida-zol-2-yl]-amine To a solution of 4-(2-methylamino-pyrimidin-4-yloxy)-benzene-1,2-diamine (Step C, 300 mg, 1.3 mmol, 1.0 eq) in anhydrous $CH_3CN$ (20 mL) was added drop-wise a solution of 1-(2-chloro-5-isothiocyanato-benzyl)-4-methyl-pipera-zine (405 mg [residual imidazole present], 1.3 mmol, 1.0 eq)

in anhydrous CH₃CN (10 mL). The solution was stirred for 16 h at RT. EDC (250 mg, 1.3 mmol, 1.0 eq) was added and the reaction was heated to 80° C. and stirred for 2 h. The solvent was removed under reduced pressure and residue was dissolved in CH₂Cl₂/MeOH (50 mL). The organic solution was washed with H₂O (25 mL), NaHCO₃ (aq, 25 mL) and brine (25 mL). The aqueous layers were back extracted with CH₂Cl₂ and the combined organic layers were dried over MgSO₄, filtered and concentrated. The crude was further purified by column chromatography (0-10% MeOH/CH₂Cl₂ with 1% NH₄OH) followed by preparative TLC and finally reverse phase HPLC (5-100% H₂O/CH₃CN with 0.1% TFA) to yield [4-chloro-3-(4-methyl-piperazin-1-ylmethyl)-phenyl]-[5-(2-methylamino-pyrimidin-4-yloxy)-1H-benzimidazol-2-yl]-amine. MS m/z=479.2 (M+H)⁺; MW Calc'd for C₂₄H₂₇ClN₈O: 478.20.

EXAMPLE 21

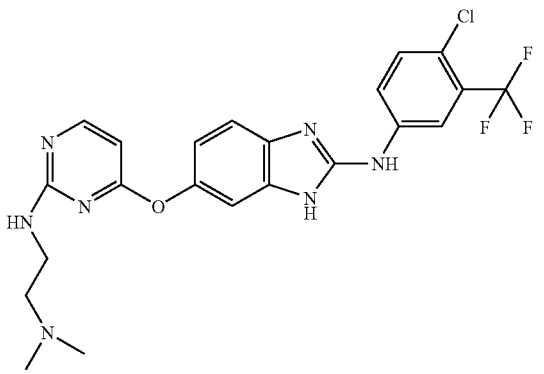

(4-Chloro-3-trifluoromethylphenyl)-[5-(2-(2-N,N-dimethyl-aminoethylamin)pyrimidin-4-yloxy)-1H-benzimidazol-2-yl]-amine The title compound was prepared similarly to the procedure outlined above in Example 19, Step C using the appropriate amine. MS (MH⁺)=492.4, MW: 491.14 Calc'd for: C₂₂H₂₁ClF₃N₇O.

EXAMPLE 22

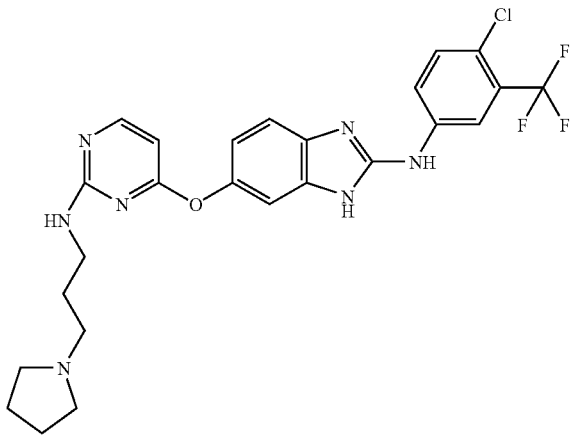

(4-Chloro-3-trifluoromethylphenyl)-{6-[2-(3-pyrrolidin-1-yl-propylamino)pyrimidin-4-yloxy]-1H-benzimidazol-2-yl}-amine The title compound was prepared similarly to the procedure outlined above in Example 19, Step C using the appropriate amine. MS (MH⁺)=532.4, MW: 531.18 Calc'd for: C₂₅H₂₅ClF₃N₇O.

EXAMPLE 23

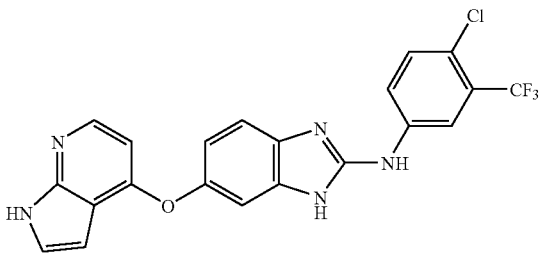

(4-Chloro-3-trifluoromethylphenyl)-[6-(1H-pyrrolo[2,3-b]pyridin-4-yloxy)-1H-benzimidazol-2-yl]-amine Step A: 1H-Pyrrolo[2,3-b]pyridine 7-oxide To a suspension of 1H-pyrrolo[2,3-b]pyridine (20.0 g) and NaHCO₃ (90 g) in 1:1 MeOH/H₂O (1000 mL) was added Oxone® (212 g) in portions during a 40 min period. The mixture was stirred at RT for 5 h. The solid was removed by filtration and the filtrate was concentrated to dryness. The solid residue was washed several times with CH₂Cl₂/MeOH 90/10 (500 mL). The combined organic solutions were concentrated under vacuum. The resulting crystalline solid was dissolved in CH₂Cl₂ (1 L). The organic solution was dried over MgSO₄ and the solvent was removed under vacuum. The crude material was purified on Silica gel using a CH₂Cl₂/EtOAc gradient (100/0 to 0/100) to afford 1H-pyrrolo[2,3-b]pyridine 7-oxide.

Step B: 4-Chloro-1H-pyrrolo[2,3-b]pyridine

To cooled POCl₃ (50 mL) in a dried round bottom flask, 1H-pyrrolo[2,3-b]pyridine 7-oxide (6.6 g, step A) was added in portions. The mixture was heated to reflux for 5 h. After cooling to RT, POCl₃ was evaporated under high vacuum with gentle heating (40-50° C.) to obtain a black residue. Water (50 mL) was added slowly and the pH was adjusted to 8-9 with Na₂CO₃ (first with solid, then saturated aqueous solution). The resulting precipitate was collected by filtration, washed with cold H₂O and dried in a vacuum oven (50° C.) to give 4-chloro-1H-pyrrolo[2,3-b]pyridine as a tan powder. This was a mixture of desired product and a regioisomer, which was used in the next step without further purification.

Step C: 4-(3,4-Dinitro-phenoxy)-1H-pyrrolo[2,3-b]pyridine.

A mixture of 4-chloro-1H-pyrrolo[2,3-b]pyridine (Step B, 1.0 g, 6.5 mmol) and 3,4-dinitrophenol (1.41 g, 7.6 mmol) was heated at 150° C. for 8 h. The resulting crude solid was dissolved in NaOH (12N) and CH₂Cl₂. The aqueous layer was extracted several times with CH₂Cl₂. The insoluble material was solubilized in acetone. The acetone solution was diluted with CH₂Cl₂ and washed with water. The combined CH₂Cl₂ layers were dried and concentrated under vacuum. The crude material was purified on silica gel using a CH₂Cl₂/EtOH gradient (100/0 to 90/10) to give 4-(3,4-dinitro-phenoxy)-1H-pyrrolo[2,3-b]pyridine.

Step D: 4-(1H-Pyrrolo[2,3-b]pyridin-4-yloxy)-benzene-1,2-diamine.

A solution of 4-(3,4-dinitro-phenoxy)-1H-pyrrolo[2,3-b]pyridine (Step C, 0.284 g, 0.95 mmol) in a 2/1 EtOH/EtOAc (30 mL) mixture with a catalytic amount of 10% Pd/C was stirred under $H_2$ at RT and atmospheric pressure. The catalyst was removed by filtration and the solvents were removed under vacuum. The crude material was purified on silica gel using a $CH_2Cl_2$/EtOH/$NH_4$OH gradient (100/0/0 to 90/10/1) to give 4-(1H-pyrrolo[2,3-b]pyridin-4-yloxy)-benzene-1,2-diamine.

Step E: (4-Chloro-3-trifluoromethyl-phenyl)-[6-(1H-pyrrolo[2,3-b]pyridin-4-yloxy)-1H-benzimidazol-2-yl]-amine.

The title compound was prepared by the method described in Example 1, using 4-(1H-pyrrolo[2,3-b]pyridin-4-yloxy)-benzene-1,2-diamine (Step D, 0.082 g, 0.34 mmol) and 1-chloro-4-isothiocyanato-2-trifluoromethyl-benzene (0.081 g, 0.34 mmol). MS (MH$^+$)=444.1, MW: 443.08 Calc'd for: $C_{21}H_{13}ClF_3N_5O$.

EXAMPLE 24

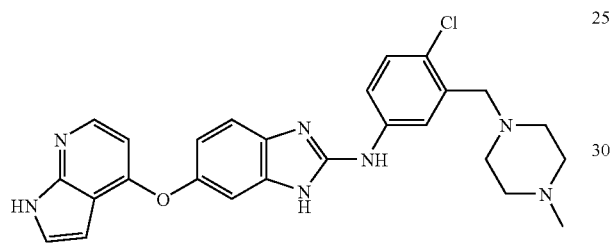

[4-Chloro-3-(4-methyl-piperazin-1-ylmethyl)-phenyl]-[6-(1H-pyrrolo[2,3-b]pyridin-4-yloxy)-1H-benzimidazol-2-yl]-amine The title compound was prepared similarly to the procedure outlined in Preparations III-IV and Example 23. MS (MH$^+$)=488.2, MW: 487.19 Calc'd for: $C_{26}H_{26}ClN_7O$.

EXAMPLE 25

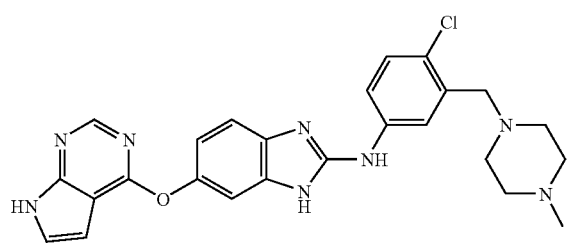

[4-Chloro-3-(4-methyl-piperazin-1-ylmethyl)-phenyl]-[6-(7H-pyrrolo[2,3-d]pyrimidin-4-yloxy)-1H-benzimidazol-2-yl]-amine Step A: 4-(3,4-Dinitro-phenoxy)-7,7a-dihydro-4aH-pyrrolo[2,3-d]pyrimidine.

4-Chloro-7,7a-dihydro-4aH-pyrrolo[2,3-d]pyrimidine (1.66 g, 10.8 mmol), 3,4-dinitrophenol (2.4 g, 13 mmol) and TFA/TEA were heated at 150° C. for 2 h. The resulting green solid was purified on silica gel using a Hexane/EtOAc gradient (100/0 to 50/50) to give 4-(3,4-dinitro-phenoxy)-7,7a-dihydro-4aH-pyrrolo[2,3-d]pyrimidine.

Step B: [4-Chloro-3-(4-methyl-piperazin-1-ylmethyl)-phenyl]-[6-(7H-pyrrolo[2,3-d]pyrimidin-4-yloxy)-1H-benzimidazol-2-yl]-amine.

The title compound was prepared similarly to the procedure outlined in Preparations III-IV and Example 23. MS (MH$^+$)=489.2 MW: 488.18; Calc'd for: $C_{25}H_{25}ClN_8O$.

EXAMPLE 26

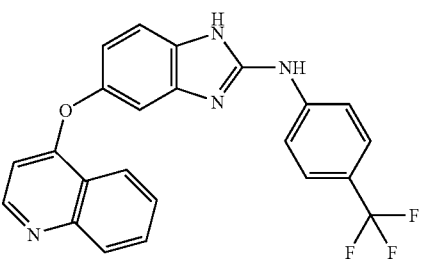

[5-(Quinolin-4-yloxy)-1H-benzimidazol-2-yl]-(4-trifluoromethyl-phenyl)-amine

Step A: 4-(3,4-Dinitro-phenoxy)-quinoline.

4-Chloroquinoline (4.3 g, 26.3 mmol) and 3,4-dinitrophenol (41.5 g, 24.4 mmol) were heated at 150° C. for 30 min. The mixture was cooled to RT and the residue was dissolved in $CH_2Cl_2$. The mixture was diluted in NaOH 2 M and extracted with $CH_2Cl_2$. The organic phase was dried, filtered and evaporated. The residue was diluted in EtOAc and filtered through a silica pad. The solvent was removed to give the title compound as a brown solid.

Step B: 4-(Quinolin-4-yloxy)-benzene-1,2-diamine.

4-(3,4-Dinitro-phenoxy)-quinoline (Step A, 400 mg, 1.2 mmol) was dissolved in THF at 0° C., and AcOH (1.5 mL) was added followed by zinc dust (2.5 g, 38 mmol). The mixture was stirred at RT for 1 h then filtered on a silica pad. The solvent was evaporated; the residue was dissolved in $CH_2Cl_2$ and washed with 1M NaOH. The organic phases were dried, filtered and evaporated to give the title compound, as a brown-orange oil.

Step C: [5-(Quinolin-4-yloxy)-1H-benzimidazol-2-yl]-(4-trifluoromethyl-phenyl)-amine.

To a solution of 4-(quinolin-4-yloxy)-benzene-1,2-diamine (Step B, 227 mg) in $CH_3CN$ (60 mL) was added over 5 min, a solution of 1-isothiocyanato-4-trifluoromethyl-benzene (183 mg) in $CH_3CN$ 10 mL). The mixture was stirred for 12 h at RT and EDC (260 mg) was added, followed by $CH_3CN$ (30 mL). The resulting mixture was heated at 80° C. for 2 h, then cooled to RT. The solvent was evaporated and the residue was dissolved in EtOAc and washed with water. The organic phase was dried, filtered and evaporated. The residue was purified by flash chromatography in EtOAc to give an orange-brown solid. MS (MH$^+$)=420.9, MW: 420.18 Calc'd for: $C_{23}H_{15}F_3N_4O$.

EXAMPLE 27

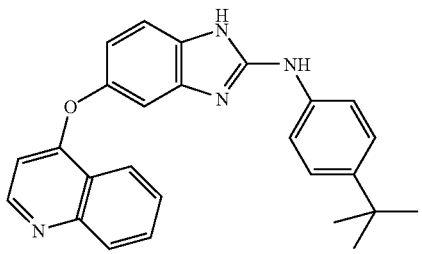

(4-tert-Butyl-phenyl)-[5-(quinolin-4-yloxy)-1H-benzimidazol-2-yl]-amine

The title compound was prepared according the procedure similar to that described in Preparation III and Example 26. MS (MH$^+$)=409.2, Mass 408.20 Calc'd for $C_{26}H_{24}N_4O$.

EXAMPLE 28

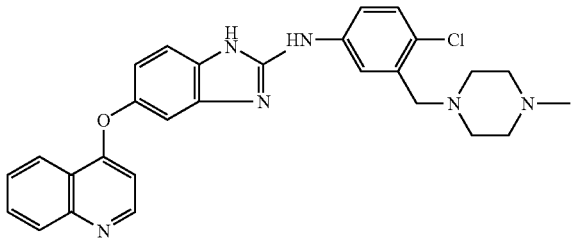

[4-Chloro-3-(4-methyl-piperazin-1-ylmethyl)-phenyl]-[5-(quinolin-4-yloxy)-1H-benzimidazol-2-yl]-amine The title compound was prepared according the procedure similar to that described for Preparation III and Example 26. MS (MH$^+$)=499.2, 498.19 Calc'd for $C_{28}H_{27}ClN_6O$.

EXAMPLE 29

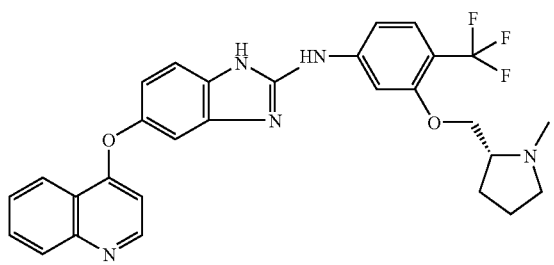

[3-(1-Methyl-pyrrolidin-2-ylmethoxy)-4-trifluoromethyl-phenyl]-[5-(quinolin-4-yloxy)-1H-benzimidazol-2-yl]-amine The title compound was prepared according the procedure similar to that described for Preparations III and XV, and Example 26. MS (MH$^+$)=534.3, 533.2; Calc'd for: $C_{29}H_{26}F_3N_5O_2$.

EXAMPLE 30

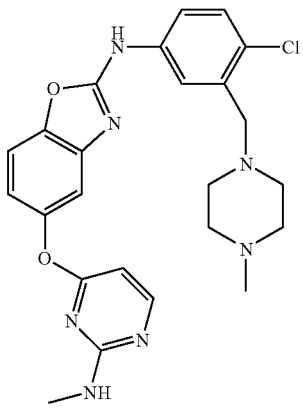

[4-Chloro-3-(4-methyl-piperazin-1-ylmethyl)-phenyl]-[5-(2-methylamino-pyridin-4-yloxy)-benzoxazol-2-yl]-amine Step A: 4-(4-Benzyloxy-phenoxy)-2-chloro-pyrimidine.

To a stirred RT slurry of NaH (0.5 g of 60% oil dispersion, 12.6 mmol) in 15 mL DMF was added 4-benzyloxyphenol (2.40 g, 12.0 mmol). The mixture was stirred for 10 min before 2,4-dichloropyrimidine (1.79 g, 12.0 mmol) was added. A mild exotherm occurred. The reaction was stirred for 2 h and quenched with saturated aqueous NaHCO$_3$. The reaction was diluted with EtOAc, the layers were separated, and the organic layer was washed twice with 2 N NaOH, once with brine, then dried over Na$_2$SO$_4$. The organic layer was filtered and concentrated in vacuo to yield crude title compound contaminated with minor impurities by H-NMR. MS (MH$^+$)=NA; Calc'd 312.76 for $C_{17}H_{13}ClN_2O_2$.

Step B: [4-(4-Benzyloxy-phenoxy)-pyrimidin-2-yl]-methyl-amine.

4-(4-Benzyloxy-phenoxy)-2-chloro-pyrimidine (Step A, 2.03 g, 6.49 mmol) was dissolved in 10 mL DMSO in a sealed tube at 0° C. 2 N CH$_3$NH$_2$ (in THF) was added (4.9 mL, 9.7 mmol), and the tube was sealed, warmed first to RT for 2 h, then to 70° C. for 2 h with stirring. The reaction was cooled to RT and concentrated in vacuo to a DMSO solution. The crude solution was diluted into Et$_2$O and 1 N NaOH (aq) was added. The layers were separated, and the organic layer was washed several times with water then brine. The organic layer was dried over Na$_2$SO$_4$, filtered, and concentrated in vacuo. The crude material was purified by silica gel column chromatography using a hexanes/EtOAc gradient to yield the title compound as a white solid. MS (MH$^+$)=308.3; Calc'd 307.36 for $C_{18}H_{17}N_3O_2$.

Step C: 4-(2-Methylamino-pyrimidin-4-yloxy)-phenol.

[4-(4-Benzyloxy-phenoxy)-pyrimidin-2-yl]-methyl-amine (Step B, 0.75 g, 2.44 mmol) was dissolved in 5 mL MeOH and 10 mL EtOAc. To the argon-degassed solution was added 10% by weight Pd/C (0.15 g). The reaction was stirred vigorously at RT under 1 atm H$_2$ gas for 4 days. The reaction was filtered through Celite® and concentrated in vacuo to yield the title compound. MS (MH$^+$)=218.1; Calc'd 217.23 for $C_{11}H_{11}N_3O_2$.

Step D: 4-(2-Methylamino-pyrimidin-4-yloxy)-2-nitro-phenol.

4-(2-Methylamino-pyrimidin-4-yloxy)-phenol (Step C, 0.20 g, 0.92 mmol) was dissolved in 5 mL AcOH at RT. Fuming HNO$_3$ (0.064 g, 0.92 mmol) was diluted with about 0.012 mL water, then added dropwise over 1 min to the reaction. The reaction was stirred for 18 h, after which it was added slowly to 40 mL saturated aqueous NaHCO$_3$ and extracted with CH$_2$Cl$_2$. The organic layer was washed with NaHCO$_3$ and brine, dried over Na$_2$SO$_4$, filtered, and concentrated in vacuo. The crude residue was purified by silica gel column chromatography using hexanes/EtOAc gradient to yield the title compound. MS (MH$^+$)=263.1; Calc'd 262.23 for $C_{11}H_{10}N_4O_4$.

Step E: 2-Amino-4-(2-methylamino-pyrimidin-4-yloxy)-phenol.

4-(2-Methylamino-pyrimidin-4-yloxy)-2-nitro-phenol (Step D, 0.163 g, 0.620 mmol) was dissolved in 7 mL MeOH and 15 mL EtOAc. To the argon-degassed solution was added 10% by weight Pd/C (0.08 g). The reaction was stirred vigorously at RT under 1 atm H$_2$ gas for 18 h. The reaction was filtered through a Celite® plug and concentrated to dryness to yield the title compound. MS (MH$^+$)=233.1; MW Calc'd 232.24 for $C_{11}H_{12}N_4O_2$.

Step F: [4-Chloro-3-(4-methyl-piperazin-1-ylmethyl)-phenyl]-[5-(2-methylamino-pyridin-4-yloxy)-benzoxazol-2-yl]-amine.

To a solution of 2-amino-4-(2-methylamino-pyrimidin-4-yloxy)-phenol (Step E, 0.143 g, 0.616 mmol) in 30 mL CH$_3$CN was added dropwise over 5 min a solution 1-(2-chloro-5-isothiocyanato-benzyl)-4-methyl-piperazine (0.174 g, 0.616 mmol) in 10 mL CH$_3$CN. The reaction was stirred 18 h at RT. The reaction was diluted with 10 mL CH$_3$CN, then EDC (0.118 g, 0.616 mmol) was added. The reaction was heated at 80° C. for 3 h. The reaction was cooled to RT then concentrated in vacuo. The crude mix was dissolved in EtOAc and H$_2$O. The layers were separated, and the organic layer was washed with brine, dried over Na$_2$SO$_4$, filtered, and concentrated in vacuo. The residue was purified by a combination of silica gel column chromatography and silica gel prep plates to obtain the title compound. MS (MH$^+$)= 480.2; MW Calc'd 479.97 for $C_{24}H_{26}ClN_7O_2$.

EXAMPLE 31

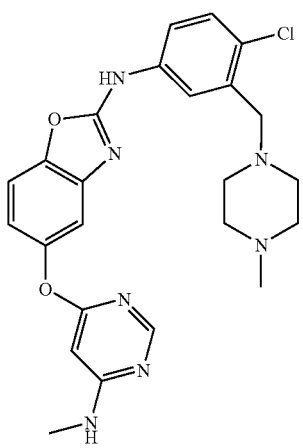

[4-Chloro-3-(4-methyl-piperazin-1-ylmethyl)-phenyl]-[5-(6-methylamino-pyrimidin-4-yloxy)-benzoxazol-2-yl]-amine The title compound was prepared similarly to the procedure outlined above in Example 30 starting from 4,6-dichloro-pyrimidine. MS (MH$^+$)=480.5; MW Calc'd 479.97 for $C_{24}H_{26}ClN_7O_2$.

EXAMPLE 32

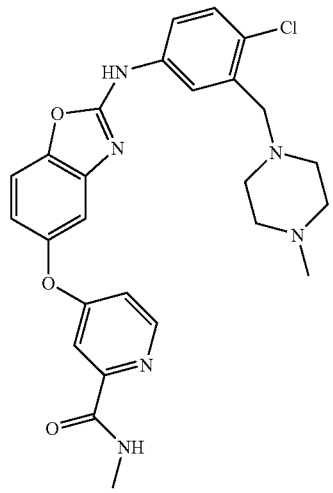

4-{2-[4-Chloro-3-(4-methyl-piperazin-1-ylmethyl)-phenylamino]-benzoxazol-5-yloxy}-pyridine-2-carboxylic acid methylamide Step A: 4-(4-Benzyloxy-phenoxy)-pyridine-2-carboxylic acid methylamide To a stirred RT slurry of NaH (2.24 g of 60% oil dispersion, 55.9 mmol) in 40 mL DMF was added 4-benzyloxyphenol (11.2 g, 55.9 mmol). The mixture was stirred for 10 min before adding 4-chloro-pyridine-2-carboxylic acid methylamide (Example 2 Step A, 3.18 g, 18.6 mmol). The reaction was stirred at RT for 5 min, then at 75° C. for 2 h, and finally at 85° C. for 6 h. The reaction was cooled to RT, quenched with saturated aqueous NaHCO$_3$, then diluted with Et$_2$O and 6 N NaOH. The layers were separated, and the organic layer was washed twice with 6 N NaOH, once with brine, dried over Na$_2$SO$_4$, filtered, and concentrated in vacuo, to yield the title compound as a light salmon-colored solid. MS (MH$^+$)= 335.1; MW Calc'd 334.38 for $C_{20}H_{18}N_2O_3$.

Step B: 4-{2-[4-Chloro-3-(4-methyl-piperazin-1-ylmethyl)-phenylamino]-benzoxazol-5-yloxy}-pyridine-2-carboxylic acid methylamide.

The title compound was prepared similarly to the procedure outlined above in Example 30, steps C to F. MS (MH$^+$)=507.4; MW Calc'd 506.99 for $C_{26}H_{27}ClN_6O_3$.

EXAMPLE 33-39

The following compounds were prepared similarly to the procedure outlined above in Example 32 using the corresponding isothiocyanates.

TABLE 4
| Ex. | Structure | Mol. Formula | Mol. Weight | MS (MH+) |
|---|---|---|---|---|
| 33 | 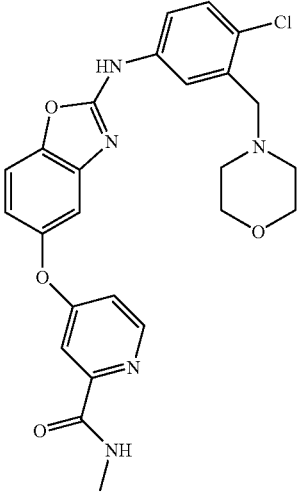 4-[2-(4-Chloro-3-morpholin-4-ylmethyl-phenyl-amino)-benzoxazol-5-yloxy]-pyridine-2-carboxylic acid methylamide | $C_{25}H_{24}ClN_5O_4$ | 493.95 | 494.3 |
| 34 | 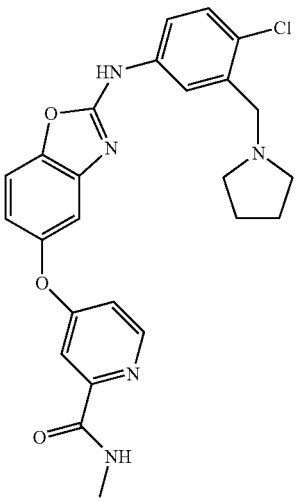 4-[2-(4-Chloro-3-pyrrolidin-1-ylmethyl-phenylamino)-benzoxazol-5-yloxy]-pyridine-2-carboxylic acid methylamide | $C_{25}H_{24}ClN_5O_3$ | 477.95 | 478.1 |

TABLE 4-continued

| Ex. | Structure | Mol. Formula | Mol. Weight | MS (MH+) |
|---|---|---|---|---|
| 35 | 4-[2-(Isoquinolin-3-ylamino)-benzoxazol-5-yloxy]-pyridine-2-carboxylic acid methylamide | C₂₃H₁₇N₅O₃ | 411.42 | 412.1 |
| 36 | 4-{2-[4-Chloro-3-(1-methyl-pyrrolidin-2-ylmethoxy)-phenylamino]-benzoxazol-5-yloxy}-pyridine-2-carboxylic acid methylamide | C₂₆H₂₆ClN₅O₄ | 507.98 | 508.2 |
| 37 | 4-((2-((4-Chlorophenyl)-amino)-1,3-benzoxazol-5-yl)oxy)-N-methyl-2-pyridinecarboxamide | C₂₀H₁₅ClN₄O₃ | 394.82 | 395.1 |

TABLE 4-continued

| Ex. | Structure | Mol. Formula | Mol. Weight | MS (MH+) |
|---|---|---|---|---|
| 38 | 4-((2-((4-Bromophenyl)amino)-1,3-benzoxazol-5-yl)oxy)-N-methyl-2-pyridinecarboxamide | C$_{20}$H$_{15}$BrN$_4$O$_3$ | 439.27 | 441.0 |
| 39 | N-Methyl-4-((2-((4-(1-methylethyl)phenyl)amino)-1,3-benzoxazol-5-yl)oxy)-2-pyridinecarboxamide | C$_{23}$H$_{22}$N$_4$O$_3$ | 402.46 | 403.2 |

EXAMPLE 40

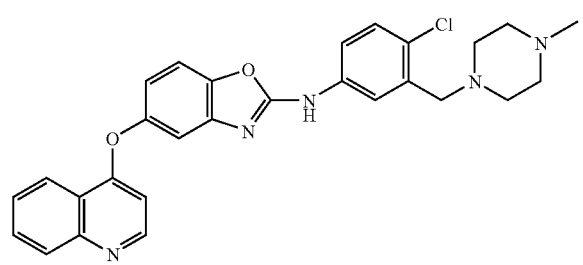

([4-Chloro-3-(4-methyl-piperazin-1-ylmethyl)-phenyl]-[5-(quinolin-4-yloxy)-benzoxazol-2-yl]-amine)

Step A: 2-Nitro-4-(quinolin-4-yloxy)-phenol.

The title compound was prepared similarly to the procedure outlined above in Example 30, Steps A, C and D starting with 4-chloroquinoline.

Step B: 2-Amino-4-(quinolin-4-yloxy)-phenol.

2-Nitro-4-(quinolin-4-yloxy)-phenol (Step A, 200 mg) was dissolved in THF (50 mL) at 0° C. and AcOH (0.88 mL) was added followed by zinc dust (2.3 g). The mixture was stirred at RT for 1.5 h and filtered through a Celite® pad. The solvent was evaporated, the residue was dissolved in CH$_2$Cl$_2$ and washed with 1M NaOH. The organic phases were dried, filtered and evaporated to give the title compound as a brown solid.

Step C: ([4-Chloro-3-(4-methyl-piperazin-1-ylmethyl)-phenyl]-[5-(quinolin-4-yloxy)-benzoxazol-2-yl]-amine)

The title compound was prepared similarly to the procedure outlined above in Example 30, Step F. MS (MH+)= 500.2; MW Calc'd 500.00 for C$_{28}$H$_{26}$ClN$_5$O$_2$.

EXAMPLE 41

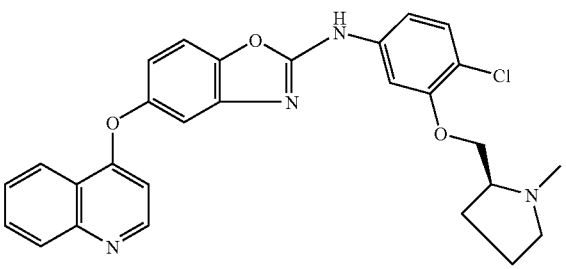

[4-Chloro-3-(1-methyl-pyrrolidin-2-ylmethoxy)-phenyl]-[5-(quinolin-4-yloxy)-benzoxazol-2-yl]-amine The title compound was prepared according the procedure similar to that described for Example 40. MS (MH+)=501.2; MW Calc'd 500.99 for $C_{28}H_{25}ClN_4O_3$.

EXAMPLE 42

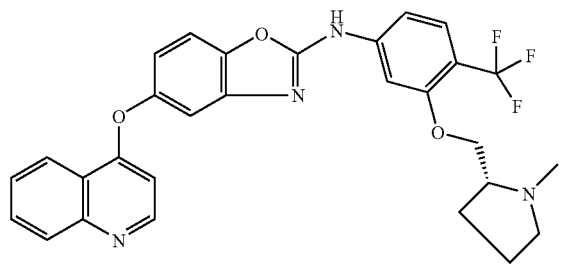

[3-(1-Methyl-pyrrolidin-2-ylmethoxy)-4-trifluoromethyl-phenyl]-[5-(quinolin-4-yloxy)-benzoxazol-2-yl]-amine The title compound was prepared according the procedure similar to that described for Example 40. MS (MH+)=535.2; MW Calc'd 534.54 for $C_{29}H_{25}F_3N_4O_3$.

EXAMPLE 43

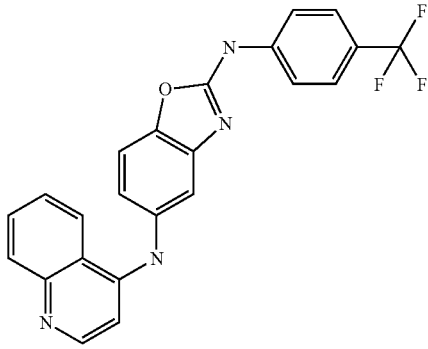

$N^5$-(4-Quinolinyl)-$N^2$-(4-(trifluoromethyl)phenyl)-1,3-benzoxazole-2,5-diamine Step A: 2-Nitro-4-(quinolin-4-ylamino)-phenol TFA (0.57 mL) was added to a suspension of 4-chloro-quinoline (0.48 mg, 2.9 mmol) and 4-amino-2-nitrophenol (0.45 g, 2.9 mmol) in i-PrOH (4 mL) was added at RT. The reaction was heated to 130° C. in a sealed tube for 2 h. A solid precipitated upon cooling. The solid was filtered out and washed with i-PrOH to give 2-nitro-4-(quinolin-4-ylamino)-phenol.

Step B: $N^5$-(4-Quinolinyl)-$N^2$-(4-(trifluoromethyl)phenyl)-1,3-benzoxazole-2,5-diamine.

The title compound was prepared according the procedure similar to that described for Example 30, Steps E and F using the appropriate isothiocyanate. (MH+)=421.1; MW Calc'd 420.4; for $C_{23}H_{15}F_3N_4O$.

EXAMPLE 44

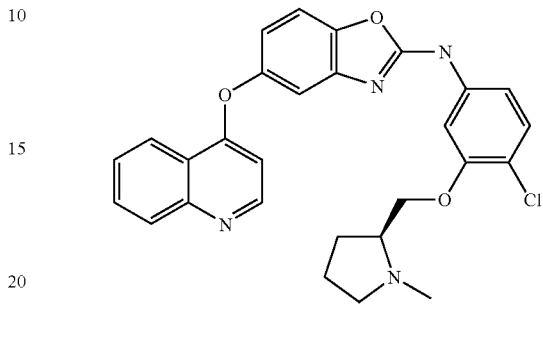

$N^2$-(4-Chloro-3-(((2S)-1-methyl-2-pyrrolidinyl)methoxy)phenyl)-$N^5$-(4-quinolinyl)-1,3-benzoxazole-2,5-diamine The title compound was prepared according the procedure similar to that described for Example 43 using the appropriate isothiocyanate. (MH+)=500.2; MW Calc'd 500.0; for $C_{28}H_{26}ClN_5O_2$.

EXAMPLE 45

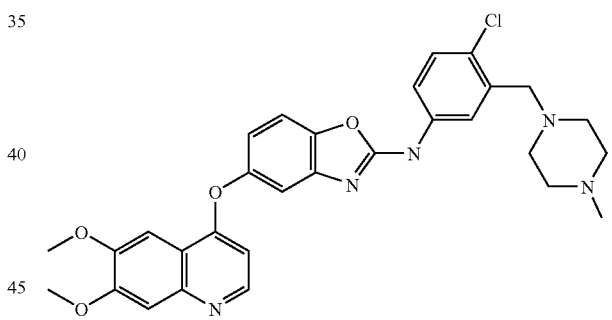

5-((6,7-bis(Methoxy)-4-quinolinyl)oxy)-N-(4-chloro-3-((4-methyl-1-piperazinyl)methyl)phenyl)-1,3-benzoxazol-2-amine Step A: 6,7-Dimethoxy-4-hydroxyquinoline To a stirred solution of 3,4-dimethoxy-5-anilinoacetophenone (6 g, 30.7 mmol) in dioxane (90 mL) was added solid NaOt-Bu (7 g, 73 mmol). The mixture was stirred for 30 min and ethylformate (16 mL) was added. The resulting mixture was stirred at RT for 2 h and water (5 mL) was added to the slurry. Stirring was continued for 10 min then the mixture was neutralized with aqueous HCl 1 N and the solid was filtered, washed with $H_2O$, rinsed with ether then dried under vacuum. A green-beige solid was obtained.

Step B: 4-Chloro-6,7-dimethoxyquinoline 6,7-Dimethoxy-4-hydroxyquinoline (Step A, 7.8 g) was dissolved in $POCl_3$ (45 mL) and heated at 85° C. for 3 h. The mixture was cooled down to RT, $POCl_3$ was evaporated and the resulting oil was quenched by adding ice at 0° C. The aqueous phase was basified to pH 8 and a solid precipitated. The solid was filtered and dried under vacuum to give 4-chloro-6,7-dimethoxyquinoline.

Step C: 5-((6,7-bis(Methoxy)-4-quinolinyl)oxy)-N-(4-chloro-3-((4-methyl-1-piperazinyl)methyl)phenyl)-1,3-benzoxazol-2-amine The title compound was prepared according the procedure similar to that described for Example 37 using 4-chloro-6,7-dimethoxyquinoline (Step C). (MH$^+$)=560.2; MW Calc'd 560.05; for C$_{30}$H$_{30}$ClN$_5$O$_4$.

EXAMPLE 46

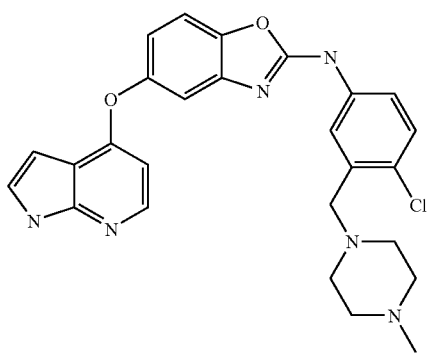

N-(4-Chloro-3-((4-methyl-1-piperazinyl)methyl) phenyl)-5-(1H-pyrrolo[2,3-b]pyridin-4-yloxy)-1,3-benzoxazol-2-amine Step A: 4-(4-Benzyloxy-phenoxy)-1H-pyrrolo[2,3-b]pyridine A mixture of 4-chloro-1H-pyrrolo[2,3-b]pyridine (1 g, 6.5 mmol), 4-benzyloxyphenol (1.5 g, 7.5 mmol) and Et$_3$N:TFA (1.2 mL) was heated to 150° C. for 96 h. Formation of the compound was monitored by HPLC-mass spec. The crude was directly purified on silica gel without work-up using a Hexanes/EtOAc gradient (100/0 to 0/100) to afford 4-(4-benzyloxy-phenoxy)-1H-pyrrolo[2,3-b]pyridine.

Step B: N-(4-Chloro-3-((4-methyl-1-piperazinyl)methyl) phenyl)-5-(1H-pyrrolo[2,3-b]pyridin-4-yloxy)-1,3-benzoxazol-2-amine.

The title compound was prepared according the procedure similar to that described for Example 30, Steps C to F using the appropriate isothiocyanate. (MH$^+$)=488.98; Mass Calc'd 488.2; for C$_{26}$H$_{25}$ClN$_6$O$_2$.

EXAMPLE 47

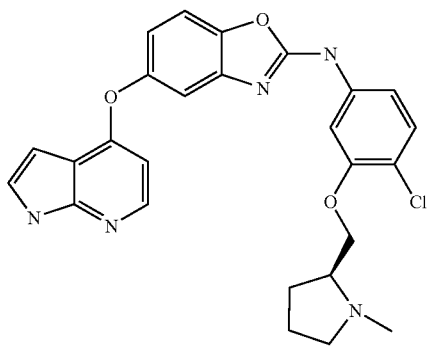

N-(4-Chloro-3-(((2S)-1-methyl-2-pyrrolidinyl)methoxy)phenyl)-5-(1H-pyrrolo[2,3-b]pyridin-4-yloxy)-1,3-benzoxazol-2-amine The title compound was prepared according the procedure similar to that described for Example 46 using the appropriate isothiocyanate. (MH$^+$)=489.97; MW Calc'd 490.2 for C$_{26}$H$_{24}$ClN$_5$O$_3$.

EXAMPLE 48

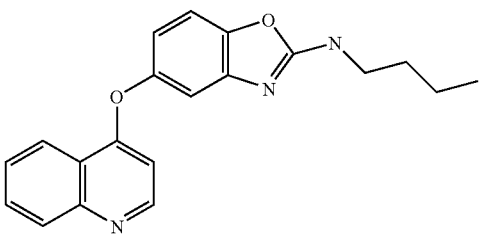

N-Butyl-5-(4-quinolinyloxy)-1,3-benzoxazol-2-amine

The title compound was prepared according the procedure similar to that described for Example 40 using the appropriate isothiocyanate. (MH$^+$)=334.2; MW Calc'd 333.39 for C$_{20}$H$_{19}$N$_3$O$_2$.

EXAMPLE 49

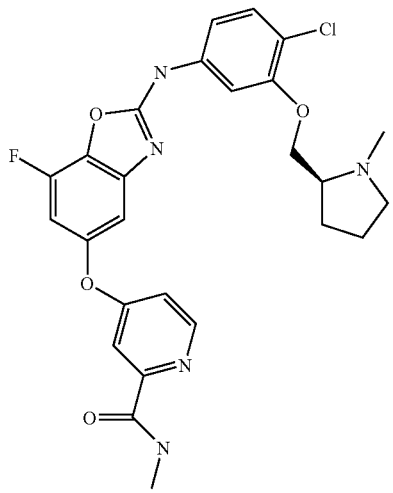

4-((2-((4-Chloro-3-(((2S)-1-methyl-2-pyrrolidinyl) methoxy)phenyl)amino)-7-fluoro-1,3-benzoxazol-5-yl)oxy)-N-methyl-2-pyridinecarboxamide The title compound was prepared according the procedure similar to that described for Example 32 using 4-benzyloxy-3-fluorophenol. (MH$^+$)=526.2; MW Calc'd 525.97 for C$_{26}$H$_{25}$ClFN$_5$O$_4$.

EXAMPLE 50

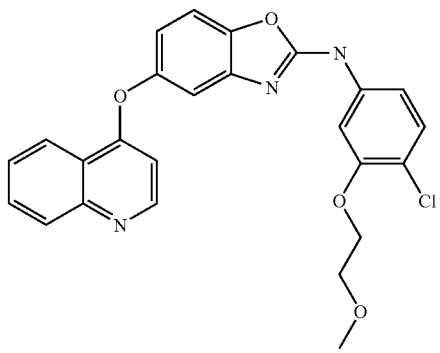

N-(4-Chloro-3-((2-(methoxy)ethyl)oxy)phenyl)-5-(4-quinolinyloxy)-1,3-benzoxazol-2-amine Step A: 1-Chloro-2-(2-methoxyethoxy)-4-nitrobenzene To a solution of 5-nitro-2-chlorophenol (1.0 g, 5.8 mmol) and 2-methyloxychloroethane (2.6 mL, 28.8 mmol) in DMF (20 mL) was added $K_2CO_3$ (2.4 g, 17.4 mmol). The suspension was stirred at 80° C. for 18 h. After cooling, the mixture was filtered, the salts washed with EtOAc and the solvents removed under vacuum. The residue was dissolved in EtOAc and washed twice with NaOH (1 N) and once with $H_2O$. The EtOAc layer was dried over $MgSO_4$ and concentrated under vacuum. The crude was purified on silica gel using a Hexanes/EtOAc gradient (100/0 to 50/50) to give 1-chloro-2-(2-methoxy-ethoxy)-4-nitro-benzene.

Step B: 4-Chloro-3-(2-methoxyethoxy)phenylamine

The title compound was prepared according the procedure similar to that described for Preparation V.

Step C: N-(4-Chloro-3-((2-(methoxy)ethyl)oxy)phenyl)-5-(4-quinolinyloxy)-1,3-benzoxazol-2-amine The title compound was prepared according the procedure similar to that described for Example 40 using the appropriate isothiocyanate. $(MH^+)=462.2$; MW Calc'd 461.91 for $C_{25}H_{20}ClN_3O_4$.

Other compounds included in this invention are set forth in Tables 5-8 below.

TABLE 5

| # | R | $R^1$ | X | $W^1$ |
|---|---|---|---|---|
| 51. | 2-chlorophenyl | 4-pyridyl | O | NH |
| 52. | 5-benzimidazolyl | 4-pyridyl | S | NH |
| 53. | 2-chlorophenyl | 4-pyridyl | O | NMe |
| 54. | 2-quinolinyl | 4-pyridyl | O | NMe |
| 55. | 2-benzthiazolyl | 4-pyridyl | S | NMe |
| 56. | 2-benzimidazolyl | 3-$CH_3NH(C=O)$-4-pyridyl | $CH_2$ | NMe |
| 57. | 5-benzimidazolyl | 3-$CH_3NH(C=O)$-4-pyridyl | O | NMe |
| 58. | 5-benzimidazolyl | 3-$CH_3NH(C=O)$-4-pyridyl | S | NMe |
| 59. | 4-chlorophenyl | 3-$CH_3NH(C=O)$-4-pyridyl | O | NH |
| 60. | 3,4-dichlorophenyl | 3-$CH_3NH(C=O)$-4-pyridyl | NH | NH |
| 61. | 4-fluorophenyl | 4-quinolyl | $CH_2$ | NH |
| 62. | 3-chlorophenyl | 4-quinolyl | S | NH |
| 63. | [structure] | 3-$CH_3(C=O)NH$-phenyl | O | NH |
| 64. | [structure] | 3-$H_2N(C=O)$phenyl | O | NH |
| 65. | 3-fluorophenyl | 4-quinolyl | NH | NH |
| 66. | 3-fluoro-4-methoxyphenyl | 4-quinolyl | O | NH |
| 67. | 3-fluoro-4-methylphenyl | 4-quinolyl | O | NH |
| 68. | 4-bromophenyl | 6,7-dimethoxy-4-quinolyl | NH | NH |
| 69. | 4-bromo-3-$CF_3$phenyl | 3-methyl-4-pyridyl | O | NH |
| 70. | 4-bromophenyl | 3-$CH_3(C=O)NH$-4-pyridyl | O | NH |

TABLE 5-continued

| # | R | R¹ | X | W¹ |
|---|---|---|---|---|
| 71. | 4-phenoxyphenyl | 3-CH₃NH(C=O)-phenyl | S | NH |
| 72. | 3-phenoxyphenyl | 3-CH₃NH(C=O)-phenyl | O | NH |
| 73. | 4-biphenyl | 2-MeNH-4-pyrimidinyl | O | NH |
| 74. | 4-cyclohexylphenyl | 2-MeNH-4-pyrimidinyl | NH | NH |
| 75. | 3-isoquinolyl | 2-MeNH-4-pyrimidinyl | O | NH |
| 76. | 3-quinolyl | 2-MeNH-4- | O | NH |
| 77. | 4-pyrimidinyl | 2-MeNH-4-pyrimidinyl | O | NH |
| 78. | 5-isoindolyl | 2-MeNH-4-pyrimidinyl | O | NH |
| 79. | [2-chloro-5-methylphenoxy-ethyl-pyrrolidinyl] | pyrimidinyl | | |
| 80. | [2-chloro-5-methylphenoxy-ethyl-pyrrolidinyl] | 4-pyridyl | O | NH |
| 81. | [2-chloro-5-methylphenoxy-ethyl-(3-dimethylamino)pyrrolidinyl] | 3-CH₃NH(C=O)-4-pyridyl | O | NH |
| 82. | [2-chloro-5-methylphenoxy-ethyl-(3-dimethylamino)pyrrolidinyl] | 4-pyridyl | O | NH |
| 83. | [2-chloro-5-methylphenoxy-ethyl-(3-(N-methyl-6,7-dimethoxyquinazolin-4-yl-amino))pyrrolidinyl] | | O | NH |
| 84. | [2-chloro-5-methylphenoxy-ethyl-(3-dimethylamino)pyrrolidinyl] | 3-CH₃NH(C=O)-4-pyridyl | O | NH |

TABLE 5-continued

| # | R | R¹ | X | W¹ |
|---|---|---|---|---|
| 85. | (2-Cl, 5-Me-phenyl)-O-CH₂CH₂-N(pyrrolidin-3-yl-NMe₂) | 2-MeNH-4-pyrimidinyl | O | NH |
| 86. | (2-Cl, 5-Me-phenyl)-CH₂-N(pyrrolidin-3-yl-NMe₂) | 4-pyridyl | O | NH |
| 87. | (2-Cl, 5-Me-phenyl)-CH₂-N(piperidin-4-yl-NMe₂) | 3-CH₃NH(C=O)-4-pyridyl | O | NH |
| 88. | (2-Cl, 5-Me-phenyl)-CH₂-N(piperidin-4-yl-NH₂) | 4-pyridyl | O | NH |
| 89. | (2-Cl, 5-Me-phenyl)-O-CH₂-(pyrrolidin-3-yl)-NH | 3-CH₃NH(C=O)-4-pyridyl | O | NH |
| 90. | (2-Cl, 5-Me-phenyl)-O-CH₂-(1-Me-pyrrolidin-3-yl) | 2-MeNH-4-pyrimidinyl | O | NH |
| 91. | (2-Cl, 5-Me-phenyl)-O-CH₂-(1-Me-piperidin-4-yl) | 2-MeNH-4-pyrimidinyl | O | NH |

TABLE 5-continued

| # | R | R¹ | X | W¹ |
|---|---|---|---|---|
| 92. | (2-Cl, 5-Me-phenyl)-O-CH₂-(piperidin-4-yl)-NH | 4-pyridyl | O | NH |
| 93. | (2-Cl, 5-Me-phenyl)-O-CH₂CH₂-OMe | 3-CH₃NH(C=O)-4-pyridyl | O | NH |
| 94. | (2-Cl, 5-Me-phenyl)-O-CH₂CH₂-O-EtOMe | 2-MeNH-4-pyrimidinyl | O | NH |
| 95. | 5-Cl, 2-Me-pyridyl | 2-MeNH-4-pyrimidinyl | O | NH |
| 96. | 5-CF₃, 2-Me-pyridyl | 4-pyridyl | O | NH |
| 97. | (2-Cl, 5-Me-phenyl)-O-CH₂-(1-methylpyrrolidin-2-yl) | 3-CH₃NH(C=O)-4-pyridyl | O | NH |
| 98. | (2-Cl, 5-Me-phenyl)-NH-CH₂-(1-methylpyrrolidin-2-yl) | 4-quinolyl | O | NH |
| 99. | (2-Cl, 5-Me-phenyl)-NH-CH₂-(pyrrolidin-2-yl) | 4-quinolyl | O | NH |

TABLE 5-continued
| # | R | R¹ | X | W¹ |
|---|---|----|---|-----|
| 100. | 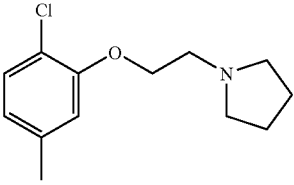 | 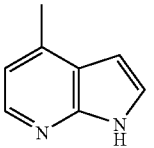 | O | NH |
| 101. | 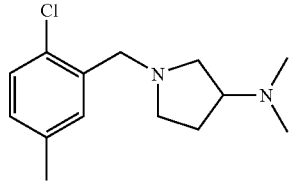 | 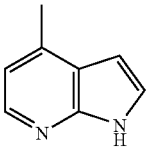 | O | NH |
| 102. | 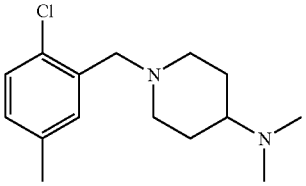 | 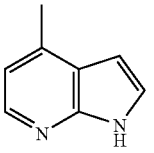 | O | NH |
| 103. | 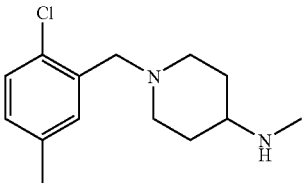 | 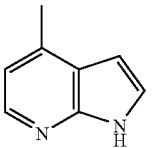 | O | NH |
| 104. | 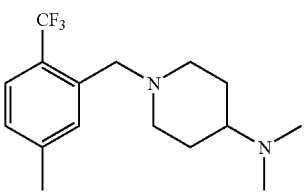 | 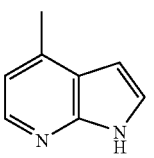 | O | NH |
| 105. | 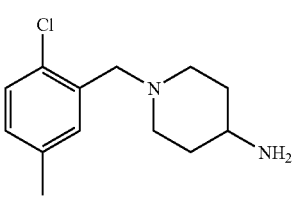 | 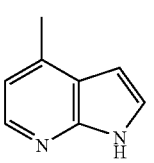 | O | NH |
| 106. | 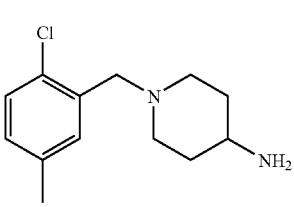 | 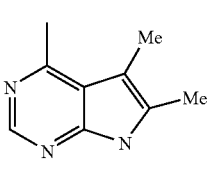 | O | NH |

TABLE 5-continued
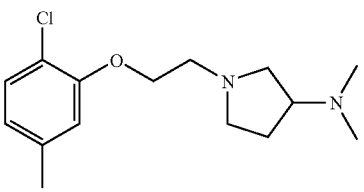
| # | R | R¹ | X | W¹ |
|---|---|----|---|----|
| 107. | 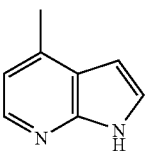 | 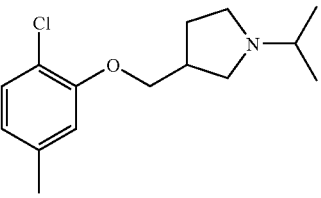 | O | NH |
| 108. | 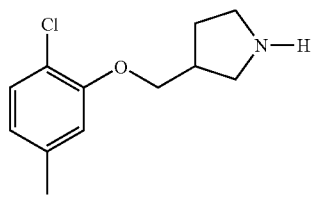 | 2-MeNH-4-pyrimidinyl | O | NH |
| 109. | 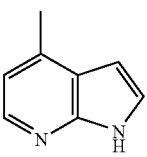 | 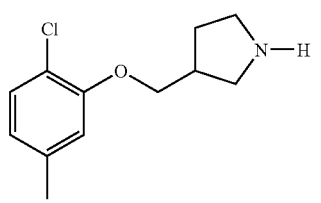 | O | NH |
| 110. | 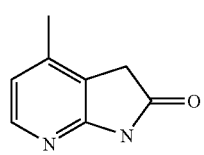 | 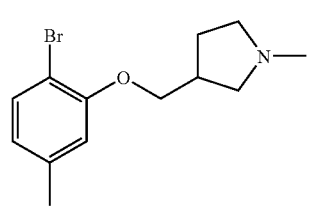 | O | NH |
| 111. | 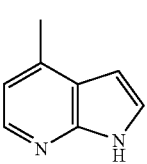 | 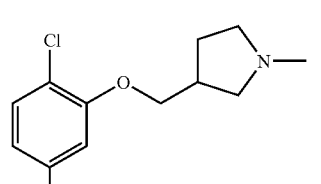 | O | NH |
| 112. | 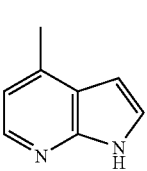 | 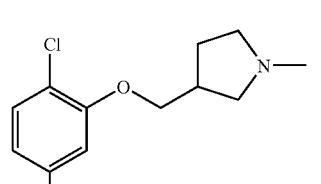 | O | NH |
| 113. | 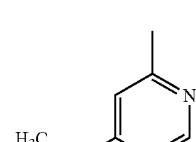 |  | O | NH |

TABLE 5-continued
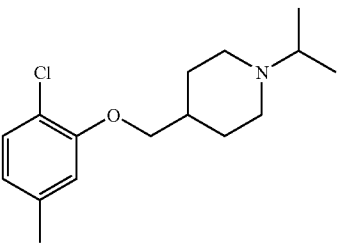
| # | R | R¹ | X | W¹ |
|---|---|----|---|-----|
| 114. | 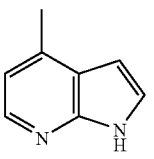 | 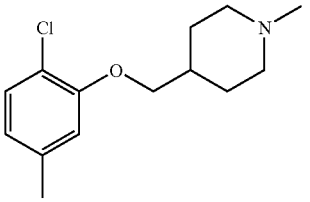 | O | NH |
| 115. | 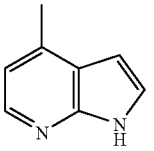 | 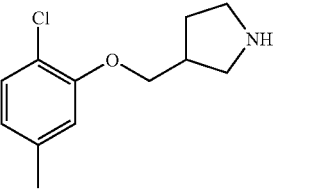 | O | NH |
| 116. | 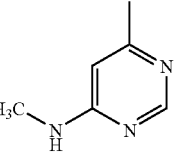 | 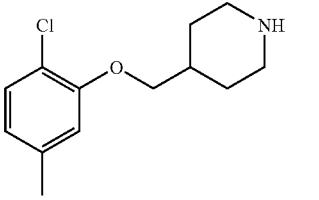 | O | NH |
| 117. | 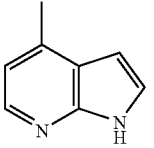 | 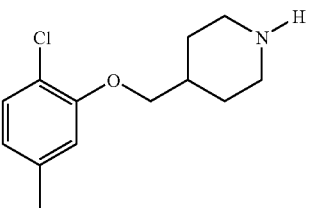 | O | NH |
| 118. | 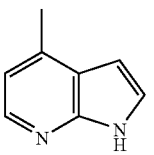 | 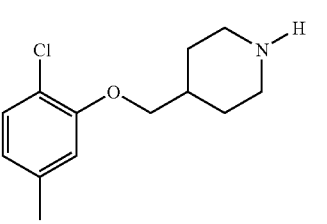 | O | NH |
| 119. | 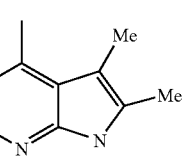 | | O | NH |

TABLE 5-continued

| # | R | R¹ | X | W¹ |
|---|---|----|---|-----|
| 120. | 2-Cl-5-Me-phenyl-O-CH₂CH₂-O-Me | 4-Me-7-azaindol-yl | O | NH |
| 121. | 5-Cl-2-Me-pyridin-yl | 4-Me-7-azaindol-yl | O | NH |
| 122. | 5-CF₃-2-Me-pyridin-yl | 4-Me-7-azaindol-yl | O | NH |
| 123. | 2-Cl-5-Me-phenyl-NH-CH₂-(1-Me-pyrrolidin-2-yl) | 3-CH₃NH(C=O)-4-pyridyl | O | NH |
| 124. | 2-Cl-5-Me-phenyl-NH-CH₂-(1-Me-pyrrolidin-2-yl) | 4-pyridyl | O | N |
| 125. | 2-Cl-5-Me-phenyl-NH-CH₂-(1-iPr-pyrrolidin-2-yl) | 3-CH₃NH(C=O)-4-pyridyl | O | NH |
| 126. | 2-Cl-5-Me-phenyl-O-CH₂CH₂-pyrrolidin-1-yl | 2-MeNH-4-pyrimidinyl | O | NH |

TABLE 6

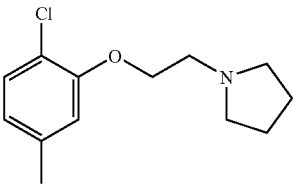

| # | R¹ | R | X | W¹ |
|---|---|---|---|---|
| 127. | 2-chlorophenyl | 4-pyridyl | O | NH |
| 128. | 5-benzimidazolyl | 4-pyridyl | S | NH |
| 129. | 2-chlorophenyl | 4-pyridyl | O | NMe |
| 130. | 2-quinolinyl | 4-pyridyl | O | NMe |
| 131. | 2-benzthiazolyl | 4-pyridyl | S | NMe |
| 132. | 2-benzimidazolyl | 3-CH₃NH(C=O)—4-pyridyl | CH₂ | NMe |
| 133. | 5-benzimidazolyl | 3-CH₃NH(C=O)—4-pyridyl | O | NMe |
| 134. | 6-benzimidazolyl | 3-CH₃NH(C=O)—4-pyridyl | S | NMe |
| 135. | 4-chlorophenyl | 3-CH₃NH(C=O)—4-pyridyl | O | NH |
| 136. | 3,4-dichlorophenyl | 3-CH₃NH(C=O)—4-pyridyl | NH | NH |
| 137. | 4-fluorophenyl | 4-quinolyl | CH₂ | NH |
| 138. | 3-chlorophenyl | 4-quinolyl | S | NH |
| 139. | 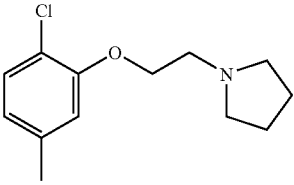 | 3-CH₃(C=O)NH—phenyl | O | NH |
| 140. | 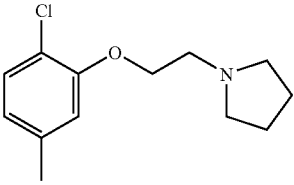 | 3-H₂N(C=O)phenyl | O | NH |
| 141. | 3-fluorophenyl | 4-quinolyl | NH | NH |
| 142. | 3-fluoro-4-methoxyphenyl | 4-quinolyl | O | NH |
| 143. | 3-fluoro-4-methylphenyl | 4-quinolyl | O | NH |
| 144. | 4-bromophenyl | 6,7-dimethoxy-4-quinolyl | NH | NH |
| 145. | 4-bromo-3-CF₃phenyl | 3-methyl-4-pyridyl | O | NH |
| 146. | 4-bromophenyl | 3-CH₃(C=O)NH—4-pyridyl | O | NH |
| 147. | 4-phenoxyphenyl | 3-CH₃NH(C=O)—phenyl | S | NH |
| 148. | 3-phenoxyphenyl | 3-CH₃NH(C=O)—phenyl | O | NH |
| 149. | 4-biphenyl | 2-MeNH-4-pyrimidinyl | O | NH |
| 150. | 4-cyclohexylphenyl | 2-MeNH-4-pyrimidinyl | NH | NH |
| 151. | 3-isoquinolyl | 2-MeNH-4-pyrimidinyl | O | NH |
| 152. | 3-quinolyl | 2-MeNH-4-pyrimidinyl | O | NH |
| 153. | 4-pyrimidinyl | 2-MeNH-4-pyrimidinyl | O | NH |
| 154. | 5-isoindolyl | 2-MeNH-4-pyrimidinyl | O | NH |
| 155. | | 2-MeNH-4-pyrimidinyl | | |

TABLE 6-continued

| # | R¹ | R | X | W¹ |
|---|---|---|---|---|
| 156. | 2-Cl, 5-Me-phenyl-O-CH₂CH₂-pyrrolidin-1-yl | 4-pyridyl | O | NH |
| 157. | 2-Cl, 5-Me-phenyl-O-CH₂CH₂-pyrrolidin-1-yl | 3-CH₃NH(C=O)—4-pyridyl | O | NH |
| 158. | 2-Cl, 5-Me-phenyl-O-CH₂CH₂-(3-dimethylamino)pyrrolidin-1-yl | 4-pyridyl | O | NH |
| 159. | 2-Cl, 5-Me-phenyl-O-CH₂CH₂-(3-dimethylamino)pyrrolidin-1-yl | 6,7-dimethoxy-4-methylquinazolinyl | O | NH |
| 160. | 2-Cl, 5-Me-phenyl-O-CH₂CH₂-(3-dimethylamino)pyrrolidin-1-yl | 3-CH₃NH(C=O)—4-pyridyl | O | NH |
| 161. | 2-Cl, 5-Me-phenyl-O-CH₂CH₂-(3-dimethylamino)pyrrolidin-1-yl | 2-MeNH-4-pyrimidinyl | O | NH |
| 162. | 2-Cl, 5-Me-phenyl-CH₂-(3-dimethylamino)pyrrolidin-1-yl | 4-pyridyl | O | NH |

TABLE 6-continued
| # | R¹ | R | X | W¹ |
|---|---|---|---|---|
| 163. | 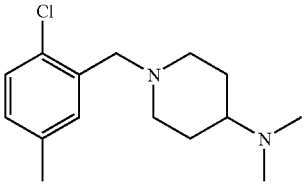 | 3-CH₃NH(C=O)—4-pyridyl | O | NH |
| 164. | 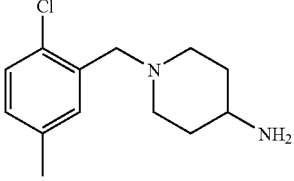 | 4-pyridyl | O | NH |
| 165. | 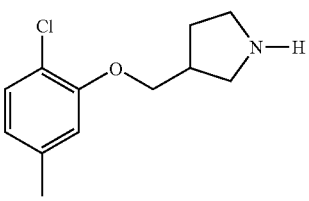 | 3-CH₃NH(C=O)—4-pyridyl | O | NH |
| 166. | 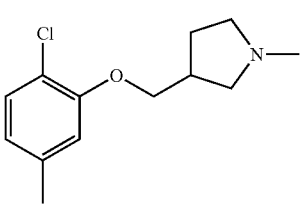 | 2-MeNH-4-pyrimidinyl | O | NH |
| 167. | 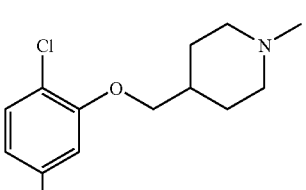 | 2-MeNH-4-pyrimidinyl | O | NH |
| 168. | 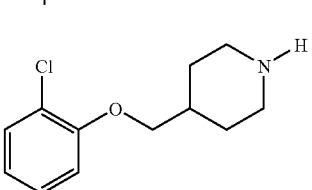 | 4-pyridyl | O | NH |
| 169. | 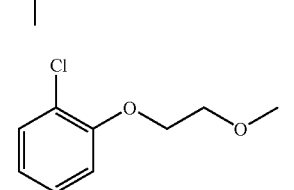 | 3-CH₃NH(C=O)—4-pyridyl | O | NH |

TABLE 6-continued

| # | R¹ | R | X | W¹ |
|---|---|---|---|---|
| 170. | 2-Cl, 5-Me-phenyl-O-CH₂CH₂-O-EtOMe | 2-MeNH-4-pyrimidinyl | O | NH |
| 171. | 5-Cl-2-Me-pyridin-3-yl | 2-MeNH-4-pyrimidinyl | O | NH |
| 172. | 5-CF₃-2-Me-pyridin-3-yl | 4-pyridyl | O | NH |
| 173. | 2-Cl, 5-Me-phenyl-O-CH₂-(1-methylpyrrolidin-2-yl) | 3-CH₃NH(C=O)—4-pyridyl | O | NH |
| 174. | 2-Cl, 5-Me-phenyl-NH-CH₂-(1-methylpyrrolidin-2-yl) | 4-quinolyl | O | NH |
| 175. | 2-Cl, 5-Me-phenyl-NH-CH₂-(pyrrolidin-2-yl) | 4-quinolyl | O | NH |
| 176. | 2-Cl, 5-Me-phenyl-O-CH₂CH₂-(pyrrolidin-1-yl) | 4-methyl-7-azaindolyl | O | NH |
| 177. | 2-Cl, 5-Me-phenyl-CH₂-(3-dimethylamino-pyrrolidin-1-yl) | 4-methyl-7-azaindolyl | O | NH |

TABLE 6-continued
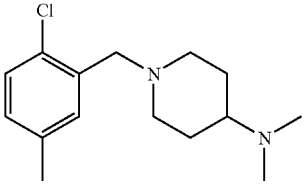
| # | R¹ | R | X | W¹ |
|---|----|----|---|----|
| 178. | 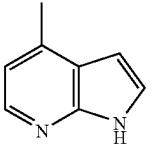 | 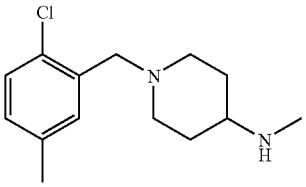 | O | NH |
| 179. | 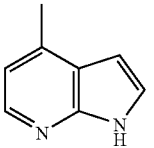 | 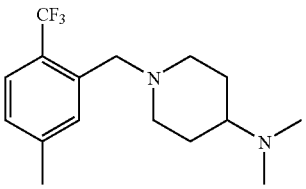 | O | NH |
| 180. | 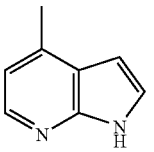 | 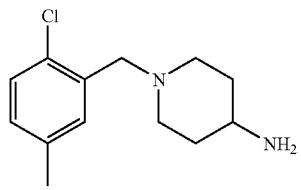 | O | NH |
| 181. | 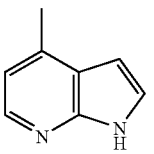 | 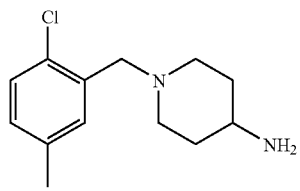 | O | NH |
| 182. | 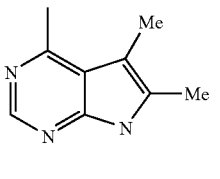 | 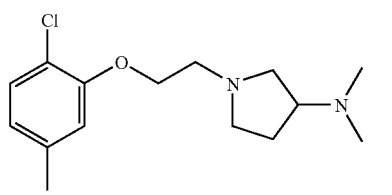 | O | NH |
| 183. | 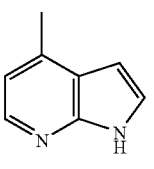 | 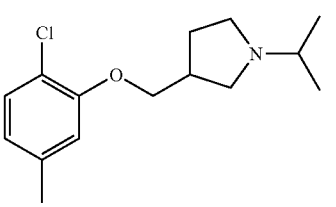 | O | NH |
| 184. |  | 2-MeNH-4-pyrimidinyl | O | NH |

TABLE 6-continued

| # | R¹ | R | X | W¹ |
|---|----|---|---|-----|
| 185. | 2-chloro-5-methylphenoxymethyl-pyrrolidine (NH) | 4-methyl-7-azaindole | O | NH |
| 186. | 2-chloro-5-methylphenoxymethyl-pyrrolidine (NH) | 4-methyl-1,3-dihydro-2H-pyrrolo[2,3-b]pyridin-2-one | O | NH |
| 187. | 2-bromo-5-methylphenoxymethyl-N-methylpyrrolidine | 4-methyl-7-azaindole | O | NH |
| 188. | 2-chloro-5-methylphenoxymethyl-N-methylpyrrolidine | 4-methyl-7-azaindole | O | NH |
| 189. | 2-chloro-5-methylphenoxymethyl-N-methylpyrrolidine | 6-methyl-4-(methylamino)pyrimidine | O | NH |
| 190. | 2-chloro-5-methylphenoxymethyl-N-isopropylpiperidine | 4-methyl-7-azaindole | O | NH |

TABLE 6-continued
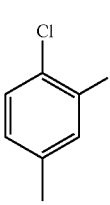
| # | R¹ | R | X | W¹ |
|---|----|---|---|----|
| 191. | 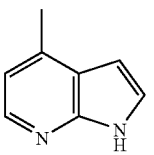 | 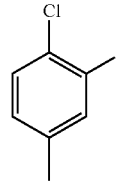 | O | NH |
| 192. | 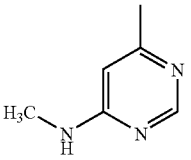 | 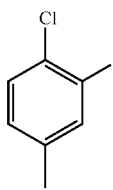 | O | NH |
| 193. | 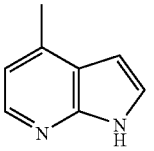 | 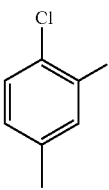 | O | NH |
| 194. | 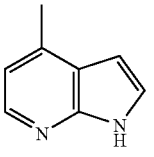 | 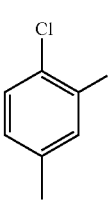 | O | NH |
| 195. | 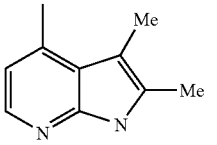 | 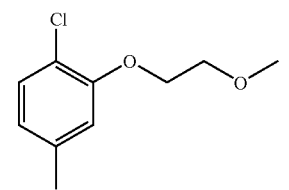 | O | NH |
| 196. | 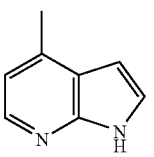 | 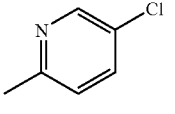 | O | NH |
| 197. | 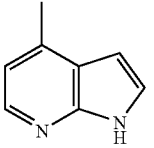 | | O | NH |

TABLE 6-continued
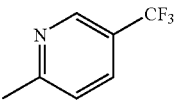
| # | R¹ | R | X | W¹ |
|---|---|---|---|---|
| 198. | 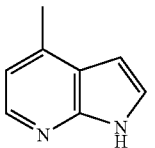 | 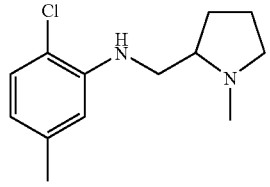 | O | NH |
| 199. | 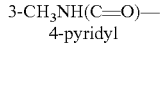 | 3-CH₃NH(C=O)—4-pyridyl | O | NH |
| 200. | 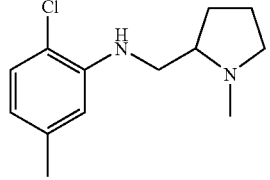 | 4-pyridyl | O | N |
| 201. | 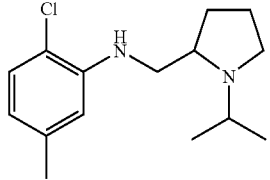 | 3-CH₃NH(C=O)—4-pyridyl | O | NH |
| 202. | 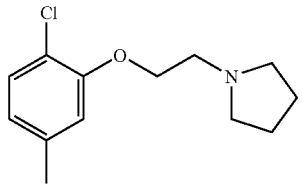 | 2-MeNH-4-pyrimidinyl | O | NH |
TABLE 7
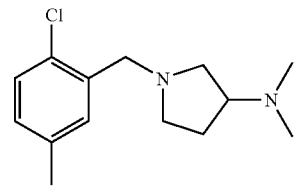
| # | R | R¹ | X | W¹ |
|---|---|---|---|---|
| 203. | 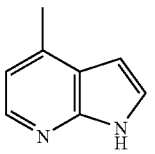 | 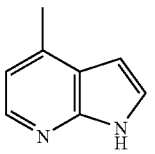 | O | NH |

TABLE 7-continued
| # | R | R¹ | X | W¹ |
|---|---|----|---|----|
| 204. | 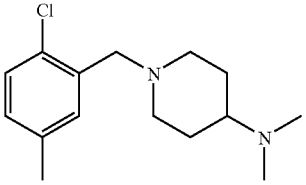 | 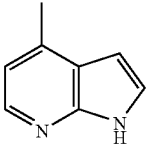 | O | NH |
| 205. | 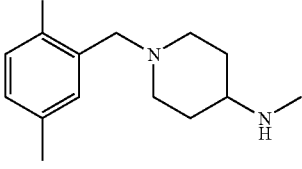 | 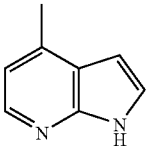 | O | NH |
| 206. | 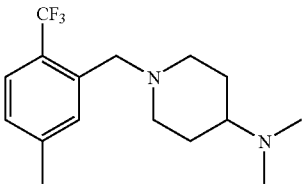 | 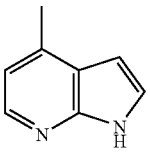 | O | NH |
| 207. | 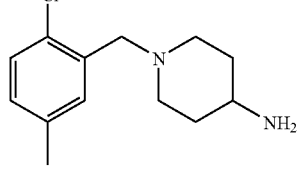 | 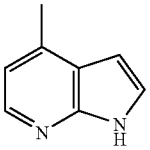 | O | NH |
| 208. | 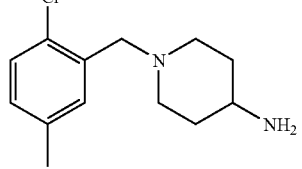 | 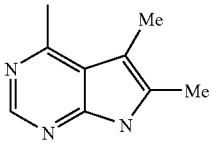 | O | NH |
| 209. | 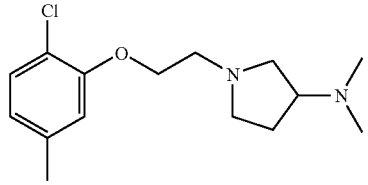 | 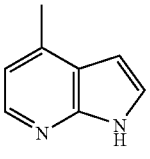 | O | NH |
| 210. | 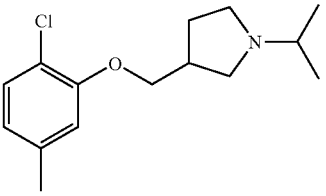 | 2-MeNH-4-pyrimidinyl | O | NH |

TABLE 7-continued

| # | R | R¹ | X | W¹ |
|---|---|----|---|----|
| 211. | 2-chloro-5-methylphenoxymethyl-pyrrolidin-3-yl (NH) | 4-methyl-7-azaindole | O | NH |
| 212. | 2-chloro-5-methylphenoxymethyl-pyrrolidin-3-yl (NH) | 4-methyl-1,3-dihydro-pyrrolo[2,3-b]pyridin-2-one | O | NH |
| 213. | 2-bromo-5-methylphenoxymethyl-1-methylpyrrolidin-3-yl | 4-methyl-7-azaindole | O | NH |
| 214. | 2-chloro-5-methylphenoxymethyl-1-methylpyrrolidin-3-yl | 4-methyl-7-azaindole | O | NH |
| 215. | 2-chloro-5-methylphenoxymethyl-1-methylpyrrolidin-3-yl | 6-methyl-N-methylpyrimidin-4-amine | O | NH |
| 216. | 2-chloro-5-methylphenoxymethyl-1-isopropylpiperidin-4-yl | 4-methyl-7-azaindole | O | NH |

TABLE 7-continued
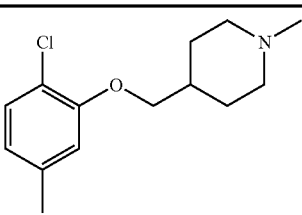
| # | R | R¹ | X | W¹ |
|---|---|----|---|-----|
| 217. | 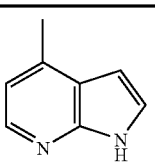 | 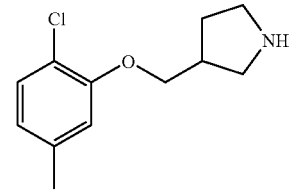 | O | NH |
| 218. | 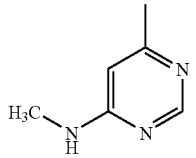 | 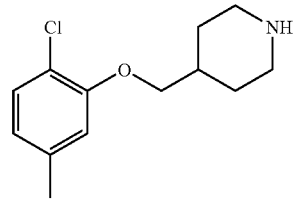 | O | NH |
| 219. | 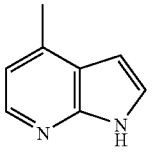 | 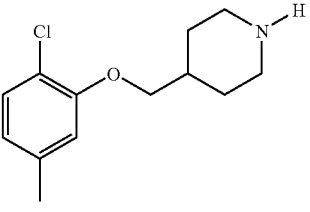 | O | NH |
| 220. | 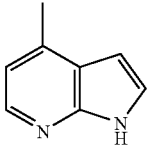 | 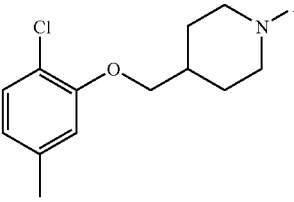 | O | NH |
| 221. | 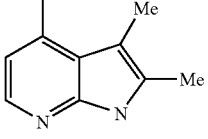 | 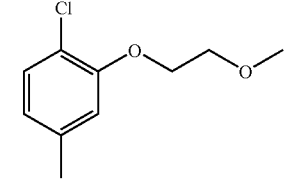 | O | NH |
| 222. | 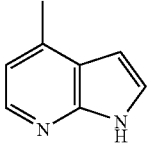 | 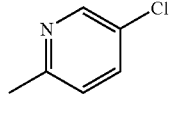 | O | NH |
| 223. | 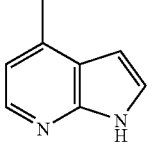 | 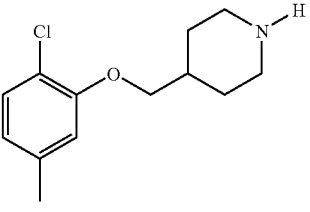 | O | NH |

TABLE 7-continued

*Structure: R¹—X—benzoxazole—W₁—R (5-substituted benzoxazole with R at 2-position via W₁)*

| # | R | R¹ | X | W¹ |
|---|---|---|---|---|
| 224. | 6-methyl-5-(trifluoromethyl)pyridin-3-yl (2-methyl-5-CF₃-pyridyl) | 4-(7-azaindolyl) (1H-pyrrolo[2,3-b]pyridin-4-yl) | O | NH |
| 225. | 2-chloro-5-methylphenyl-NH-CH₂-(1-methylpyrrolidin-2-yl) | 3-CH₃NH(C=O)—4-pyridyl | O | NH |

TABLE 8

*Structure: R¹—X—benzimidazole(N-R⁴)—W₁—R*

| # | R | R¹ | X | W¹ | R⁴ |
|---|---|---|---|---|---|
| 226. | 2-chloro-5-methylphenoxy-CH₂CH₂-pyrrolidin-1-yl | 4-pyridyl | O | NH | CH₃ |
| 227. | 2-chloro-5-methylphenoxy-CH₂CH₂-pyrrolidin-1-yl | 3-CH₃NH(C=O)—4-pyridyl | O | NH | Et |
| 228. | 2-chloro-5-methylphenoxy-CH₂CH₂-[3-(dimethylamino)pyrrolidin-1-yl] | 4-pyridyl | O | NH | CH₃ |
| 229. | 2-chloro-5-methylphenoxy-CH₂CH₂-[3-(N-methyl-N-(6,7-dimethoxyquinazolin-4-yl)amino)pyrrolidin-1-yl] | | O | NH | CH₃ |

TABLE 8-continued

| # | R | R¹ | X | W¹ | R⁴ |
|---|---|---|---|---|---|
| 230. | 2-chloro-5-methylphenoxyethyl-(3-dimethylamino)pyrrolidin-1-yl | 3-CH₃NH(C=O)—4-pyridyl | O | NH | CH₃ |
| 231. | 2-chloro-5-methylphenoxyethyl-(3-dimethylamino)pyrrolidin-1-yl | 2-MeNH-4-pyrimidinyl | O | NH | CH₃ |
| 232. | 2-chloro-5-methylbenzyl-(3-dimethylamino)pyrrolidin-1-yl | 4-pyridyl | O | NH | CH₃ |
| 233. | 2-chloro-5-methylbenzyl-(4-dimethylamino)piperidin-1-yl | 3-CH₃NH(C=O)—4-pyridyl | O | NH | CH₃ |
| 234. | 2-chloro-5-methylbenzyl-(4-amino)piperidin-1-yl | 4-pyridyl | O | NH | CH₃ |
| 235. | 2-chloro-5-methylphenoxymethyl-pyrrolidin-3-yl (NH) | 3-CH₃NH(C=O)—4-pyridyl | O | NH | CH₃ |

EXAMPLE 236

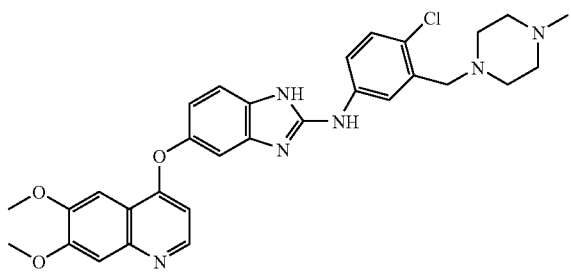

[4-Chloro-3-(4-methylpiperazin-1-ylmethyl)-phenyl]-[5-(6,7-dimethoxyquinolin-4-yloxy)-1H-benzimidazol-2-yl]-amine Step A: 4-(3,4-Dinitrophenoxy)-6,7-dimethoxyquinoline A mixture of 6,7-dimethoxy-4-chloroquinoline (0.35 g, 1.6 mmol) and 3,4-dinitrophenol (0.85 g, 4.6 mmol) was heated to 150° C. for 4 h. The mixture was cooled at RT and MeOH added. The reaction was stirred for 3 h. The precipitate filtered out and was washed with MeOH to afford 4-(3,4-dinitrophenoxy)-6,7-dimethoxyquinoline.

Step B: 4-(6,7-Dimethoxyquinolin-4-yloxy)-benzene-1,2-diamine 4-(3,4-Dinitrophenoxy)-6,7-dimethoxyquinoline (Step a, 0.256 g) was dissolved in THF (40 mL) and HOAc (1 mL) was added followed by zinc dust (1.3 g). Mixture was stirred at RT for 3 h and filtered through a Celite® pad. Solvent was evaporated and residue was washed with NaOH 1 M and extracted with EtOAc. The organic phase was dried, filtered and evaporated to give the title compound.

Step C: [4-Chloro-3-(4-methylpiperazin-1-ylmethyl)-phenyl]-[5-(6,7-dimethoxyquinolin-4-yloxy)-1H-benzimidazol-2-yl]-amine The title compound was prepared according to the procedure similar to that described for Example 26 using the appropriate isothiocyanate. (MH$^+$)=559; Calc'd 558.2 for $C_{30}H_{31}ClN_6O_3$.

EXAMPLE 237

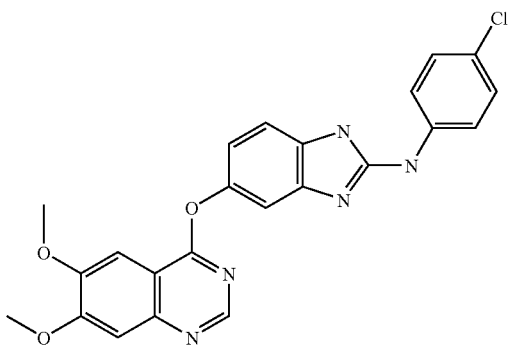

(4-Chlorophenyl)-[5-(6,7-dimethoxyquinazolin-4-yloxy)-1H-benzimidazol-2-yl]-amine Step A: 4-(6,7-Dimethoxyquinazolin-4-yloxy)-2-nitro-phenylamine A solution of 4-amino-3-nitrophenol (0.8 g, 5.34 mmol, 1.2 eq) in DMSO (3.8 mL, 5×) was treated with KOt-Bu (0.6 g, 5.34 mmol, 1.2 eq), and the mixture was stirred at RT for 2 h. The contents were treated with 4-chloro-6,7-dimethoxyquinazoline (1.0 g, 4.45 mmol, 1.0 eq) and $K_2CO_3$ (0.33 g, 2.4 mmol, 0.53 eq) then heated at 110° C. for 16 h. The mixture was cooled to RT, diluted with EtOAc and washed with NaHCO$_3$ (sat). To remove the emulsion, the mixture was filtered through Celite, then the organic layer was washed with brine, 1N NaOH, then brine again. The organic portion was dried with Na$_2$SO$_4$, filtered and evaporated to give the title compound as a brown solid. MS(MH$^+$)=343.1; Calc'd 342.31 for $C_{16}H_{14}N_4O_5$.

Step B: 4-(6,7-Dimethoxy-quinazolin-4-yloxy)-benzene-1,2-diamine 4-(6,7-Dimethoxyquinazolin-4-yloxy)-2-nitro-phenylamine (Step A, 1 g, 2.9 mmol) was dissolved in EtOH (200 mL) and glacial acetic acid (10 mL) and placed under nitrogen. Pd/C was added, the reaction mixture blanketed with H$_2$, the mixture was shaken under H$_2$ for 18 h at 55 psi. The catalyst was removed by filtration through Celite® and the solution was concentrated in vacuo. The residue was dissolved in MeOH/H$_2$O and NH$_4$OH was added to adjust to PH 10, and the solvent evaporated. Purification of the residue by column chromatography using a gradient of 0-100% of a 90:10:1 (CH$_2$Cl$_2$:MeOH: NH$_4$OH) afforded the title compound as a orange solid. MS(MH$^+$)=N/A; Calc'd 312.32 for $C_{16}H_{16}N_4O_3$.

Step C: (4-Chloro-phenyl)-[5-(6,7-dimethoxy-quinazolin-4-yloxy)-1H-benzoimidazol-2-yl]-amine The title compound was prepared similarly to Example 1, using the corresponding thioisocyanate. MS(MH$^+$)=448.1; Calc'd 447.87 for $C_{23}H_{18}ClN_5O_3$.

EXAMPLE 238

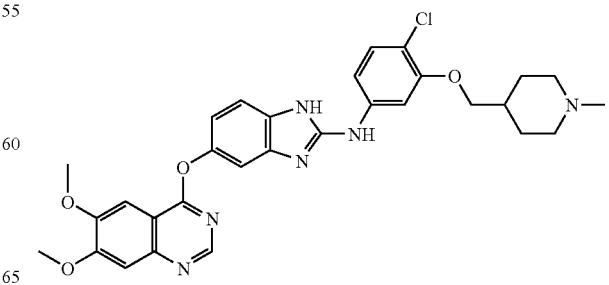

[4-Chloro-3-(1-methylpiperidin-4-ylmethoxy)-phenyl]-[5-(6,7-dimethoxyquinazolin-4-yloxy)-1H-benzimidazol-2-yl]-amine The title compound was prepared similarly as Example 237, using the corresponding thioisocyanate. MS(MH+)= 575.1; Calc'd 574.21 for $C_{30}H_{31}ClN_6O_4$.

EXAMPLE 239

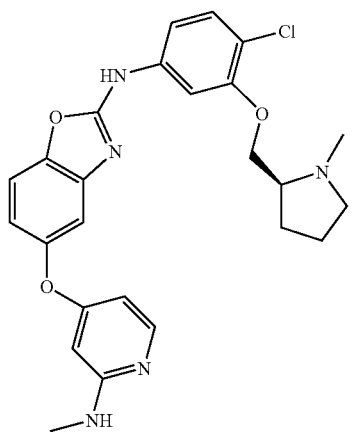

[4-Chloro-3-((2S)-1-methylpyrrolidin-2-ylmethoxy)-phenyl]-[5-(2-methylamino-pyridin-4-yloxy)-benzoxazol-2-yl]-amine Step A: 4-(4-Benzyloxy-phenoxy)-2-chloro-pyridine To a stirring RT suspension of NaH (0.739 g of a 60% by weight oil dispersion, 18.48 mmol) in DMF (20 mL) was added 4-benzyloxy phenol (3.70 g, 18.48 mmol). The mix was stirred 10 min before cooling to 0° C. and adding 2,4-dichloropyridine (2.734 g, 18.48 mmol). The reaction was warmed to RT. After stirring for 60 h, the reaction was quenched with saturated aqueous NaHCO₃ and then basified with 2N NaOH. The crude was extracted twice with Et₂O. The organic layers were washed three times with 2 N NaOH, once with brine, then combined and dried over Na₂SO₄, filtered and dried in vacuo. The crude residue was eluted on a silica gel column with a hexanes/EtOAc system to yield title compound, isolated as the major regioisomer.

Step B: [4-(4-Benzyloxy-phenoxy)-pyridin-2-yl]-methylamine

In a 350 mL sealed tube fitted with stirring bar were combined at 0° C. 4-(4-benzyloxy-phenoxy)-2-chloro-pyridine (Step a, 2.11 g, 6.79 mmol), DMSO (10 mL), DIEA (1.3 mL, 7.47 mmol), and CH₃NH₂ (4.1 mL of a 2 N solution in THF, 8.15 mmol). The reaction was heated to 100° C. for 7 days. During that period, an additional amount of CH₃NH₂ solution was added on four separate days (for a total of 70 mL). The reaction was cooled to RT and diluted into 1N NaOH and Et₂O after evaporating off THF. After separation of the layers, the organic layer was washed 3× with 1 N NaOH then with brine. The crude residue was eluted on a silica gel column with a hexanes/EtOAc gradient to yield the title compound.

Step C: 4-(2-Methylamino-pyridin-4-yloxy)-phenol

The title compound was prepared according to a procedure similar to that described for Step C of Example 30.

Step D: 4-(2-Methylamino-pyridin-4-yloxy)-2-nitrophenol

The title compound was prepared according to a procedure similar to that described for Step D of Example 30.

Step E: 2-Amino-4-(2-methylamino-pyridin-4-yloxy)-phenol

The title compound was prepared according to a procedure similar to that described for Step E of Example 30.

Step F: [4-Chloro-3-((2S)-1-methyl-pyrrolidin-2-ylmethoxy)-phenyl]-[5-(2-methyl-amino-pyridin-4-yloxy)-benzoxazol-2-yl]-amine To a stirring RT solution of 2-amino-4-(2-methylamino-pyridin-4-yloxy)-phenol (Step e, 84 mg, 0.363 mmol) in CH₃CN (10 ml) and DMF (2 ml) was added (2S)-2-(2-chloro-5-isothiocyanato-phenoxymethyl)-1-methyl-pyrrolidine (102.7 mg, 0.363 mmol). The following day, the CH₃CN was evaporated off, and the crude mix was diluted into 1N NaOH and EtOAc. The layers were separated. The aqueous layer was extracted 3× with EtOAc, and the combined organic layers were washed once with 1N NaOH and once with brine. The organic layer was then dried over Na₂SO₄, filtered and concentrated in vacuo. The crude residue was purified by thin layer silica gel chromatography to yield the title compound. MS (MH+)=480.2; Calc'd 479.17 for $C_{25}H_{26}ClFN_5O_3$.

EXAMPLE 240

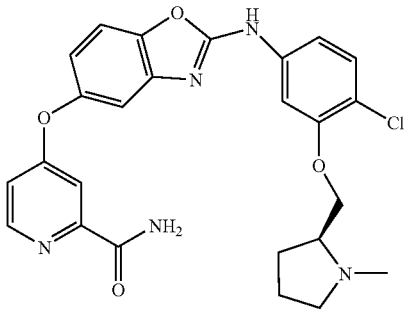

4-{2-[4-Chloro-3-((2S)-1-methylpyrrolidin-2-ylmethoxy)-phenylamino]-benzoxazol-5-yloxy}-pyridine-2-carboxylic acid amide Step A: 4-Chloro-pyridine-2-carboxylic acid amide Aqueous NH₄OH (40%, 250 mL) was added dropwise at 0° C. to a suspension of 4-chloro-pyridine-2-carbonyl chloride (75 g, 533 mmol) in EtOAc. Upon addition, the temperature rose to 30° C. The mixture was stirred for 2 h at RT then kept at RT for 12 h without stirring. MTBE (250 mL) was added to the mixture and the resulting emulsion was filtered. The solid was washed with EtOAc. The MTBE/EtOAc layer was washed twice with water and once with 5% Na₂CO₃, then dried over MgSO₄ and concentrated under vacuum. The resulting solid was suspended in EtOAc several times and filtered out to give the desired compound.

Step B: 4-(4-Benzyloxy-phenoxy)-pyridine-2-carboxylic acid amide

The title compound was prepared according to a procedure similar to that described for Step A of Example 32. MS (MH+)=321.1; Calc'd 320.35 for $C_{19}H_{16}N_2O_3$.

Step C: 4-(4-Hydroxy-phenoxy)-pyridine-2-carboxylic acid amide

The title compound was prepared according to a procedure similar to that described for Step C of Example 30.

Step D: 4-(4-Hydroxy-3-nitro-phenoxy)-pyridine-2-carboxylic acid amide

The title compound was prepared according to a procedure similar to that described for Step D of Example 30.

Step E: 4-(3-Amino-4-hydroxy-phenoxy)-pyridine-2-carboxylic acid amide

The title compound was prepared according to a procedure similar to that described for Step E of Example 30.

Step F: 4-{2-[4-Chloro-3-((2S)-1-methyl-pyrrolidin-2-ylmethoxy)-phenylamino]-benzooxazol-5-yloxy}-pyridine-2-carboxylic acid amide To a stirring RT solution of 4-(3-amino-4-hydroxy-phenoxy)-pyridine-2-carboxylic acid amide (Step d, 217 mg, 0.884 mmol) in CH$_3$CN (30 ml) and DMF (3 mL) was added (2S)-2-(2-chloro-5-isothiocyanato-phenoxymethyl)-1-methyl-pyrrolidine (208 mg, 0.737 mmol). The following day, the CH$_3$CN was evaporated off, and the crude mix was diluted into 1N NaOH and EtOAc. The layers were separated. The aqueous layer was extracted 3× with EtOAc, and the combined organic layers were washed once with 1N NaOH and once with brine. The organic layer was then dried over Na$_2$SO$_4$, filtered and concentrated in vacuo. The crude residue was purified by silica gel chromatography to yield the title compound. (MH$^+$)=494.2; Calc'd 493.15 for C$_{25}$H$_{24}$ClN$_5$O$_4$.

EXAMPLE 241

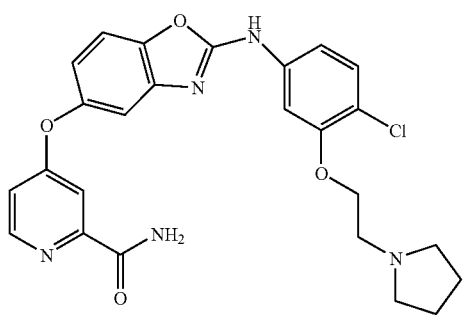

4-{2-[4-Chloro-3-(2-pyrrolidin-1-yl-ethoxy)-phenylamino]-benzoxazol-5-yloxy}-pyridine-2-carboxylic acid amide The title compound was prepared from 4-(3-amino-4-hydroxy-phenoxy)-pyridine-2-carboxylic acid amide and the appropriate isothiocyanate according to a procedure similar to that used in Example 240. MS (MH$^+$)=494.2; Calc'd 493.15 for C$_{25}$H$_{24}$ClN$_5$O$_4$.

EXAMPLE 242

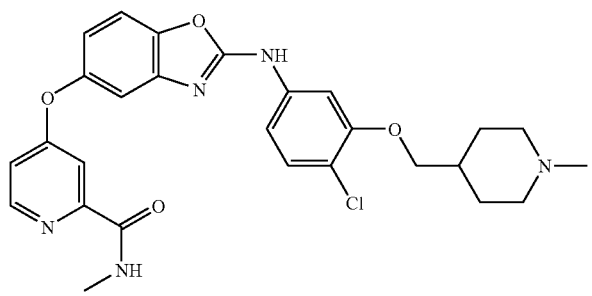

4-{2-[4-Chloro-3-(1-methylpiperidin-4-ylmethoxy)-phenylamino]-benzoxazol-5-yloxy}-pyridine-2-carboxylic acid methylamide The title compound was prepared similarly as Example 32, using the corresponding thioisocyanate. MS(MH$^+$)=522.1; Calc'd 521.18 for C$_{27}$H$_{28}$ClN$_5$O$_4$.

EXAMPLE 243

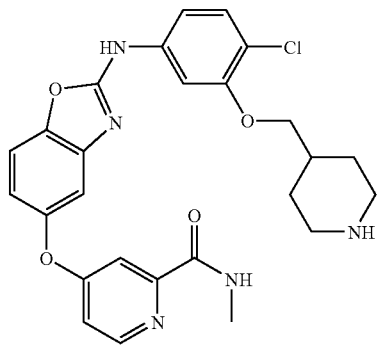

4-{2-[4-Chloro-3-(piperidin-4-ylmethoxy)-phenylamino]-benzoxazol-5-yloxy}-pyridine-2-carboxylic acid methylamide Step A: 4-(5-Amino-2-chloro-phenoxymethyl)-piperidine-1-carboxylic acid tert-butyl ester The title compound was prepared similarly as Preparation V, using 4-(2-chloro-5-nitro-phenoxymethyl)-piperidine-1-carboxylic acid tert-butyl ester. MS(MH$^+$)=NA; Calc'd 340.16 for C$_{17}$H$_{25}$ClN$_2$O$_3$.

Step B: 4-(2-Chloro-5-isothiocyanato-phenoxymethyl)-piperidine-1-carboxylic acid tert-butyl ester The title compound was prepared similarly as Preparation III using the corresponding aniline. MS(MH$^+$)=NA; Calc'd 382.11 for C$_{18}$H$_{23}$ClN$_2$O$_3$S.

Step C: 4-{2-Chloro-5-[5-(2-methylcarbamoyl-pyridin-4-yloxy)-benzoxazol-2-ylamino]-phenoxymethyl}-piperidine-1-carboxylic acid tert-butyl ester The title compound was prepared similarly as Example 32, using the corresponding thioisocyanate. The compound was used crude in the next reaction. MS(MH$^+$)=NA; Calc'd 607.22 for C$_{31}$H$_{34}$ClN$_5$O$_6$.

Step D: 4-{2-[4-Chloro-3-(piperidin-4-ylmethoxy)-phenylamino]-benzoxazol-5-yloxy}-pyridine-2-carboxylic acid methylamide 4-{2-Chloro-5-[5-(2-methylcarbamoyl-pyridin-4-yloxy)-benzoxazol-2-ylamino]-phenoxymethyl}-piperidine-1-carboxylic acid tert-butyl ester was dissolved in TFA (2 mL). After stirring for 2 h at RT, the mixture was concentrated in vacuo and taken up into EtOAc and washed with NaOH, then NaHCO$_3$ (sat). The organic layer was dried with Na$_2$SO$_4$, filtered and evaporated. The title compound was obtained after purification by prepatory HPLC as a white solid. MS(MH$^+$)=508.1; Calc'd 507.17 for C$_{26}$H$_{26}$ClN$_5$O$_4$.

EXAMPLE 244

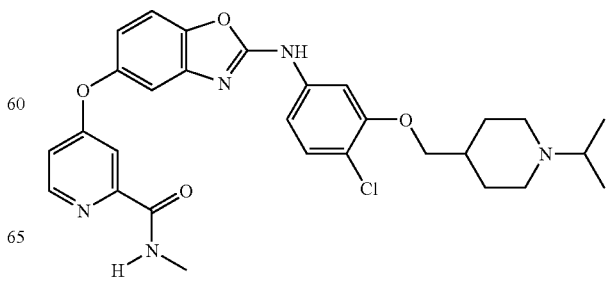

4-{2-[4-Chloro-3-(1-isopropylpiperidin-4-yl-methoxy)-phenylamino]-benzoxazol-5-yloxy}-pyridine-2-carboxylic acid methyl amide The title compound was prepared similarly as Example 32, using the corresponding thioisocyanate. MS(MH$^+$)=550.1; Calc'd 549.21 for $C_{29}H_{32}ClN_5O_4$.

EXAMPLE 245

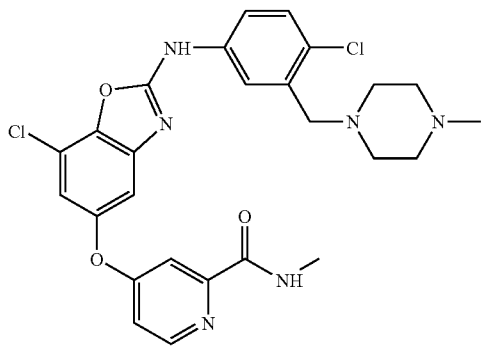

4-{7-Chloro-2-[4-chloro-3-(4-methyl-piperazin-1-ylmethyl)-phenylamino]-benzoxazol-5-yloxy}-pyridine-2-carboxylic acid methyl amide The title compound was prepared similarly as Example 261 starting with 4-benzyloxy-3-chloro-phenol (Example 257, Step A) and 4-chloro-pyridine-2-carboxylic acid methylamide, using the corresponding thioisocyanate. MS(MH$^+$)= 541.1; Calc'd 540.14 for $C_{26}H_{26}Cl_2N_6O_3$.

EXAMPLE 246

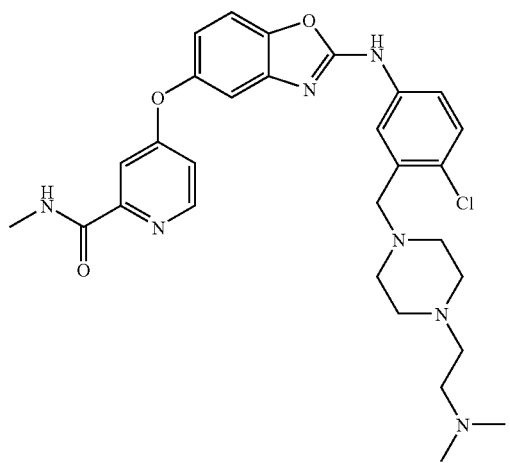

4-[2-{4-Chloro-3-[4-(2-dimethylamino-ethyl)-piperazin-1-ylmethyl]-phenylamino}-benzoxazol-5-yloxy)-pyridine-2-carboxylic acid methylamide 4-(3-Amino-4-hydroxy-phenoxy)-pyridine-2-carboxylic acid methylamide (prepared as described in Example 32, 200 mg, 0.8 mmol, 1.0 eq.) was dissolved in CH$_3$CN (15 mL) and {2-[4-(2-chloro-5-isothiocyanato-benzyl)-piperazin-1-yl]-ethyl}-dimethyl-amine (prepared as described in preparation III, CH$_3$CN used as solvent rather than CH$_2$Cl$_2$, 260 mg, 0.8 mmol, 1.0 eq.) as a CH$_3$CN solution was added dropwise. The reaction was stirred at RT for 16 h. EDC (150 mg, 0.8 mmol, 1.0 eq.) was added and the reaction was heated to 80° C. for 2 h. The mixture was concentrated and the crude product was purified by column chromatography (0-10% MeOH/CH$_2$Cl$_2$/1% NH$_4$OH) followed by Gilson reversed phase column purification to yield 4-[2-{4-chloro-3-[4-(2-dimethylamino-ethyl)-piperazin-1-ylmethyl]-phenylamino}-benzoxazol-5-yloxy)-pyridine-2-carboxylic acid methylamide. MS m/z=564.3 (M+H)+Calc'd for $C_{29}H_{34}ClN_7O_3$: 564.09.

EXAMPLE 247

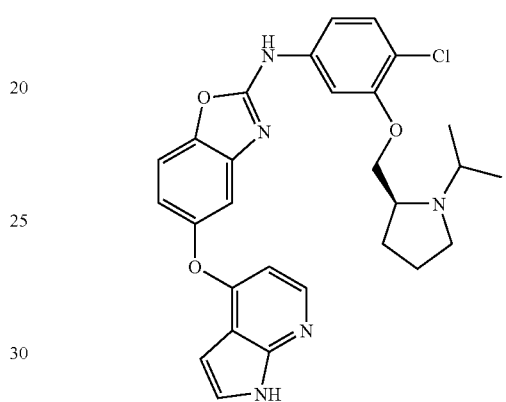

S-[4-Chloro-3-(1-isopropylpyrrolidin-2-ylmethoxy)-phenyl]-[5-(1H-pyrrolo[2,3-b]pyridin-4-yloxy)-benzoxazol-2-yl]-amine Step A: S-2-(2-Chloro-5-nitrophenoxymethyl)-1-isopropyl-pyrrolidine S-2-(2-Chloro-5-nitro-phenoxymethyl)-pyrrolidine (Preparation X, 3.0 g, 11 mmol, 1.0 eq.) was dissolved into CH$_2$Cl$_2$ (100 mL) and (CH$_3$)$_2$C(O) (6.4 g, 11 mmol, 1.0 eq.) was added followed by Na(AcO)$_3$BH (3.3 g, 16 mmol, 1.4 eq.) The reaction was stirred at RT for 16 h. 2N NaOH (aq., 100 mL) was added and the biphasic mixture was stirred at RT for 16 h. The mixture was diluted with CH$_2$Cl$_2$ and 2N NaOH and the layers were separated. The organic layer was extracted with 1N HCl and the aqueous layer was basified with NaOH pellets. Extracted with EtOAc and washed with 2 N NaOH. The organic layer was dried over MgSO$_4$, filtered and concentrated to yield 2-(2-chloro-5-nitro-phenoxymethyl)-1-isopropyl-pyrrolidine. The CH$_2$Cl$_2$ layer was concentrated down to yield further material.

Step B: S-[4-Chloro-3-(1-isopropylpyrrolidin-2-ylmethoxy)-phenyl]-[5-(1H-pyrrolo[2,3-b]pyridin-4-yloxy)-benzoxazol-2-yl]-amine 2-Amino-4-(1H-pyrrolo[2,3-b]pyridin-4-yloxy)-phenol (0.2 g, 0.83 mmol, 1.0 eq.) was dissolved in a mixture of 10 ml THF/2.5 ml DMF (anhydrous). S-2-(2-Chloro-5-nitro-phenoxymethyl)-1-isopropyl-pyrrolidine (Step A, 0.26 g, 0.83 mmol, 1.0 eq.) was added dropwise as a THF (anhydrous) solution. The reaction was stirred at RT for 16 h. EDC (0.16 g, 0.83 mmol, 1.0 eq.) was added and the reaction was stirred for 2 h at 80° C. The mixture was cooled to RT and the formed solid was filtered. HCl salt of desired product. The solid was dissolved in EtOAc and washed with NaHCO$_3$ (aq. saturated). The organic layer was dried over MgSO$_4$, filtered and concentrated. MTBE was used to turn viscous oil into solid. Dried on high vacuum to obtain S-[4-chloro-3-(1-isopropyl-pyrrolidin-2-ylmethoxy)-phenyl]-[5-(1H-pyrrolo[2,3-b]pyridin-4-yloxy)-benzoxazol-2-yl]-amine. MS m/z=518.2 (M+H)$^+$ Calc'd for C$_{28}$H$_{28}$N$_5$O$_3$: 517.19.

EXAMPLE 248

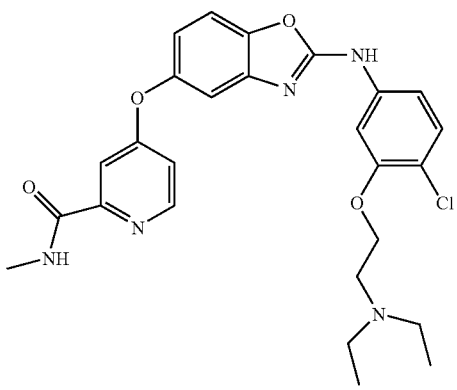

4-{2-[4-Chloro-3-(2-diethylamino-ethoxy)-phenylamino]-benzoxazol-5-yloxy}-pyridine-2-carboxylic acid methylamine Step A: 4-{2-[4-Chloro-3-(2-chloro-ethoxy)-phenylamino]-benzoxazolo-5-yloxy}-pyridine-2-carboxylic acid methylamide To a stirring RT solution of 4-(3-amino-4-hydroxy-phenoxy)-pyridine-2-carboxylic acid methylamide (1.51 g, 5.824 mmol) in DMF (8 mL) and CH$_3$CN (80 mL) was added 1-chloro-2-(2-chloro-ethoxy)-4-isothiocyanato-benzene (1.39 g, about 5.3 mmol) contaminated with some of the corresponding 2-bromo-ethoxy. The reaction was stirred over 4 days at RT. The reaction was heated over night to 50° C. after addition of EDC reagent (1.02 g, 5.30 mmol). The CH$_3$CN was evaporated off, and the crude mix was diluted into 1 N NaOH and EtOAc. The organic phase was washed with brine, dried over Na$_2$SO$_4$, filtered, and concentrated in vacuo. Silica gel chromatography of the crude residue yielded the title compound. (MH$^+$)=473.1; Calc'd 473.32 for C$_{22}$H$_{18}$Cl$_2$N$_4$O$_4$.

Step B: 4-{2-[-4-Chloro-3-(2-diethylamino-ethoxy)-phenylamino]-benzoxazol-5-yloxy}-pyridine-2-carboxylic acid methylamine 4-{2-[4-Chloro-3-(2-chloro-ethoxy)-phenylamino]-benzooxazolo-5-yloxy}-pyridine-2-carboxylic acid methylamide (Step a, 156 mg, 0.33 mmol) was combined in a sealed tube with DMSO (1 mL) and excess DEA (0.5 mL). The reaction was heated with stirring for 2 days at 85° C. The reaction was treated with 1N NaOH and extracted 3 times with EtOAc. The combined organic layers were washed with brine, dried over Na$_2$SO$_4$, filtered, and concentrated in vacuo. Purification of the crude residue by thin layer silica gel chromatography yielded the title compound. (MH$^+$)=510.2; Calc'd 509.18 for C$_{26}$H$_{28}$ClN$_5$O$_4$.

The following compounds were prepared from the respective amines according to a procedure similar to that described in Step B.

| Ex. | Structure | Mol. Formula | mass | MS (MH+) |
|---|---|---|---|---|
| 249 | 4-{2-[4-Chloro-3-(2-dimethylamino-ethoxy)-phenylamino]-benzoxazol-5-yloxy}-pyridine-2-carboxylic acid methylamide | C$_{24}$H$_{24}$ClN$_5$O$_4$ | 481.15 | 482.1 |

| Ex. | Structure | Mol. Formula | mass | MS (MH+) |
|---|---|---|---|---|
| 250 | 4-(2-{4-Chloro-3-[2-(3-dimethylamino-pyrrolidin-1-yl)-ethoxy]-phenylamino}-benzoxazol-5-yloxy)-pyridine-2-carboxylic acid methylamide | $C_{28}H_{31}ClN_6O_4$ | 550.21 | 551.2 |
| 251 | 4-(2-{4-Chloro-3-[2-(4-methyl-piperazin-1-yl)-ethoxy]-phenylamino}-benzoxazol-5-yloxy)-pyridine-2-carboxylic acid methylamide | $C_{27}H_{29}ClN_6O_4$ | 536.19 | 537.2 |

EXAMPLE 252

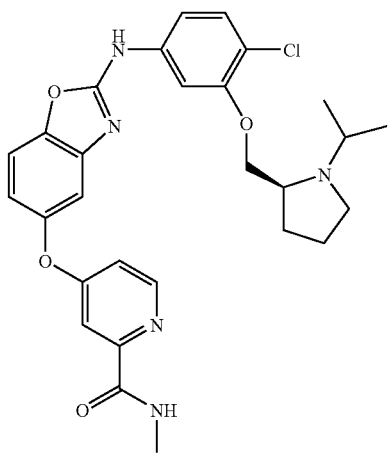

4-{2-[4-Chloro-3-((2S)-1-isopropyl-pyrrolidin-2-ylmethoxy)-phenylamino]-benzooxazol-5-yloxy}-pyridine-2-carboxilic acid methylamide The title compound was prepared similarly to the procedure outlined for Example 32. MS(MH+) 536.2; 535.20 Calc'd Mass for $C_{28}H_{30}ClN_5O_4$

EXAMPLE 253

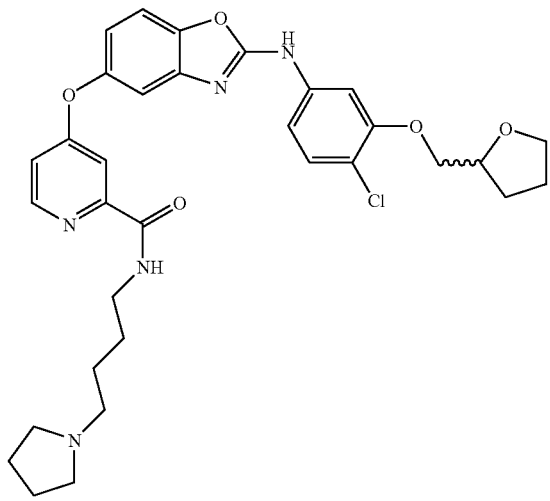

4-{2-[4-Chloro-3-(tetrahydro-furan-2-ylmethoxy)-phenylamino]-benzoxazol-5-yloxy}-pyridine-2-carboxylic acid (4-pyrrolidin-1-yl-butyl)-amide Step A: 4-Chloro-pyridine-2-carboxylic acid (4-pyrrolidin-1-yl-butyl)-amide To a suspension of 4-chloro-pyridine-2-carbonyl chloride (8.88 g, 49 mmol) in THF (100 mL) was added at 0° C. 4-pyrrolidin-1-yl-butylamine (7.0 g, 49 mmol). The reaction was stirred for 18 h at RT. The mixture was diluted with EtOAc, washed several time with aqueous 6 N NaOH and then brine, dried over $Na_2SO_4$, filtered, and concentrated in vacuo. The crude material was purified by flash chromatography using a gradient $CH_2Cl_2$/MeOH/$NH_4OH$ (100%, 0%, 0% to 90%, 10%, 1%). The pure fractions were combined and the solvents removed under vacuum. The title compound was obtained.

Step B: 4-(4-Benzyloxy-phenoxy)-pyridine-2-carboxylic acid (4-pyrrolidin-1-yl-butyl)-amide The title compound was prepared according to a procedure similar to that described for Step A of Example 32. MS (MH+)=446.3; Calc'd 445.57 for $C_{27}H_{31}N_3O_3$.

Step C: 4-(4-Hydroxy-phenoxy)-pyridine-2-carboxylic acid (4-pyrrolidin-1-yl-butyl)-amide The title compound was prepared according to a procedure similar to that described for Step C of Example 30. MS (MH+)=356.2; Calc'd 355.44 for $C_{20}H_{25}N_3O_3$.

Step D: 4-(4-Hydroxy-3-nitro-phenoxy)-pyridine-2-carboxylic acid (4-pyrrolidin-1-yl-butyl)-amide To a solution of 4-(4-hydroxy-phenoxy)-pyridine-2-carboxylic acid (4-pyrrolidin-1-yl-butyl)-amide (Step C, 2.0 g, 5.6 mmol) in HOAc (32 mL) at RT was added 70% HNO3 (0.56 g, 6.2 mmol). The reaction was stirred at RT for 18 h. An additional amount of 70% $HNO_3$ (0.56 g, 6.2 mmol) was added dropwise over 10 min, and the reaction was stirred for 2 h, after which it was slowly added to saturated aqueous $NaHCO_3$ and extracted with $CH_2Cl_2$. The organic layer was washed with $NaHCO_3$ and brine, dried over $Na_2SO_4$, filtered, and concentrated in vacuo. The crude residue was purified by silica gel chromatography to yield the title compound. MS (MH+)=401.2; Calc'd 400.44 for $C_{20}H_{24}N_4O_5$.

Step E: 4-(3-Amino-4-hydroxy-phenoxy)-pyridine-2-carboxylic acid (4-pyrrolidin-1-yl-butyl)-amide The title compound was prepared according to a procedure similar to that described for Step E of Example 30.

Step F: 4-{2-[4-Chloro-3-(tetrahydro-furan-2-ylmethoxy)-phenylamino]-benzoxazol-5-yloxy}-pyridine-2-carboxylic acid (4-pyrrolidin-1-yl-butyl)-amide To a stirring RT solution of 4-(3-amino-4-hydroxy-phenoxy)-pyridine-2-carboxylic acid (4-pyrrolidin-1-yl-butyl)-amide (Step E, 162 mg, 0.438 mmol) in $CH_3CN$ (20 mL) and DMF (2 mL) was added 2-(2-chloro-5-isothiocyanato-phenoxymethyl)-tetrahydro-furan (112 mg, 0.417 mmol). The following day, the $CH_3CN$ was evaporated off, and the crude mix was diluted into 1 N NaOH and EtOAc. The layers were separated. The aqueous layer was extracted 3× with EtOAc, and the combined organic layers were washed once with 1N NaOH and once with brine. The organic layer was dried over $Na_2SO_4$, filtered and concentrated in vacuo. The crude residue was purified by silica gel chromatography to yield the title compound as a yellow solid. MS(MH+)=606.3; Calc'd 605.24 for $C_{32}H_{36}ClN_5O_5$.

EXAMPLE 254

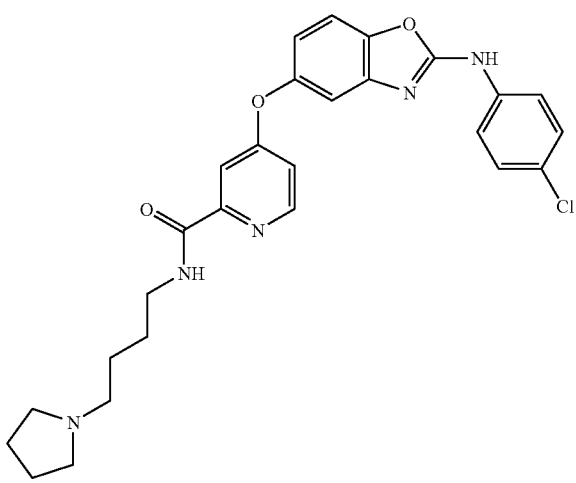

4-[2-(4-Chlorophenylamino)-benzoxazol-5-yloxy]-pyridine-2-carboxylic acid (4-pyrrolidin-1-yl-butyl)-amide 4-(3-Amino-4-hydroxy-phenoxy)-pyridine-2-carboxylic acid (4-pyrrolidin-1-yl-butyl)-amide (Example 253, Step E, 165 mg, 0.4 mmol, 1.0 eq.) was dissolved in $CH_3CN/DMF$ (2/1, v/v, 15 ml) and 1-chloro-4-isothiocyanato-benzene (as described in preparation III, 75 mg, 0.4 mmol, 1.0 eq.) in as a $CH_3CN$ solution was added dropwise. The reaction was stirred at RT for 16 h. EDC (85 mg, 0.4 mmol, 1.0 eq.) was added and the reaction was heated to 80° C. for 2 h. The mixture was concentrated and the crude product was purified by column chromatography (0-10% $MeOH/CH_2Cl_2/1\%$ $NH_4OH$) to yield 4-[2-(4-chloro-phenylamino)-benzoxazol-5-yloxy]-pyridine-2-carboxylic acid (4-pyrrolidin-1-yl-butyl)-amide. MS m/z=506.01 (M+H)+Calc'd for $C_{27}H_{28}ClN_5O_3$: 505.19.

EXAMPLE 255

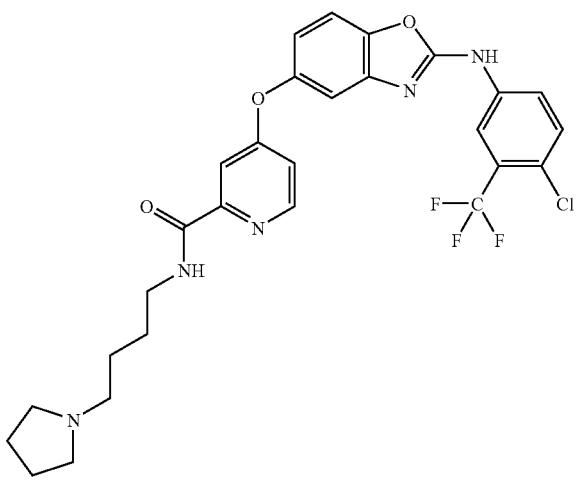

4-[2-(4-Chloro-3-trifluoromethylphenylamino)-benzoxazol-5-yloxy]-pyridine-2-carboxylic acid (4-pyrrolidin-1-yl-butyl)-amide 4-(3-Amino-4-hydroxy-phenoxy)-pyridine-2-carboxylic acid (4-pyrrolidin-1-yl-butyl)-amide (Example 253, Step E, 145 mg, 0.4 mmol, 1.0 eq.) was dissolved in $CH_3CN/DMF$ (2/1, v/v, 15 ml) and 1-chloro-4-isothiocyanato-2-trifluoromethyl-benzene (as described in preparation III, 93 mg, 0.4 mmol, 1.0 eq.) as a $CH_3CN$ solution was added drop-wise. The reaction was stirred at RT for 16 h. EDC (75 mg, 0.4 mmol, 1.0 eq.) was added and the reaction was heated to 80° C. for 2 h. The mixture was concentrated and the crude product was purified by column chromatography (0-10% $MeOH/CH_2Cl_2/1\%$ $NH_4OH$) to yield 4-[2-(4-chloro-3-trifluoromethyl-phenylamino)-benzoxazol-5-yloxy]-pyridine-2-carboxylic acid (4-pyrrolidin-1-yl-butyl)-amide. MS m/z=574.2 (M+H)+ Calc'd for $C_{28}H_{27}ClF_3N_5O_3$: 573.18.

EXAMPLE 256

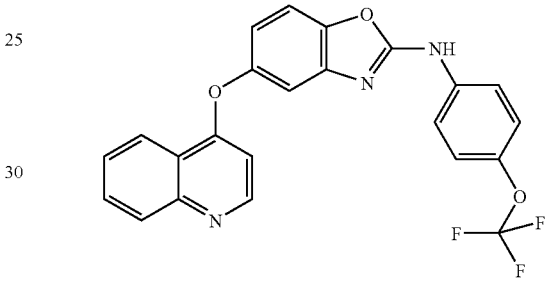

[5-(Quinolin-4-yloxy)-benzooxazol-2-yl]-(4-trifluoromethoxy-phenyl)-amine

Step A: 2-Amino-4-(quinolin-4-yloxy)-phenol

2-Nitro-4-(quinolin-4-yloxy)-phenol (prepared as described in Example 40, 3.1 g, 11 mmol, 1.0 eq.) was suspended into MeOH (100 mL) and the atmosphere was replaced by argon. The catalyst, 10% Pd/C, was added and the argon was replaced by a $H_2$ atmosphere. The mixture was stirred for 16 h at balloon pressure at RT until TLC showed reaction done. The Pd/C was filtered, the MeOH removed and the crude was purified by column chromatography (10-100% EtOAc/Hexane to 2% MeOH/EtOAc) to yield 2-amino-4-(quinolin-4-yloxy)-phenol.

Step B: [5-(Quinolin-4-yloxy)-benzooxazol-2-yl]-(4-trifluoromethoxy-phenyl)-amine 2-Amino-4-(quinolin-4-yloxy)-phenol (Step a, 174 mg, 0.7 mmol, 1.0 eq.) was dissolved in $CH_3CN/DMF$ (1/1, v/v, 4 mL) and 1-isothiocyanato-4-trifluoromethoxy-benzene (prepared as described in preparation III, 151 mg, 0.7 mmol, 1.0 eq.) was added dropwise as a $CH_3CN$ solution. The reaction was stirred at RT for 16 h. EDC (132 mg, 0.7 mmol, 1.0 eq.) was added and the reaction was heated to 80° C. for 2 h. The solvents were evaporated and some crystals formed in the residual oil. $CH_2Cl_2$ was added and the crystals were filtered to give [5-(quinolin-4-yloxy)-benzoxazol-2-yl]-(4-trifluoromethoxyphenyl)-amine. MS m/z=438.1 (M+H)+ Calc'd for $C_{23}H_{14}F_3N_3O_3$: 437.10.

EXAMPLE 257

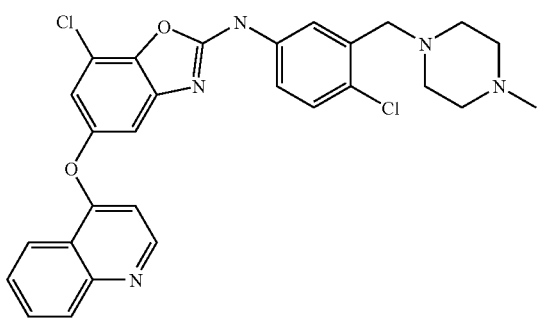

[4-Chloro-3-(4-methyl-piperazin-1-ylmethyl)-phenyl]-[7-chloro-5-(quinolin-4-yloxy)-benzoxazol-2-yl]-amine Step A: 4-Benzyloxy-3-chlorophenol To a solution of 4-benzyloxy-3-chlorobenzaldehyde (4 g, 16.2 mmol) in $CH_2Cl_2$ (65 mL), m-CPBA (3.63 g, 77% max, 21.05 mmol) was added and stirred at RT for 5 days. The mixture was washed with a $Na_2S_2O_3$ solution, then $NaHCO_3$ (sat), and evaporated. The residue was suspended in MeOH (150 mL), NaOMe (0.5 M in MeOH, 60 mL) was added and the mixture was stirred for 1 h. The mixture was concentrated, and the residue was dissolved in water, and extracted with $Et_2O$/EtOAc. The aqueous layer was acidified, and extracted with EtOAc. The combined organic portions were dried with $Na_2SO_4$, filtered and evaporated. The mixture was purified by column chromatography using $CH_2Cl_2$ as the eluent to yield an off-white solid. $MS(MH^+)$=NA; Calc'd 361.09 for $C_{22}H_{16}ClNO_2$.

Step B: [4-Chloro-3-(4-methylpiperazin-1-ylmethyl)-phenyl]-[7-chloro-5-(quinolin-4-yloxy)-benzoxazol-2-yl]-amine The title compound was prepared similarly to the procedure outlined for Example 261, starting with 4-chloroquinoline and 4-benzyloxy-3-chlorophenol in Step A. $MS(MH^+)$=534.1; Calc'd 533.14 for $C_{28}H_{25}Cl_2N_5O_2$.

EXAMPLE 258

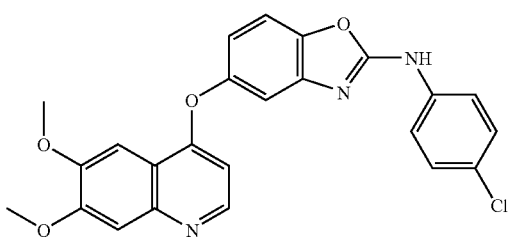

(4-Chlorophenyl)-[5-(6,7-dimethoxyquinolin-4-yloxy)-benzoxazol-2-yl]-amine

The title compound was prepared similarly to the procedure outlined for Example 40, starting with 4-chloro-6,7-dimethoxyquinoline and using the corresponding thioisocyanate. $MS(MH^+)$=448.0; Calc'd 447.10 for $C_{24}H_{18}ClN_3O_4$.

EXAMPLE 259

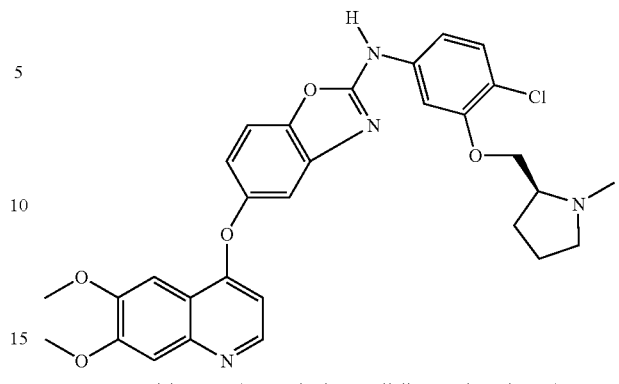

S-[4-Chloro-3-(1-methylpyrrolidin-2-ylmethoxy)-phenyl]-[5-(6,7-dimethoxyquinolin-4-yloxy)-benzoxazol-2-yl]-amine The title compound was prepared according the procedure similar to that described for Example 40 using the appropriate isothiocyanate. $(MH^+)$=561; Calc'd 560.18 for $C_{30}H_{29}ClN_4O_5$.

EXAMPLE 260

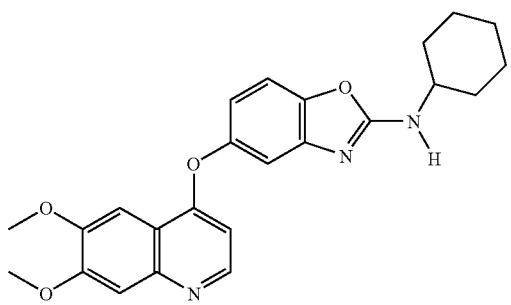

Cyclohexyl-[5-(6,7-dimethoxyquinolin-4-yloxy)-benzoxazol-2-yl]-amine

The title compound was prepared according the procedure similar to that described for Example 40 using the appropriate isothiocyanate. $(MH^+)$=420; Calc'd 419.18 for $C_{24}H_{25}N_3O_4$.

EXAMPLE 261

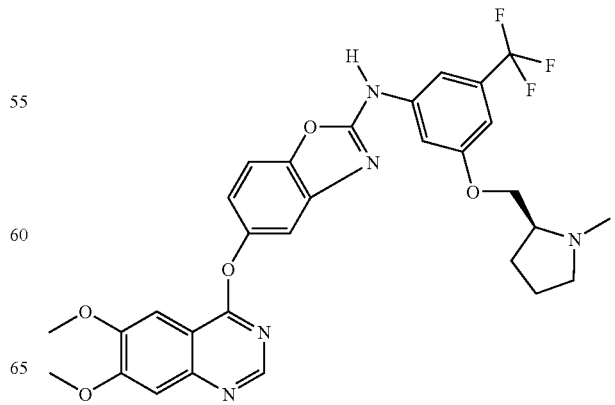

S-[5-(6,7-Dimethoxyquinazolin-4-yloxy)-benzoxazol-2-yl]-[3-(1-methylpyrrolidin-2-ylmethoxy)-5-trifluoromethylphenyl]-amine Step A: 4-(4-Benzyloxyphenoxy)-6,7-dimethoxyquinazoline The title compound was prepared similarly to Example 30, Step A, starting from 4-chloro-6,7-dimethoxyquinazoline with a temperature of 90° C. The compound was purified by column chromatography using 90:10:1 (CH$_2$Cl$_2$:MeOH:NH$_4$OH) as the eluent. MS(MH$^+$)=NA; Calc'd 388.42 for C$_{23}$H$_{20}$N$_2$O$_4$.

Step B: 4-(6,7-Dimethoxyquinazolin-4-yloxy)-phenol 4-(4-Benzyloxy-phenoxy)-6,7-dimethoxyquinazoline (1.2 g) was heated at reflux with TFA (10 mL) for 20 h, and the mixture was concentrated in vacuo. The residue was diluted with water and basicified with NH$_4$OH (conc.) and a solid precipitated. The solid as filtered, washed with water and Et$_2$O and used directly in the next step. MS(MH$^+$)=NA; Calc'd 298.30 for C$_{16}$H$_{14}$N$_2$O$_4$.

Step C: 4-(6,7-Dimethoxyquinazolin-4-yloxy)-2-nitrophenol

The title compound was prepared similarly to Example 30, Step D. MS(MH$^+$)=NA; Calc'd 343.29 for C$_{16}$H$_{13}$N$_3$O$_6$.

Step D: 2-Amino-4-(6,7-dimethoxyquinazolin-4-yloxy)-phenol 4-(6,7-Dimethoxyquinazolin-4-yloxy)-2-nitrophenol (Step c, 350 mg, 1.02 mmol) was combined with Fe (1.17 g), 6N HCl (2 drops), water (2.1 mL) and EtOH (9 mL) and heated at reflux for 2.5 h. The hot mixture was filtered through Celite and evaporated. The residue was purified by column chromatography using 0-30% of a 90:10:1 (CH$_2$Cl$_2$:MeOH:NH$_4$OH) solution in CH$_2$Cl$_2$ as the eluent. MS(MH$^+$)=NA; Calc'd 313.31 for C$_{16}$H$_{15}$N$_3$O$_4$.

Step E: S-[5-(6,7-Dimethoxyquinazolin-4-yloxy)-benzoxazol-2-yl]-[3-(1-methylpyrrolidin-2-ylmethoxy)-5-trifluoromethyl-phenyl]-amine The title compound was prepared similarly to Example 30, Step F using the corresponding thioisocyanate. MS(MH$^+$)= 596.1; Calc'd 595.20 for C$_{30}$H$_{27}$F$_3$N$_5$O$_5$.

EXAMPLE 262

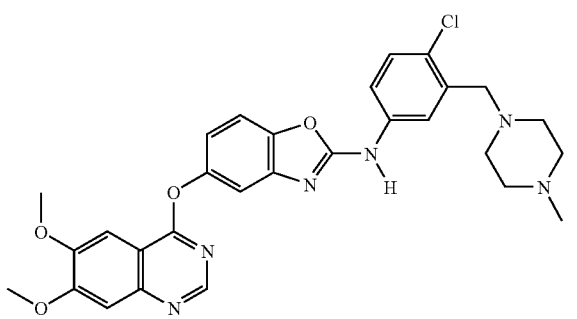

[4-Chloro-3-(4-methyl-piperazin-1-ylmethyl)-phenyl]-[5-(6,7-dimethoxy-quinazolin-4-yloxy)-benzoxazol-2-yl]-amine The title compound was prepared similarly to Example 261 (Steps A-E) using the corresponding thioisocyanate. MS(MH$^+$)=561.1; Calc'd 560.19 for C$_{29}$H$_{29}$ClN$_6$O$_4$.

EXAMPLE 263

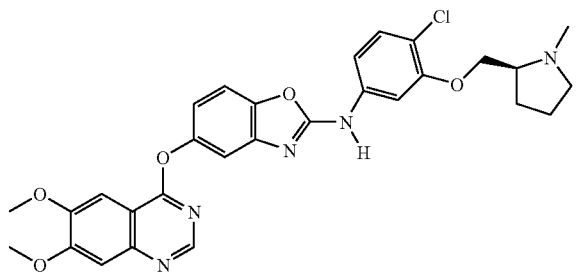

S-[4-Chloro-3-(1-methyl-pyrrolidin-2-ylmethoxy)-phenyl]-[5-(6,7-dimethoxy-quinazolin-4-yloxy)-benzoxazol-2-yl]-amine The title compound was prepared according the procedure similar to that described for Example 261 (Step A-E) using the appropriate isothiocyanate. (MH$^+$)=562; Calc'd 561.18 for C$_{29}$H$_{28}$ClN$_5$O$_5$.

EXAMPLE 264

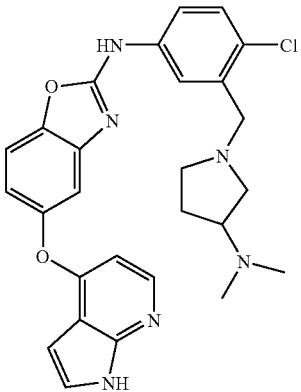

[4-Chloro-3-(3-dimethylamino-pyrrolidin-1-ylmethyl)-phenyl]-[5-(1H-pyrrolo[2,3-b]pyridin-4-yloxy)-benzoxazol-2-yl]-amine Step A: 4-(4-Benzyloxy-phenoxy)-1H-pyrrolo[2,3-b]pyridine To a N$_2$ purged round bottom flask was added 4-chloro-7-azaindole (15.8 g, 104 mmol, 1.0 eq.) followed by 4-benzyloxyphenol (41.5 g, 207 mmol, 2.0 eq), 20 ml of TFA/Et$_3$N (1/1, 107 mmol, 1.0 eq.) and DMAP (13 g, 106 mmol, 1.0 eq.). The reaction was heated to 140° C. for 48 h. The mixture was cooled to RT and diluted with CH$_2$Cl$_2$ (100 mL) Silica gel was added and the mixture was evaporated to dryness onto the silica. The crude mixture was purified by column chromatography (20-100% EtOAc/Hexane) to give 4-(4-benzyloxy-phenoxy)-1H-pyrrolo[2,3-b]pyridine.

Step B: 4-(1H-Pyrrolo[2,3-b]pyridin-4-yloxy)phenol 4-(4-Benzyloxy-phenoxy)-1H-pyrrolo[2,3-b]pyridine (Step a, 9.0 g, 28.4 mmol, 1.0 eq.) was suspended into MeOH (200 mL) and the atmosphere was replaced by argon. 10% Pd/C (3 g total), was added and the argon was replaced by a $H_2$ atmosphere. The mixture was stirred for 16 h at 60 psi at RT (using Parr shaker). The reaction showed about 50% conversion to product (monitored by HPLC). More 10% Pd/C was added and reacted another 16 h at 60 psi. More 10% Pd/C was added and reacted another 16 h at 60 psi. TLC showed reaction done. The Pd/C was filtered, the MeOH removed and the obtained 4-(1H-pyrrolo[2,3-b]pyridin-4-yloxy)phenol was used crude in the next step.

Step C: 2-Nitro-4-(1H-pyrrolo[2,3-b]pyridin-4-yloxy)-phenol 4-(1H-Pyrrolo[2,3-b]pyridin-4-yloxy)phenol (Step b, 5.6 g, 24.8 mmol, 1.0 eq.) was dissolved into AcOH (100 ml) and $HNO_3$ (70%, 2.4 mL, 26.7, 1.1 eq.) was added dropwise. The reaction was stirred for 1 h at RT. The acids were removed by evaporation and the residue was taken up in $NaHCO_3$ (aq., saturated, 100 mL) and $CH_2Cl_2$ (200 mL). Separated the layers and washed the organic layers with $NaHCO_3$ (aq., saturated, 50 mL) and brine (50 mL). Back extracted aqueous layers with $CH_2Cl_2$ (100 ml) and dried the combined organic layers over $MgSO_4$, filtered and concentrated. Further purification by column chromatography (0-100% EtOAc/Hexane) yielded 2-nitro-4-(1H-pyrrolo[2,3-b]pyridin-4-yloxy)-phenol.

Step D: 2-Amino-4-(1H-pyrrolo[2,3-b]pyridin-4-yloxy)-phenol

2-Nitro-4-(1H-pyrrolo[2,3-b]pyridin-4-yloxy)-phenol (Step c, 3 g, 11.1 mmol) was dissolved into MeOH (100 mL) and the atmosphere was replaced by argon. A catalytic amount of 10% Pd/C was added and the argon was replaced by a $H_2$ atmosphere. The mixture was stirred for 16 h at RT at balloon pressure. The Pd/C was filtered and the obtained 2-amino-4-(1H-pyrrolo[2,3-b]pyridin-4-yloxy)-phenol was used crude in the next step.

Step E: [1-(2-Chloro-5-nitro-benzyl)-pyrrolidin-3-yl]-dimethyl-amine

2-Chloro-5-nitrobenzaldehyde (5.0 g, 27 mmol) and 3-N,N-dimethylpyrrolidine (racemic, 3.1 g, 27 mmol, 1.0 eq.) were dissolved into $CH_2Cl_2$ (100 ml) and $Na(AcO)_3BH$ (8.0 g, 38 mmol, 1.4 eq.) was added. The reaction was stirred at RT for 16 h. NaOH (2N, 100 ml) was added and the biphasic layers were stirred at RT for 16 h. The mixture was further diluted with $CH_2Cl_2$ and 2 N NaOH (100 mL of each) and the layers were separated. The organic layer was extracted with 1N HCl (aq.) and basified with NaOH pellets (exotherm was observed). Extracted with EtOAc, washed with 2 N NaOH and brine/2N NaOH. Dried ($MgSO_4$), filtered and concentrated to yield [1-(2-chloro-5-nitro-benzyl)-pyrrolidin-3-yl]-dimethylamine.

Step F: [1-(5-Amino-2-chloro-benzyl)-pyrrolidin-3-yl]-dimethyl-amine 1

[1-(2-Chloro-5-nitro-benzyl)-pyrrolidin-3-yl]-dimethyl-amine (Step e, 7 g, 24.7 mmol, 1.0 eq.) was dissolved into EtOH (400 ml). $SnCl_2$ (14 g, 74.1 mmol, 3.0 eq.) was added and the reaction was heated to 80° C. for 18 h. The mixture was cooled down to RT and quenched with 1N $K_2CO_3$ (aq.) until bubbling had ceased. The white solids that had formed were filtered over Celite® and washed with EtOH. The filtrate was concentrated and redissolved in EtOAc (100 mL). Washed with 2 N NaOH (50 ml) and 2N NaOH/brine (50 mL). The organic layer was dried ($MgSO_4$), filtered and concentrated to yield [1-(5-amino-2-chloro-benzyl)-pyrrolidin-3-yl]-dimethyl-amine.

Step G: [1-(2-chloro-5-isothiocyanato-benzyl)-pyrrolidin-3-yl]-dimethyl-amine

[1-(5-Amino-2-chloro-benzyl)-pyrrolidin-3-yl]-dimethyl-amine (Step f, 1.2 g, 4.7 mmol, 1.0 eq.) was dissolved into $CH_2Cl_2$ (100 ml) and 1,1'-thiocarbonyldiimidazole (0.85 g, 4.7 mmol, 1.0 eq.) was added. The reaction was stirred at RT for 2 h. TLC showed conversion of starting material into product. Concentrated down to dryness and purified by column chromatography (100% EtOAc) to give [1-(2-chloro-5-isothiocyanato-benzyl)-pyrrolidin-3-yl]-dimethyl-amine.

Step H: [4-chloro-3-(3-dimethylamino-pyrrolidin-1-ylmethyl)-phenyl]-[5-(1H-pyrrolo[2,3-b]pyridin-4-yloxy)-benzoxazol-2-yl]-amine

[1-(5-Amino-2-chloro-benzyl)-pyrrolidin-3-yl]-dimethyl-amine (0.25 g, 1.0 mmol, 1.0 eq.) was dissolved into THF (10 mL, anhydrous) and DMF (5 mL, anhydrous) [1-(2-chloro-5-isothiocyanato-benzyl)-pyrrolidin-3-yl]-dimethyl-amine (Step g, 0.29 g, 1.0 mmol, 1.0 eq.) was added drop-wise as a THF solution. The reaction was stirred at RT for 16 h. EDC (0.18 g, 1.0 mmol, 1.0 eq.) was added and the reaction was heated to 80° C. for 2 h. The solvents were removed and the crude was purified by column chromatography (0-10% MeOH/$CH_2Cl_2$, 1% $NH_4OH$). Further purification was required utilizing the Gilson semi-preparative HPLC to obtain [4-chloro-3-(3-dimethylamino-pyrrolidin-1-ylmethyl)-phenyl]-[5-(1H-pyrrolo[2,3-b]pyridin-4-yloxy)-benzoxazol-2-yl]-amine. MS m/z=503.2 $(M+H)^+$ Calc'd for $C_{27}H_{27}N_6O_2$: 503.01.

EXAMPLE 265

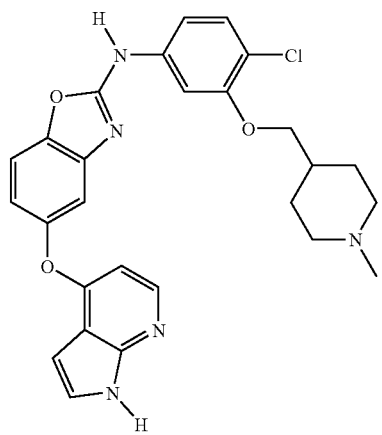

[4-Chloro-3-(1-methyl-piperidin-4-ylmethoxy)-phenyl]-[5-(1H-pyrrolo[2,3-b]pyridin-4-yloxy)-benzoxazol-2-yl]-amine The title compound was prepared similarly as Example 264, using the corresponding thioisocyanate. MS(MH$^+$)= 504.1; Calc'd 503.17 for $C_{27}H_{26}ClN_5O_3$.

EXAMPLE 266

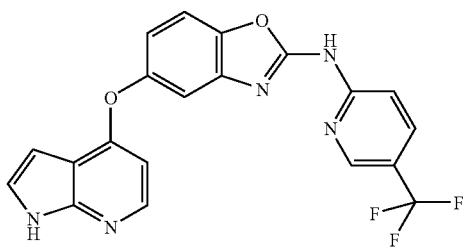

[5-(1H-Pyrrolo[2,3-b]pyridin-4-yloxy)-benzoxazol-2-yl]-(5-trifluoromethyl-pyridin-2-yl)-amine 4-(1H-Pyrrolo[2,3-b]pyridin-4-yloxy)phenol (prepared as described in Example 264, 200 mg, 0.8 mmol, 1.0 eq.) was dissolved in $CH_3CN$/DMF (10/3 ml respectively) and 2-isothiocyanato-5-trifluoromethyl-pyridine (prepared as described in preparation III, 170 mg, 0.8 mmol, 1.0 eq.) was added. The reaction was stirred at RT for 9 days. EDC (160 mg, 0.8 mmol, 1.0 eq.) was added and the reaction was heated to 80° C. for 2 h. The mixture was cooled down and filtered. The crude product was purified by column chromatography (0-5% EtOH/$CH_2Cl_2$). Pure fractions crystallized. Solid collected by filtration to give the title compound. MS m/z=412.1 $(M+H)^+$ Calc'd for $C_{20}H_{12}F_3N_5O_2$: 411.09.

Although the pharmacological properties of the compounds of Formula I-III vary with structural change, in general, activity possessed by compounds of Formula I-III may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed inhibition of KDR kinase at doses less than 50 μM.

Biological Evaluation

HUVEC Proliferation Assay

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of $3 \times 10^5$ cells/mL. Another cell count is performed to confirm the cell concentration. The cells are diluted to $3 \times 10^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+10% FBS+antibiotics (400× dilution). Medium containing 0.25% DMSO is also prepared for the 0 μM compound sample. After 22-h, the medium is removed from the cells, and 100 μL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. $IC_{50}$ values are then determined.

Examples 6, 13a, 13c, 17, 28-29, 32, 36, 38-39, 45-47, 49, 236-237, 238-240, 242-249, 252, 257, 259 and 263-265 inhibited VEGF-stimulated HUVEC proliferation at a level below 100 nm.

Angiogenesis Model

To determine the effects of the present compounds on angiogenesis in vivo, selective compounds are tested in the rat corneal neovascularization micropocket model or the angiogenesis assay of Passaniti, Lab. Invest., 67:519-528 (1992).

Rat Corneal Neovascularization Micropocket Model

In Life Aspects: Female Sprague Dawley rats weighing approximately 250 g are randomized into one of five treatment groups. Pretreatment with the vehicle or compound is administered orally, 24 h prior to surgery and continued once a day for seven additional days. On the day of surgery, the rats are temporarily anesthetized in an Isofluorane gas chamber (delivering 2.5 L/min oxygen+5% Isofluorane). An othoscope is then placed inside the mouth of the animal to visualize the vocal cords. A tip-blunted wire is advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) is connected to the endotracheal tube to deliver a mixture of oxygen and 3% Isofluorane. Upon achieving deep anesthesia, the whiskers are cut short and the eye areas and eyes gently ished with Betadine soap and rinsed with sterile saline. The corneas are irrigated with one to two drops of Proparacaine HCl ophthalmic topical anesthetic solution (0.5%) (Bausch and Lomb Pharmaceuticals, Tampa Fla.). The rat is then positioned under the dissecting microscope and the corneal surface brought into focus. A vertical incision is made on the midline of the cornea using a diamond blade knife. A pocket is created by using fine scissors to separate the connective tissue layers of the stroma, tunneling towards the limbus of the eye. The distance between the apex of the pocket and the limbus is approximately 1.5 mm. After the pocket had been made, the soaked nitrocellulose disk filter (Gelman Sciences, Ann Arbor Mich.) is inserted under the lip of the pocket. This surgical procedure is performed on both eyes. rHu-bFGF soaked disks are placed into the right eye, and the rHu-VEGF soaked disks are placed into the left eye. Vehicle soaked disks are placed in both eyes. The disk is pushed into position at the desired distance from the limbal vessels. Ophthalmic antibiotic ointment is applied to the eye to prevent drying and infection. After 7 days, the rats are euthanized by $CO_2$ asphyxiation, and the eyes enucleated. The retinal hemisphere of the eye is windowed to facilitate fixation, and the eye placed into formalin overnight.

Post Mortem Aspects: After 24 h in fixative, the corneal region of interest is dissected out from the eye, using fine forceps and a razorblade. The retinal hemisphere is trimmed off and the lens extracted and discarded. The corneal dome is bisected and the superfluous cornea trimmed off. The iris, conjunctiva and associated limbal glands are then carefully teased away. Final cuts are made to generate a square 3×3 mm containing the disk, the limbus, and the entire zone of neovascularization.

Gross Image Recording: The corneal specimens are digitally photographed using a Sony CatsEye DKC5000 camera (A.G. Heinz, Irvine Calif.) mounted on a Nikon SMZ-U stereo microscope (A.G. Heinz). The corneas are submerged in distilled water and photographed via trans-illumination at approximately 5.0 diameters magnification.

Image analysis: Numerical endpoints are generated using digital micrographs collected from the whole mount corneas after trimming and are used for image analysis on the Metamorph image analysis system (Universal Imaging Corporation, West Chester Pa.). Three measurements are taken: Disk placement distance from the limbus, number of vessels intersecting a 2.0 mm perpendicular line at the midpoint of the disk placement distance, and percent blood vessel area of the diffusion determined by thresholding.

General Formulations:

0.1% BSA in PBS vehicle: 0.025 g of BSA is added to 25.0 mL of sterile 1× phosphate buffered saline, gently shaken until fully dissolved, and filtered at 0.2 µm. Individual 1.0 mL samples are aliquoted into 25 single use vials, and stored at −20° C. until use. For the rHu-bFGF disks, a vial of this 0.1% BSA solution is thawed at RT. Once thawed, 10 µL of a 100 mM stock solution of DTT is added to the 1 mL BSA vial to yield a final concentration of 1 mM DTT in 0.1% BSA.

rHu-VEGF Dilutions:

Prior to the disk implant surgery, 23.8 µL of the 0.1% BSA vehicle above is added to a 10 µg rHu-VEGF lyophilized vial yielding a final concentration of 10 µM.

rHu-bFGF: Stock concentration of 180 ng/µL:

R&D rHu-bFGF: Added 139 µl of the appropriate vehicle above is added to the 25 µg vial lyophilized vial. 13.3 µL of the [180 ng/µl] stock vial and added 26.6 µL of vehicle to yield a final concentration of 3.75 µM concentration.

Nitro-cellulose disk preparation: The tip of a 20-gauge needle is cut off square and beveled with emery paper to create a punch. This tip is then used to cut out ≅0.5 mm diameter disks from a nitrocellulose filter paper sheet (Gelman Sciences). Prepared disks are then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µl of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention are active at doses less than 150 mpk.

Rat Adjuvant Arthritis Model

The rat adjuvant arthritis model (Pearson, Proc. Soc. Exp. Biol. 91:95-101 (1956)) is used to test the anti-arthritic activity of compounds of the Formula I, or salts thereof. Adjuvant Arthritis can be treated using two different dosing schedules: either (i) starting time of immunization with adjuvant (prophylactic dosing); or from day 15 when the arthritic response is already established (therapeutic dosing). Preferably a therapeutic dosing schedule is used.

Rat Carrageenan-induced Analgesia Test

The rat carrageenan analgesia test is performed with materials, reagents and procedures essentially as described by Hargreaves, et al., (Pain, 32:77 (1988)). Male Sprague-Dawley rats are treated as previously described for the Carrageenan Foot Pad Edema test. Three hours after the injection of the carrageenan, the rats are placed in a special plexiglass container with a transparent floor having a high intensity lamp as a radiant heat source, positionable under the floor. After an initial twenty minute period, thermal stimulation is begun on either the injected foot or on the contralateral uninjected foot. A photoelectric cell turned off the lamp and timer when light is interrupted by paw withdrawal. The time until the rat withdraws its foot is then measured. The withdrawal latency in seconds is determined for the control and drug-treated groups, and percent inhibition of the hyperalgesic foot withdrawal determined.

Formulations

Also embraced within this invention is a class of pharmaceutical compositions comprising the active compounds of Formula I in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of Formula I

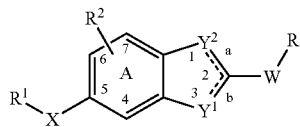

wherein W is $NR^4$;
X is O;
wherein $Y^1$ is N, $Y^2$ is O, dashed line "a" is absent and dashed line "b" indicates a bond;
wherein ring A is phenyl;
wherein R is selected from a) substituted or unsubstituted 6-10 membered aryl, or
b) substituted or unsubstituted cycloalkyl
wherein substituted R is substituted with one or more substituents independently selected from halo, $-OR^3$, $-SR^3$, $-CO_2R^3$, $-C(O)NR^3R^3$, $-C(O)R^3$, $-NR^3R^3$, oxo, $-OC(O)R^3$, $-SO_2R^3$, $-SO_2NR^3R^3$, $-NR^3C(O)OR^3$, $-NR^3C(O)R^3$, $-NR^3C(O)NR^3R^3$, optionally substituted cycloalkyl, optionally substituted 4-6 membered heterocyclyl, optionally substituted phenyl, cyano, alkylaminoalkoxy, alkylaminoalkoxyalkoxy, nitro, and lower alkyl substituted with $R^5$;
wherein $R^1$ is substituted or unsubstituted quinolinyl,
wherein $R^2$ is optionally substituted cycloalkyl, optionally substituted phenyl, cyano, alkylaminoalkoxy, alkylaminoalkoxyalkoxy, nitro, lower alkyl substituted with $R^5$, lower alkenyl substituted with $R^5$, and lower alkynyl substituted with $R^5$;
wherein $R^3$ is independently selected from H, lower alkyl, lower aminoalkyl, lower alkylaminoalkyl, optionally substituted phenyl, optionally substituted 3-6 membered heterocyclyl, optionally substituted $C_3$-$C_6$-cycloalkyl, optionally substituted phenylalkyl, optionally substituted 3-6 membered heterocyclylalkyl, optionally substituted $C_3$-$C_6$ cycloalkylalkyl, and lower haloalkyl;
wherein $R^4$ is independently selected from H, and lower alkyl; and
wherein $R^5$ is one or more substituents independently selected from H, halo, optionally substituted cycloalkyl, optionally substituted phenyl, cyano, alkylaminoalkoxy, and nitro;
and enantiomers, diastereomers, pharmaceutically acceptable salts and solvates thereof.

2. Compound of claim 1 wherein R is selected from substituted or unsubstituted aryl selected from phenyl, naphthyl, indanyl, indenyl and tetrahydronaphthyl, and $C_{3-6}$-cycloalkyl, wherein substituted R is substituted with one or more substituents independently selected from halo, $-OR^3$, oxo, $-SR^3$, $-SO_2R_3$, $-CO_2R^3$, $-C(O)NR^3R^3$, $-C(O)R^3$, $-NR^3R^3$, $-NH(C_1$-$C_4$ alkylenyl$R^3)$, $-(C_1$-$C_4$ alkylenyl)$NR^3R^3$, $-SO^2NR^3R^3$, $-NR^3C(O)OR^3$, $-NR^3C(O)R^3$, amino-$C_1C_6$-alkyl, $C_1$-$C_6$-alkylamino-$C_1$-$C_6$-alkyl, $C_1$-$C_6$-alkylamino-$C_1$-$C_6$-alkoxy, $C_1$-$C_6$-alkylamino-$C_1$-$C_6$-alkoxy-$C_1$-$C_6$-alkoxy, optionally substituted 5-6 membered heterocyclylcarbonylalkyl, $C_{1-4}$-alkoxycarbonylaxnino-$C_{1-6}$-alkyl,

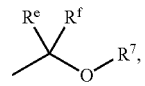

optionally substituted $C_{4-6}$-cycloalkyl, optionally substituted 5-6 membered heterocyclyl, optionally substituted phenyl, optionally substituted phenyl-$C_{1-6}$-alkylenyl, optionally substituted 5-6 membered heterocyclyl-$C_1$-$C_6$-alkylenyl, 5-6 membered heterocyclyl-$C_2$-$C_6$-alkenylenyl, $C_{1-4}$-alkyl, cyano, $C_{1-4}$-hydroxyalkyl, nitro and $C_{1-4}$-haloalkyl; wherein $R^e$ and $R^f$ are independently selected from H and $C_{1-2}$-haloalkyl; wherein $R^7$ is selected from H, $C_{1-3}$-alkyl, optionally substituted phenyl-$C_{1-3}$-alkyl, 4-6 membered heterocyclyl, optionally substituted 4-6 membered heterocyclyl-$C_1$-$C_3$-alkyl, $C_{1-3}$-alkoxy-$C_{1-2}$-alkyl and $C_{1-3}$-alkoxy-$C_{1-3}$-alkoxy-$C_{1-3}$-alkyl.

3. Compound of claim 1 wherein R is a substituted or unsubstituted ring selected from phenyl, indanyl, tetrahydronaphthyl, naphthyl, and cyclohexyl, wherein substituted R is substituted with 1-3 substituents independently selected from bromo, chloro, fluoro, iodo, nitro, amino, cyano, aminoethyl, hydroxy, axninosulfonyl, 4-methylpiperazinylsulfonyl, cyclohexyl, phenyl, phenylmethyl, morpholinylmethyl, methylpiperazinylmethyl, isopropyl-piperazinylmethyl, methylpiperazinylpropyl, morpholinylpropyl, methylpiperidinylmethyl, morpholinylethyl, 1-(4morpholinyl)-2,2-dimethylpropyl, piperidinylethyl, piperidinylmethyl, piperidinylpropyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-aminoethyl, 2-axninoethyl, 1-(N-isopropylamino)ethyl, 2-(N-isopropylamino)ethyl, dimethylaminopropyl, dimethylaminoethoxy, 4-chlorophenoxy, phenyloxy, 1-methylpiperdin-4-yloxy, piperdin-4-yloxy, piperidinylethoxy, morpholinylethyloxy, 4-methylpiperazinylethoxy, 4-isopropylpiperazinylethoxy, piperdin-4-methoxy, 4-methylpiperdin-1-ylmethoxy, 1-methylpyrrolidin-2-ylmethoxy, 1-isopropylpyrrolidin-2-ylmethoxy, 1-isopropylpyrrolidin-3-ylmethoxy, 1-methylpyrrolidin-3-ylmethoxy, 3-(dimethylaxnino)pyrrolidin-1-ylethoxy, isopropoxy, methoxy and ethoxy.

4. Compound of claim 1 wherein R is

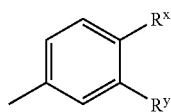

wherein $R^x$ is selected from bromo, chloro, methyl, ethyl, propyl, isopropyl, butyl, tert-butyl, sec-butyl, trifluoromethyl, pentafluoroethyl, 1,1-di(trifluoromethyl)-1-hydroxymethyl, trifluoromethoxy, difluoromethoxy, isopropoxy, methoxy and ethoxy; and wherein $R^y$ is selected from 4-methylpiperazinylsulfonyl, morpholinylmethyl, 4-methylpiperazinylmethyl, 4-methylpiperazinylpropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 3-dimethylaminopyrrolidin-1-ylmethyl, 1-methylpyrrolidin-2-ylmethyl, dimethylaminoethyl, dimethylaminoethoxy, piperidinylethoxy, morpholinylethyloxy, 4-methylpiperazinylethoxy, 4-isopropylpiperazinylmethoxy, piperdin-4-methoxy, 4-methylpiperdin-1-ylmethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-(N,N-dimethylamino)acetylamino and 2-(N,N-dimethylaxnino) ethylamino.

5. Compound of claim 1 wherein $R^1$ is a substituted or unsubstituted quinolinyl ring wherein substituted $R^1$ is substituted with one or more substituents independently selected from halo, hydroxy, $C_{1-3}$-alkyl, $C_{1-2}$-alkoxy, $C_{1-2}$-alkoxy-$C_{1-2}$-alkoxy, optionally substituted 5-6 membered heterocyclyl-$C_{1-2}$-alkoxy, amino, $C_{1-2}$-alkylainino, aminosulfonyl, —$NR^3C(O)OR^3$, —$NR^3C(O)R^3$, optionally substituted 5-6 membered heterocyclyl, optionally substituted phenyl, nitro, cyano, $C_{1-2}$-alkylamino-$C_{1-2}$-alkoxy, $C_{1-2}$-alkylamino-$C_{1-2}$-alkyl, $C_{1-2}$-alkylaxnino-$C_{2-3}$-alkylamino, $C_{1-2}$-hydroxyalkyl, $C_{1-2}$-aminoalkyl, and $C_{1-2}$-haloalkyl.

6. Compound of claim 1 wherein $R^1$ is a substituted or unsubstituted quinolyl ring wherein substituted $R^1$ is substituted with one or more substituents independently selected from chloro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholinoethoxy, pyrrolidin-1-ylethoxy, 4-methylpiperazin-1-ylethoxy, dimethylaminoethylamino, dimethylaminopropylamino, methyl, ethyl, propyl, cyano, hydroxymethyl, aminomethyl, aminocarbonyl, nitro, trifluoromethyl, optionally substituted piperidinyl, morpholinyl, optionally substituted piperazinyl, and optionally substituted phenyl.

7. Compound of claim 1 wherein $R^2$ is one or more substituents independently selected from H, chloro, fluoro, bromo, cyclopropyl, optionally substituted phenyl, methyl, ethyl, propyl, cyano, and, nitro.

8. Compound of claim 1 wherein $R^2$ is H; wherein $R^3$ is selected from H, $C_{1-4}$-alkyl, phenyl, phenyl-$C_{1-4}$-alkyl, 4-6 membered heterocyclyl, 4-6 membered heterocyclyl-$C_{1-3}$-alkyl, $C_3$-$C_6$ cycloalkyl and $C_{1-2}$-haloalkyl.

9. Compound of claim 1 wherein $R^4$ is independently selected from H, $C_{1-3}$-alkyl, phenyl, 5-6 membered heterocyclyl, $C_5$-$C_6$ cycloalkyl, and $C_{1-3}$-haloalkl.

10. Compound of Formula III

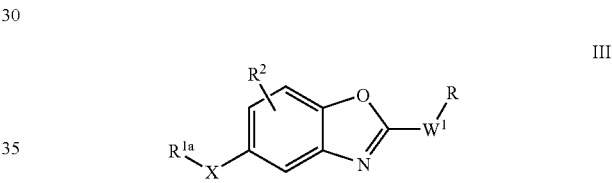

wherein $W^1$ is NH, and X is O;
wherein R is selected from
a) substituted or unsubstituted 6-10 membered aryl, or
d) substituted or unsubstituted cycloalkyl,
wherein substituted R is substituted with one or more substituents independently selected from halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, oxo, —$OC(O)R^3$, optionally substituted cycloalkyl, optionally substituted 4-6 membered heterocyclyl, optionally substituted phenyl, cyano, alkylaminoalkoxy, alkylaminoalkoxyalkoxy, nitro and lower alkyl substituted with $R^6$;
wherein $R^{1a}$ is selected from unsubstituted or substituted quinolinyl, and where substituted $R^{1a}$ is substituted with one or more substituents selected from halo, —$OR^3$, —$SR^3$, —$SO_2R^3$, —$CO_2R^3$, —$C(O)R^3$, —$NR^3R^3$, $SO_2NR^3R^3$, —$NR^3C(O)OR^3$, —$NR^3C(O)R^3$, optionally substituted 3-6 membered heterocyclyl, optionally substituted phenyl, nitro, cyano, oxo, and lower alkyl substituted with $R^6$;
wherein $R^2$ is one or more substituents independently selected from H, halo, —$OR^3$, —$SR^3$, —$CO_2R^3$, —$C(O)NR^3R^3$, —$C(O)R^3$, —$NR^3R^3$, —$SO_2R^3$, —$SO_2NR^3R^3$, —$NR^3C(O)OR^3$, —$NR^3C(O)R^3$, —$NR^3C(O)NR^3R^3$, optionally substituted cycloalkyl, optionally substituted 4-6 membered heterocyclyl, optionally substituted phenyl, cyano, alkylaminoalkoxy, nitro, and lower alkyl substituted with $R^6$;

wherein R³ is independently selected from H, lower alkyl, optionally substituted phenyl, optionally substituted 3-6 membered heterocyclyl, optionally substituted C₃-C₆-cycloalkyl, optionally substituted phenylalkyl, optionally substituted 3-6 membered heterocyclylalkyl, optionally substituted C₃-C₆ cycloalkylalkyl, lower aminoalkyl, lower alkylaminoalkyl and lower haloalkyl; and wherein R⁶ is one or more substituents independently selected from H, halo, optionally substituted cycloalkyl, optionally substituted phenyl, cyano, alkylaminoalkoxy and nitro;

enantiomers, diastereomers and pharmaceutically acceptable salts and solvates thereof.

11. Compound of claim 10 wherein R is a substituted or unsubstituted ring selected from phenyl, indanyl, tetrahydronaphthyl, naphthyl, and cyclohexyl, wherein substituted R is substituted with 1-3 substituents independently selected from bromo, chloro, fluoro, iodo, nitro, amino, cyano, aminoethyl, hydroxy, aminosulfonyl, 4-methylpiperazinylsulfonyl, cyclohexyl, phenyl, phenylmethyl, morpholin-4-ylmethyl, 4-methylpiperazin-1-ylmethyl, 4-isopropyl-piperazin-1-ylmethyl, 4-methylpiperazin-1-ylpropyl, morpholin-4-ylpropyl, methylpiperidinylmethyl, morpholin-4-ylethyl, 1-(4-morpholinyl)-2,2-dimethyipropyl, piperidinylethyl, piperidinylmethyl, piperidinylpropyl, 4-(dimethylaminoethyl)piperazin-1-ylmethyl, 1-methylpyrrolidinylmethyl, pyrrolidinylpropyl, methylsulfonyl, methylcarbonyl, piperidinylmethylcarbonyl, methylpiperazinylcarbonylethyl, methoxycarbonyl, methyl, ethyl, propyl, isopropyl, butyl, tert-butyl, sec-butyl, trifluoromethyl, pentafluoroethyl, nonafluorobutyl, 1,1-di(trifluoromethyl)-1-hydroxymethyl, 1,1-di(trifluoromethyl)-1-(piperidinylethoxy)methyl, 1,1-di(trifluoromethyl)-1-(methoxyethoxyethoxy)methyl, 1-hydroxyethyl, 2-hydroxyethyl, hydroxybutyl, difluoromethoxy, trifluoromethoxy, 1-amninoethyl, 2-aminoethyl, 1-(N-isopropylamino) ethyl, 2-(N-isopropylamino)ethyl, dimethylamninopropyl, dimethylaminoethoxy, diethylaminoethoxy, 4-chiorophenoxy, phenyloxy, 1-methylpiperdin-4-yloxy, piperdin-4-yloxy, piperidinylethoxy, morpholin-4-ylethyloxy, 4-methylpiperazin-l-ylethoxy, 4-isopropylpiperazinylethoxy, piperdin-4-ylmethoxy, 4-methylpiperdin-1-ylmethoxy, 1-methylpiperdin-4-ylmethoxy, 1-isopropylpiperdin-4-ylmethoxy, 1-methylpyrrolidin-2-ylmethoxy, 1-isopropylpyrrolidin-2-ylmethoxy, 1-isopropylpyrrolidin-3-ylmethoxy, 1-pyrrolidinylmethoxy, 1-pyrrolidinylethoxy, 1-methylpyrrolidin-3-ylmethoxy, 3-(dimethylamino)pyrrolidin-1-ylethoxy, 2-tetrahydrofurylmethoxy, isopropoxy, methoxy and ethoxy.

12. Compound of claim 10 wherein R is

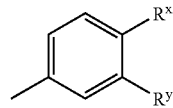

wherein R^x is selected from bromo, chloro, methyl, ethyl, propyl, isopropyl, butyl, tert-butyl, sec-butyl, trifluoromethyl, pentafluoroethyl, 1,1-di (trifluoromethyl)-1-hydroxymethyl, trifluoromethoxy, difluoromethoxy, isopropoxy, methoxy and ethoxy; and wherein R^y is selected from H, 4-methylpiperazinylsulfonyl, trifluoromethyl, morpholinylmethyl, 4-methylpiperazinylmethyl, 3-dimethylaminopyrrolidin-1-ylmethyl, 4-methylpiperazinyipropyl, 4-isopropylpiperazinylmethyl, 4-methylpiperidinylmethyl, 4-aminopiperidinylmethyl, 4-methylamino-piperidinylmethyl, 4-dimethylamino-piperidinylmethyl, 1-methylpyrrolidin-2-ylmethyl, dimethylaminoethyl, dimethylaminoethoxy, piperidinylethoxy, morpholinylethyloxy, 4-methylpiperazin-1-ylethoxy, 4-(dimethylaminoethyl)piperazin-1-ylmethyl, 4-isopropylpiperazinylmethoxy, piperdin-4-ylmethoxy, 4-methylpiperdin-1-ylmethoxy, 1-methylpiperdin-4-ylmethoxy, 1-isopropylpiperdin-4-ylmethoxy, 1-pyrrolidinylmethoxy, 1-pyrrolidinylethoxy, 1-methylpyrrolidin-2-ylmethoxy, 1-methylpyrrolidin-3-ylmethoxy, 1-isopropylpyrrolidin-2-ylmethoxy, 1-isopropylpyrrolidin-3-ylmethoxy, 3-(dimethylamino)pyrrolidin-1-ylethoxy, 2-tetrahydrofurylmethoxy, diethylamninoethoxy, 2-(N,N-dimethylamino) acetylainino and 2-(N,N-dimethylamino) ethylamino.

13. Compound of claim 10 wherein R^{1a} is a substituted or unsubstituted 4-quinolyl ring wherein substituted R^{1a} is substituted with one or more substituents independently selected from chioro, fluoro, bromo, hydroxy, methoxy, ethoxy, methoxyethoxy, amino, methylamino, ethylamino, 1-methylpiperidinylmethoxy, aminosulfonyl, dimethylaminoethoxy, piperdinylmethoxy, piperdin-1-ylethoxy, morpholinoethoxy, pyrrolidin-1-ylethoxy, 4methylpiperazin-1-ylethoxy, methylaminocarbonyl, 1-pyrrolidinylbutylaminocarbonyl, dimethylaminoethylamino, dimethylaminopropylamino, methyl, ethyl, propyl, cyano, hydroxyrnethyl, aminomethyl, aminocarbonyl, nitro, trifluoromethyl, optionally substituted piperidinyl, morpholinyl, optionally substituted piperazinyl, and optionally substituted phenyl.

14. Compound of claim 10 wherein R² is H or Cl.

15. A pharmaceutical composition comprising a pharmaceutically-acceptable carrier and a compound as in claim 1 or 10.

* * * * *